US012620461B2

(12) United States Patent
Cooper et al.

(10) Patent No.: US 12,620,461 B2
(45) Date of Patent: May 5, 2026

(54) VISUAL INTERFACE FOR GENERATION OF GROUPS AND EXPERIMENT BUILDING

(71) Applicant: Agilent Technologies, Inc., Santa Clara, CA (US)

(72) Inventors: Joshua Cooper, Santa Clara, CA (US); Benjamin Paradis, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 150 days.

(21) Appl. No.: 18/567,091

(22) PCT Filed: Jun. 14, 2022

(86) PCT No.: PCT/US2022/033441
§ 371 (c)(1),
(2) Date: Dec. 5, 2023

(87) PCT Pub. No.: WO2022/266104
PCT Pub. Date: Dec. 22, 2022

(65) Prior Publication Data
US 2024/0266011 A1 Aug. 8, 2024

Related U.S. Application Data

(60) Provisional application No. 63/211,240, filed on Jun. 16, 2021.

(51) Int. Cl.
*G16H 10/40* (2018.01)
(52) U.S. Cl.
CPC .................................. *G16H 10/40* (2018.01)

(58) Field of Classification Search
None
See application file for complete search history.

(56) References Cited

U.S. PATENT DOCUMENTS

2016/0319329 A1 11/2016 Natale et al.
2018/0253194 A1* 9/2018 Javadi ........................ G06F 8/38
2020/0368739 A1 11/2020 Berberich et al.

FOREIGN PATENT DOCUMENTS

EP 1 188 126 B1 4/2005
WO WO-2017004468 A1 * 1/2017 ............. G16C 20/90

OTHER PUBLICATIONS

Delorme, Vincent, et al. "PlateEditor: A web-based application for the management of multi-well plate layouts and associated data." Plos one 16.5 (2021): e0252488. (Year: 2021).*
International Search Report and Written Opinion for PCT/US2022/033441, dated Oct. 4, 2022, 14 pages.

* cited by examiner

*Primary Examiner* — Jason B Dunham
*Assistant Examiner* — Constantine Siozopoulos
(74) *Attorney, Agent, or Firm* — Dority & Manning, P.A.

(57) ABSTRACT

A user interface that includes a plate map that automatically updates to provide indicia descriptive of parameter assignments and parameter groups can provide an intuitive system for building experiments. For example, a user may provide one or more inputs to generate and assign a parameter setting to a plurality of cells that represent a plurality of wells. The user interface may update the plate map to depict one or more indicia to indicate which wells have been assigned the new parameter setting.

20 Claims, 40 Drawing Sheets

600

Provide a Plate Experiment Interface for Display —602

Receive One or More Inputs to Generate a New Parameter Setting —604

Generate the New Parameter Setting Based on the One or More Inputs —606

Receive One or More Selections to Assign the New Parameter Setting to One or More Wells Represented in the Plate Map —608

Provide a Updated Plate Experiment Interface for Display —610

700

Receive One or More Inputs to Generate a Parameter Setting — 702

Generate the Parameter Setting Based on the One or More Inputs — 704

Receive a Selection of One or More Samples for Parameter Assignment — 706

Assign the Parameter Setting to the One or More Samples — 708

Provide a Plate Map for Display — 710

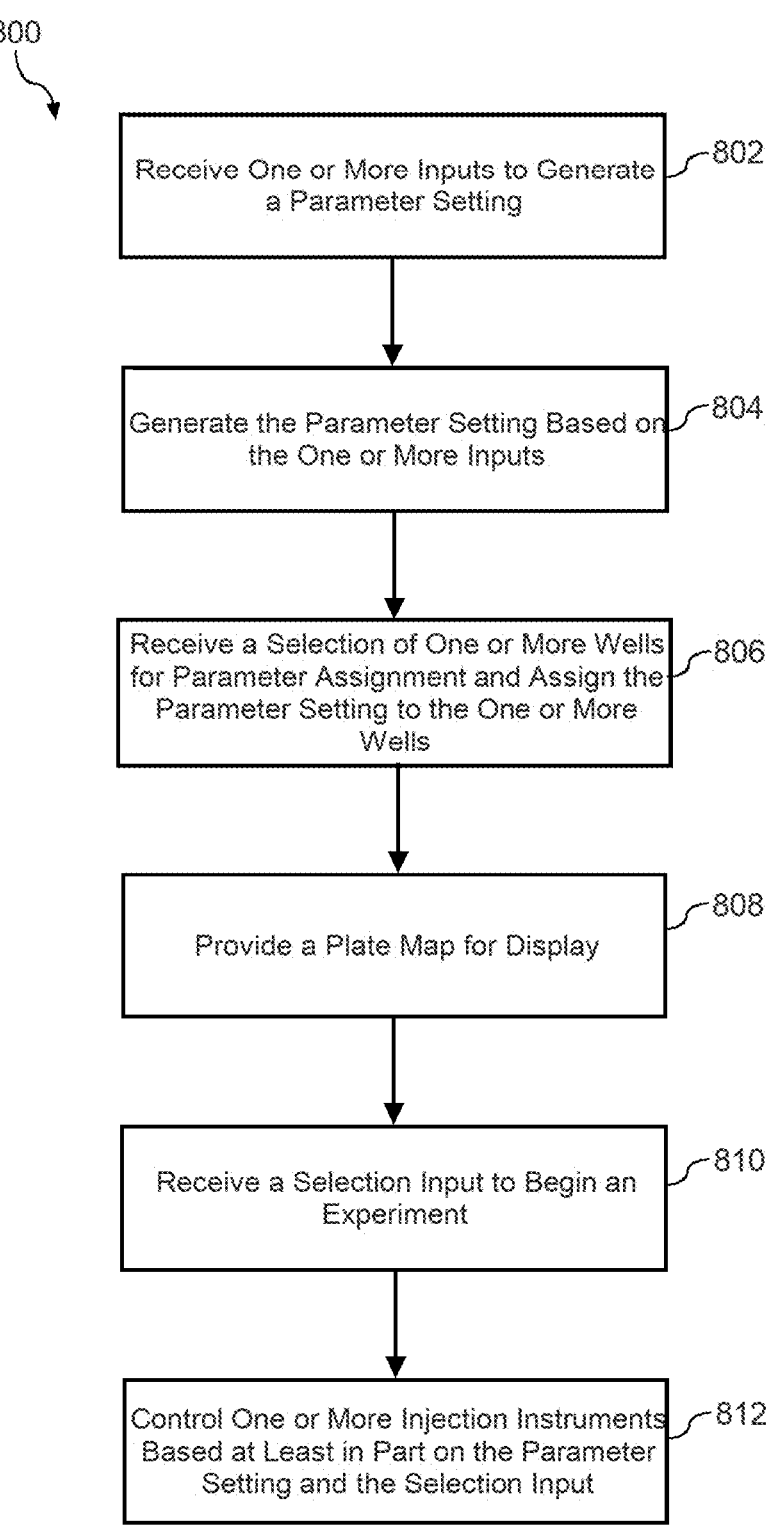

800

Receive One or More Inputs to Generate a Parameter Setting — 802

Generate the Parameter Setting Based on the One or More Inputs — 804

Receive a Selection of One or More Wells for Parameter Assignment and Assign the Parameter Setting to the One or More Wells — 806

Provide a Plate Map for Display — 808

Receive a Selection Input to Begin an Experiment — 810

Control One or More Injection Instruments Based at Least in Part on the Parameter Setting and the Selection Input — 812

FIG. 8

VISUAL INTERFACE FOR GENERATION OF GROUPS AND EXPERIMENT BUILDING

RELATED APPLICATIONS

This application claims priority to and the benefit of U.S. Provisional Patent Application No. 63/211,240, filed Jun. 16, 2021. U.S. Provisional Patent Application No. 63/211,240 is hereby incorporated by reference in its entirety.

FIELD

The present disclosure relates generally to a user interface for configuring plate experiments. More particularly, the present disclosure relates to systems and methods for providing a plate experiment interface for receiving inputs to generate a plate map that can aid in plate experimentation.

BACKGROUND

For assay experiments, users often need to enter data for plates that may have many wells. Some existing solutions can rely on entering parameters as data into a spreadsheet. The method can require a user to manually enter repetitive parameter data into fields. The grouping of wells can also be completed manually. A couple disadvantages of the method can be that the method takes much longer and can be more susceptible to user errors. Moreover, other existing systems can rely on a user first creating a group and manually configuring the groups before assigning the parameters to the wells.

The existing systems can involve tedious input, which can be inefficient and conducive to errors. Moreover, the existing systems can discourage users from adding more detailed parameter data, resulting in sparsely detailed assay designs. Furthermore, the existing systems can cause problems downstream in the workflow including reduced instrument usage, data reproducibility problems, and delayed discoveries.

SUMMARY

Aspects and advantages of embodiments of the present disclosure will be set forth in part in the following description, or can be learned from the description, or can be learned through practice of the embodiments.

One example aspect of the present disclosure is directed to a computer-implemented method for setting parameters for an experiment. The method can include providing, by a computing system including one or more processors, a plate experiment interface for display. In some implementations, the plate experiment interface can include a plate map. The method can include receiving, by the computing system, one or more inputs to generate a new parameter setting. The method can include generating, by the computing system, the new parameter setting based on the one or more inputs. The method can include receiving, by the computing system, one or more selections to assign the new parameter setting to one or more wells represented in the plate map. In some implementations, the method can include providing, by the computing system, an updated plate experiment interface for display. The one or more wells can be displayed with a first indicia to indicate a first grouping.

In some implementations, the one or more wells can be displayed with a first character to indicate the one or more wells are assigned the new parameter setting. The method can include adjusting, by the computing system, a parameter setting for each of the one or more wells based at least in part on the new parameter setting. The method can include receiving, by the computing system, one or more finalization selections from a user to finalize the new parameter setting and providing, by the computing system, a finalization interface for display. In some implementations, the finalization interface can include an updated plate map and group information descriptive of a set of parameter settings for each respective grouping. The method can include receiving, by the computing system, a new tab selection from a user and removing, by the computing system, a first indicia from the updated plate experiment interface.

In some implementations, the plate experiment interface can include a plurality of tabs, and each tab can be associated with a different display of the plate map. The plurality of tabs can include an injection strategy setting tab, a pretreatment setting tab, an assay media setting tab, and a cell type setting tab. In some implementations, the plurality of tabs can include a finalization tab, and the finalization tab can be associated with a fully-configured plate map. The new parameter setting can be at least one of an injection strategy setting, a pretreatment setting, an assay media setting, or a cell type setting.

In some implementations, the method can include receiving, by the computing system, one or more second inputs to generate a second parameter setting; generating, by the computing system, the second parameter setting based on the one or more second inputs; receiving, by the computing system, one or more selections to assign the second parameter setting to a subset of the one or more wells represented in the plate map; and providing, by the computing system, an adjusted plate experiment interface for display. The subset of the one or more wells can be displayed with a second color to indicate a second grouping, and the subset of the one or more wells can be displayed with a second character to indicate the subset of the one or more wells are assigned the second parameter setting. The second parameter setting can be at least one of an injection strategy setting, a pretreatment setting, an assay media setting, or a cell type setting.

In some implementations, the method can include receiving, by the computing system, secondary input data associated with a second parameter setting; generating, by the computing system, a second grouping with the second parameter setting; providing, by the computing system, group information associated with the first grouping and the second grouping for display in the updated plate experiment interface; determining, by the computing system, the second grouping is without assignment on the plate map; and removing, by the computing system, a subset of the group information from the updated plate experiment interface. The subset can be associated with the second grouping.

Another example aspect of the present disclosure is directed to a computing system. The computing system can include one or more processors and one or more non-transitory computer readable media that collectively store instructions that, when executed by the one or more processors, cause the computing system to perform operations. The operations can include receiving one or more inputs to generate a parameter setting and generating the parameter setting based on the one or more inputs. The operations can include receiving a selection of one or more samples for parameter assignment and assigning the parameter setting to the one or more samples. In some implementations, the operations can include providing a plate map for display. A portion of the plate map representing the one or more samples can be displayed with one or more indicia.

In some implementations, the plate map can include at least 8 samples. The operations can include providing a groups column for display. In some implementations, the groups column can be displayed simultaneously with the plate map, and the groups column can include group information. The operations can include providing a parameter column for display. In some implementations, the parameter column can be displayed simultaneously with the plate map, and the parameter column can include a title descriptive of a parameter type and one or more assignment-ready parameters. The one or more assignment-ready parameters can include the parameter setting. In some implementations, the indicia can include a first indicia descriptive of the parameter setting and a second indicia descriptive of a well grouping.

Another example aspect of the present disclosure is directed to an experiment computing system. The experiment computing system can include a plate including a plurality of wells. The experiment computing system can include one or more injection instruments and one or more visual displays for displaying visual components of a user interface. The experiment computing system can include one or more input components configured to receive inputs from a user, one or more processors, and one or more non-transitory computer readable media that collectively store instructions that, when executed by the one or more processors, cause the experiment computing system to perform operations. The operations can include receiving one or more inputs to generate a parameter setting. The operations can include generating the parameter setting based on the one or more inputs and receiving a selection of one or more wells for parameter assignment. The operations can include assigning the parameter setting to the one or more wells and provide a plate map for display with the one or more visual displays. In some implementations, a portion of the plate map representing the one or more wells can be displayed in at least one of a different color or with a number. The operations can include receiving a selection input to begin an experiment and control one or more injection instruments based at least in part on the parameter setting and the selection input.

In some implementations, the one or more injection instruments can include a plurality of injection ports for injecting a plurality of compounds. The experiment computing system can include one or more pretreatment instruments. In some implementations, the operations can include receiving one or more second inputs to generate a second parameter setting, generating the second parameter setting based on the one or more second inputs, receiving a second selection of a second set of one or more wells for a second parameter assignment, assigning the second parameter setting to the second set of one or more wells, and controlling the one or more pretreatment instruments based at least in part on the second parameter setting and the selection input.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

4

BRIEF DESCRIPTION OF THE DRAWINGS

Detailed discussion of embodiments directed to one of ordinary skill in the art is set forth in the specification, which makes reference to the appended figures, in which:

FIG. 3I depicts an illustration of an example assay media parameter configuration according to example embodiments of the present disclosure.

FIG. 3O depicts an illustration of an example finalization tab according to example embodiments of the present disclosure.

FIG. 8 depicts a flow chart diagram of an example method to perform plate assay building according to example embodiments of the present disclosure.

Figure 1:
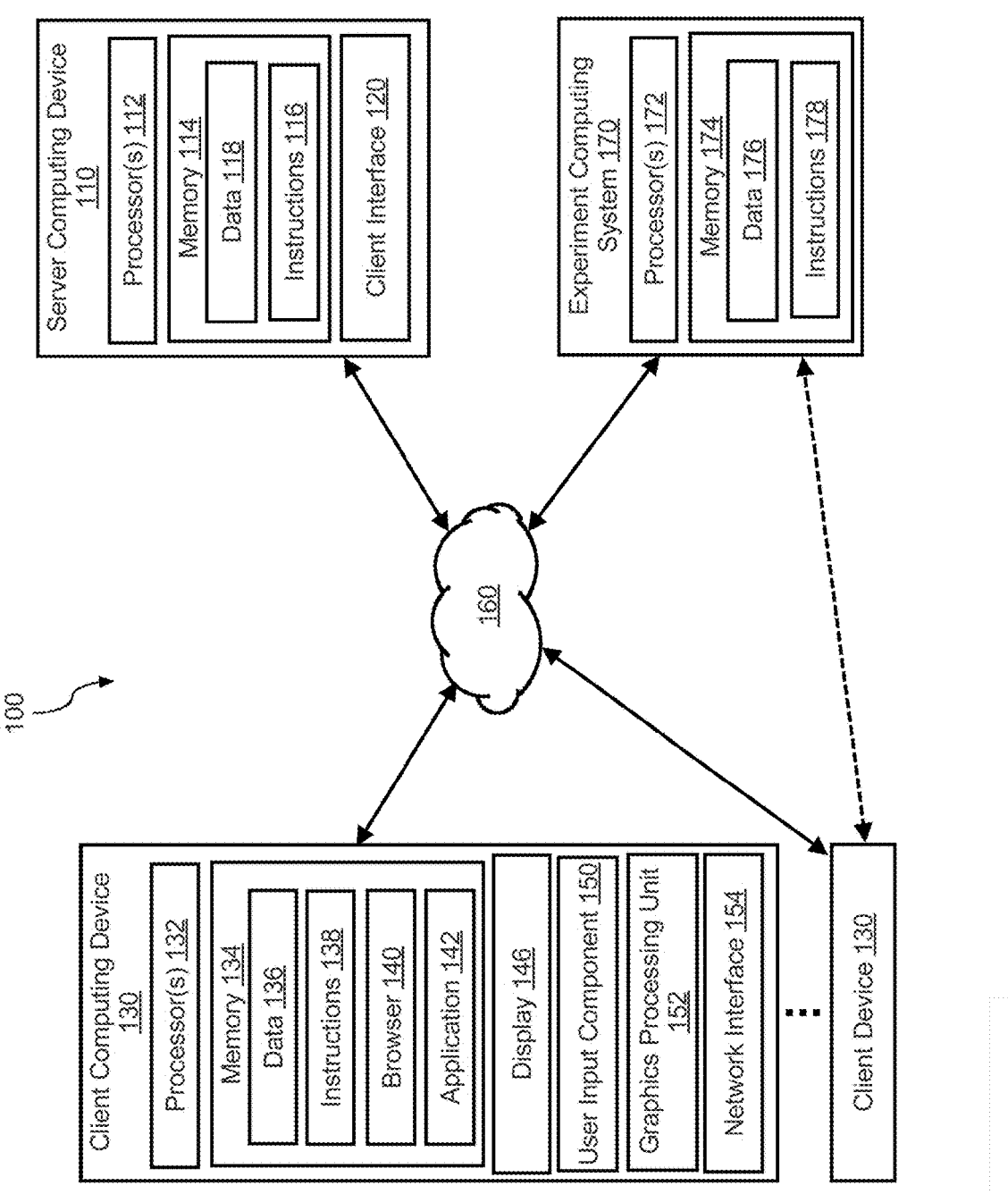
FIG. 1 depicts a block diagram of an example computing system that performs plate experiment building according to example embodiments of the present disclosure.

Reference numerals that are repeated across plural figures are intended to identify the same features in various implementations.

DETAILED DESCRIPTION

Example aspects of the present disclosure are directed to systems and methods for providing a user interface for experiment building. More specifically, the systems and methods disclosed herein can receive a plurality of user inputs, assign parameters to samples, generate groups, and provide a plate map depicting sample groups. In some implementations, the systems and methods can provide a plate experiment interface for display. The plate experiment interface can include a plate map and one or more parameter tabs. Moreover, in some implementations, the plate experiment interface may include a finalization tab, a parameter column, and/or a grouping column. The systems and methods can receive one or more inputs to generate a new parameter setting and can generate the new parameter setting based on the one or more inputs. Next, the systems and methods can include receiving one or more selections to assign the new parameter setting to one or more samples represented in the plate map. The updated plate experiment interface can then be provided for display. In some implementations, the one or more samples can be displayed with a first indicia to indicate a first grouping. The first indicia can be a first color, a first character, and/or first pattern. Alternatively and/or additionally, a second indicia (e.g., a character, a color, and/or a pattern) may also be displayed to indicate the assignment of the new parameter setting. The process may be completed multiple times for different parameter types, and the sample grouping may be updated as more parameters are assigned. In some implementations, the parameters of the one or more samples may be adjusted based at least in part on the assigned new parameter setting.

In some implementations, the systems and methods can include receiving one or more finalization selections from a user to finalize the new parameter setting. In response to the finalization selection, the systems and methods may provide a finalization interface for display. The finalization interface can include an updated plate map and group information descriptive of a set of parameter settings for each respective grouping.

The systems and methods disclosed herein can include a plurality of tabs which can be navigated to and from by receiving a new tab selection from a user. In response to the new tab selection, the systems and methods may remove the first character from the updated plate experiment interface. The tabs may represent different parameter types. In some implementations, each tab of the plurality of tabs can have a different display of the plate map. The different display can be caused based on different parameter setting indicia being shown on each tab. In some implementations, the samples may be wells for a plate assay experiment. Moreover, in some implementations, the plurality of parameter types can include injection strategy parameters, pretreatment parameters, assay media parameters, and cell type parameters, and the plurality of tabs can include an injection strategy setting tab, a pretreatment setting tab, an assay media setting tab, and a cell type setting tab. The plate experiment interface can include a finalization tab that can be selected to display the fully-configured plate map. In some implementations, further group editing can be completed in the finalization tab. Moreover, in some implementations, the finalization tab may include a different display of the plate map in which parameter setting indicia may be removed, and the grouping indicia may be provided in a different format.

In some implementations, the systems and methods disclosed herein can be used to control one or more experiment instruments, which can include an injection instrument, a pretreatment instrument, and/or a variety of other instruments. The generated plate experiment may be downloaded and then uploaded to the experiment machinery to provide fully or partially automated experimentation.

Building assays or experiments for plate based instruments can be tedious and not very intuitive. Current techniques have a user manually inputting parameters for each well individually, which can be time consuming and error conducive. The systems and methods disclosed herein can reduce the time of set-up and provide a more intuitive way for building assays and other experiments.

The systems and methods disclosed herein can provide a user interface that enables a user to quickly and intuitively set the parameters for a plurality of wells. In some implementations, the systems and methods can utilize a multiple tab user interface with a visual indication of the placement of well parameters for each condition. The interface can allow the user to easily see which wells, or samples, share the same parameters and what the parameters are. The grouping of wells can be automatically generated based on user inputs, and each tab may build on the previous tab. The various graphical elements can allow the user to easily understand the parameters being assigned along with the groups being created when setting parameters for an experiment.

The systems and methods can allow users to apply parameters directly to a plate map in a layered method while creating assay groups based on the different parameter combinations in real-time. The systems and methods can provide a clear visualization of the location of individual parameters on the plate and can shorten the time required for assay setup.

Existing methods can rely on the user's expertise (scientifically & technically), and familiarity (with the assay, product, and software) to ensure error-free assay parameter transposition, setup, and execution. This can be intimidating to infrequent, new, non-expert users, discouraging them from performing assays themselves. The systems and methods disclosed herein can provide a real-time visualization of parameter placement on a plate map-centric view to give the user confidence that assay parameters are assigned how they intended them to be, while also increasing efficiency.

The systems and methods can generate pre-populated group definition catalogs and auto-fill features to minimize the amount of manual data entry, reducing time during pre-assay setup, while mitigating errors caused by inconsistent entry and application of redundant parameter data (e.g., repetitive data transposition). Moreover, more detailed and complete parameter defining can ensure a richly detailed assay result file. The assay parameter metadata can be fundamental for any analytical interpretation, discussion, presentation, collaboration, or for assay repetition. A highly detailed assay result file can ensure the greatest chance of success in all these areas, allowing the user to focus on meaning of the data and accelerate discovery.

In some implementations, the systems and methods can provide for display a blank plate map with one or more tabs, in which each tab can represent a different category of parameters. The system can receive a selection of a tab and provide an interface configured to receive data associated with a parameter (e.g., a dialog box for adding descriptive data for the parameter, a dropdown list for predefined parameters, and/or one or more selectable buttons). The system can obtain one or more inputs to add a parameter. In response to the one or more inputs, the parameter can be added for mapping to the blank plate map.

In some implementations, the added parameters can then be assigned to one or more wells by selection of the boxes representative of the respective wells, by dragging and dropping the parameter, or via a variety of other input methods. Once wells are assigned parameters, the plate map can indicate the well has an assigned parameter by showing a number representative of the assigned parameter and/or a color representative of the assigned parameter. In some implementations, a number can indicate the assigned parameter, and a color can indicate a grouping of wells with the same parameters. Group information (e.g., the group color and the parameters assigned for that group) can be displayed with the plate map and the parameter information for the open tab. As more parameters are generated and assigned, the plate map, the tab information, and the group information can be updated and displayed. In some implementations, the groups previously displayed can be split based on updated parameters, such that two groups may share a same first parameter but be displayed as different colors based on differing second parameters. In some implementations, when a new tab is selected, the numbers on the plate map from the previous parameter tab may be removed or replaced by numbers indicating the selected parameters for that specific parameter tab. The colors indicating the different well groups can be displayed regardless of which parameter tab is open in order to display different groupings already created.

Once the user has completed selections and assignments, the system may receive a finalization input. In response to the finalization input, the system can provide a review interface which can display the final plate map with color coding for the grouping and an overview of the group information for each respective group, which can be adjusted to correct any errors before finalizing the parameters for the experiments or assays. In some implementations, new assignments and new groups can be created while on the finalization tab. Moreover, in some implementations, the plate map may have a different appearance when the finalization tab is selected.

The plate map can be used as a template for setting-up, running, and cataloging a variety of experiments (e.g., an assay experiment). For example, a user can select one or more parameters (e.g., pre-defined parameters or user-created parameters) to assign to one or more wells in the plate map. The user can define new parameters or select previously defined parameters and then assign the parameters until a complete experiment is formulated. The user can review the plate map and group information to ensure the experiment has been formulated how they want it to be formulated. The user can then use the formulated plate map and group information as reference during the set-up of the experiment. In some implementations, the plate map and group information can be used as reference for cataloging experiment results. Moreover, the plate experiment interface can include a notes section for including notes on the experiment, the configuration, or the parameters.

Additionally and/or alternatively, the plate experiment interface can include one or more options for downloading the generated experiment configuration. For example, the download feature may generate a report for easy reference of the plate map and group information. Alternatively and/or additionally, the download feature may generate a file that can be easily uploaded to a computing system that can run the experiment. The computing system can include one or more injection instruments, one or more pretreatment instruments, and/or one or more other instruments.

In some implementations, the plate experiment interface can include a protocol page that can be interacted with to edit or generate more details for the experiment. The protocol page may also define the steps and time period needed for the experiment. The protocol page can also provide logistics for the experiment and/or may provide an interface for testing the plausibility of completing the generated experiment based on a variety of factors.

The systems and methods disclosed herein can be utilized for configuring and running a variety of experiments, which can include assay experiments, substrate creation, substrate testing, material property experiments, general sample testing, and/or a variety of other experiments.

In some implementations, the plate map can include a plurality of boxes, or cells, descriptive of a plurality of samples, or wells. The plate map can include background boxes descriptive of background wells or unusable spaces. There can be any number of boxes descriptive of any number of wells. In some implementations, the plate map can have at least 96 boxes descriptive of at least 96 wells. Alternatively, the plate map can represent 384 wells, 1536 wells, or any other number of wells.

In some implementations, the systems and methods disclosed herein can include an automatic group cleanup. The automatic group cleanup can be utilized to remove and/or hide group information for groups that are not being utilized. For example, a user may make a plurality of selections to generate a first group (e.g., a first group with a first set of selected parameters), and the user may make a plurality of selections to generate a second group (e.g., a second group with a second set of selected parameters). The user may originally assign the first group to one or more first samples (e.g., one or more first wells). Additionally and/or alternatively, the user may originally assign the second group to one or more second samples (e.g., one or more second wells). The user can then decide to overwrite the previous assignment to assign the second group to the one or more first samples and the one or more second samples. The plate map can then display the one or more first blocks associated with the one or more first samples and the one or more second blocks associated with the one or more second samples having the same indicia descriptive of the second group. The systems and methods can then determine the first group is not being utilized. In response to the first group not being utilized, the automatic group cleanup system can remove and/or hide the first group from the group information portion of the user interface (e.g., the group column in the plate interface).

Additionally and/or alternatively, the automatic group cleanup can remove and/or merge redundant groups. For example, the automatic group cleanup can determine two or more groups share the same conditions (e.g., the same parameter settings (e.g., the same injection strategy setting, the same pretreatment setting, the same assay media setting, and the same cell type setting)). The automatic group cleanup can then merge the groups to remove the redundancy of having two or more groups with duplicate conditions.

The automatic group cleanup can occur at given intervals (e.g., every few seconds, every few minutes, etc.). Alternatively and/or additionally, the automatic group cleanup can occur in response to a user selection. In some implementations, the automatic group cleanup can occur when a user switches between tabs.

In some implementations, the automatic group cleanup can be turned on and off by selecting an interactive user interface element. The interactive user interface element can include a slider, an icon, a dropdown menu, a selectable bubble, and/or any other form of user interface element.

The automatic group cleanup can include determining one or more groups of a plurality of generated groups are without assignment on the plate map. The one or more groups can then be deleted from the plurality of generated groups. Alternatively and/or additionally, the one or more groups may be removed from the displayed groups in the group information portion of the user interface.

For example, the systems and methods can receive first input data associated with a first parameter setting. A first grouping can be generated based on the first parameter setting, and the first grouping can be assigned to one or more blocks (e.g., one or more blocks associated with one or more samples) of the plate map. Additionally and/or alternatively, the systems and methods can receive secondary input data associated with a second parameter setting. A second grouping can be generated based on the second parameter setting. An updated plate experiment interface can be provided for display with group information associated with the first grouping and the second grouping. The systems and methods can then determine the second grouping is without assignment on the plate map. The determination may occur based on an intervallic check of the generated groups. In some implementations, the determination can be based on data associated with the generated groups and the plate map. The determination may be based on the second grouping not being assigned to any of the blocks of the plate map. In response to the determination, a subset of the group information can be removed from the updated plate experiment interface. The subset removed can be associated with the second grouping that was not being utilized.

In some implementations, the automatic group cleanup can merge redundant groups. For example, the systems and methods can determine two or more of the generated groups of the plurality of generated groups include matching parameter settings. In response to determining two or more of the generated groups of the plurality of generated groups include matching parameter settings, the systems and methods can switch all wells or samples depicting the two or more generated groups to display the same indicia. Additionally and/or alternatively, at least one of the two or more generated groups may be removed or hidden from the group information portion of the user interface. The samples (e.g., the wells) associated with the removed or hidden group can be reassigned to the matching group that remains.

In some implementations, the systems and methods disclosed herein can be utilized to control experiment equipment (e.g., analyzing equipment that measures energy metabolism of live cells in real time).

The systems and methods of the present disclosure provide a number of technical effects and benefits. As one example, the system and methods can provide systems and methods for configuring an experiment. More specifically, the systems and methods can receive a plurality of inputs and present a representation of an assay experiment based on the inputs. The interface for obtaining the inputs and displaying the representation can be intuitive and add efficiency to the experiment building process.

Another technical benefit of the systems and methods of the present disclosure is the ability to leverage a tabbed user interface with various indicia to provide a user with an intuitive way to input parameters and display the parameters assigned and the groups created. For example, a user can be on a first parameter tab and assign a first parameter to a first set of wells and a second parameter to a second set of wells. A plate map representation can display a first set of indicia to indicate the first parameter and the second parameter assignments and a second set of indicia to indicate two groups have been made. The user can then select a second parameter tab, which can remove the first set of indicia but leave the grouping indicia. A new set of indicia can be generated in response to new parameters being assigned along with new groups being made. The systems and methods can allow users to make groups more intuitively and better understand the groups that have been made.

Another example of technical effect and benefit relates to improved computational efficiency and improvements in the functioning of a computing system. For example, the systems and methods disclosed herein can leverage the download and upload feature of the systems and methods to allow for a user to be able to formulate the experiment and easily transfer formulated experiment details to the experiment computing system. The download and upload feature can save a user time by reducing the redundancy required by reentering inputs, and the feature can also reduce the computing power needed for the experiment by providing an interpretable upload in place of a plurality of inputs that would need to be interpreted by the computing system.

With reference now to the Figures, example embodiments of the present disclosure will be discussed in further detail.

Example Devices and Systems

FIG. 1 depicts an exemplary computing system 100 that can be used to implement experiment building according to aspects of the present disclosure. The system 100 has a client-server architecture that includes a server 110 that communicates with one or more client devices 130 over a network 160. However, the present disclosure can be implemented using other suitable architectures, such as a single computing device unconnected to a network. The system 100 can also have an experiment computing system 170 to run the experiment built by a user using the computing system 100.

The system 100 includes a server 110, such as, for example, a web server. The server 110 can be one or more computing devices that are implemented as a parallel or distributed computing system. In particular, multiple computing devices can act together as a single server 110. The server 110 can have one or more processor(s) 112 and a memory 114. The server 110 can also include a network interface used to communicate with one or more remote computing devices (e.g., client devices) 130 over a network 160.

The processor(s) 112 can be any suitable processing device, such as a microprocessor, microcontroller, integrated circuit, or other suitable processing device. The memory 114 can include any suitable computing system or media, including, but not limited to, non-transitory computer-readable media, RAM, ROM, hard drives, flash drives, or other memory devices. The memory 114 can store information accessible by processor(s) 112, including instructions 116 that can be executed by processor(s) 112. The instructions 116 can be any set of instructions that when executed by the processor(s) 112, cause the processor(s) 112 to provide desired functionality.

In particular, the instructions 116 can be executed by the processor(s) 112 to implement a client interface 120. The client interface 120 can be configured to provide an interface for a user to build an experiment. In some implementations, the client interface 120 can be configured to provide instructions to an experiment computing system 170 to perform an experiment. In particular, in some implementations, the client interface 120 can be provided for interaction with a user using a client computing system 130 that communicates with the server computing system 110 via a network 160.

It will be appreciated that the term "element" can refer to computer logic utilized to provide desired functionality. Thus, any element, function, and/or instructions can be implemented in hardware, application specific circuits, firmware and/or software controlling a general purpose processor. In one implementation, the elements or functions are program code files stored on the storage device, loaded into memory and executed by a processor or can be provided from computer program products, for example computer executable instructions, that are stored in a tangible computer-readable storage medium such as RAM, hard disk or optical or magnetic media.

Memory 114 can also include experiment data 118 that can be retrieved, manipulated, created, or stored by processor(s) 112. Experiment data 118 can include injection instrument information (e.g., injection compounds, possible injection parameters, injection size data, etc.), pretreatment information, cell type information, assay media information, tables, or other suitable experiment data or related information. As an example, experiment data 118 can be used to access information and data associated with possible parameters for building an experiment.

The experiment data 118 can be stored in one or more databases. The one or more databases can be connected to the server 110 by a high bandwidth LAN or WAN, or can also be connected to server 110 through a network 160. The one or more databases can be split up so that they are located in multiple locales.

The server 110 can exchange data with one or more client devices 130 over the network 160. Although two clients 130 are illustrated in FIG. 1, any number of client devices 130 can be connected to the server 110 over the network 160. The client devices 130 can be any suitable type of computing device, such as a general purpose computer, special purpose computer, navigational device, laptop, desktop, integrated circuit, mobile device, smartphone, tablet, wearable-computing devices, a display with one or more processors coupled thereto and/or embedded therein, or other suitable computing device. Further, a client device 130 can be multiple computing devices acting together to perform operations or computing actions.

Similar to server 110, a client device 130 can include a processor(s) 132 and a memory 134. The memory 134 can store information accessible by processor(s) 132, including instructions that can be executed by processor(s) and data. As an example, memory 134 can store a browser element 140 and an application element 142.

Browser element 140 can provide instructions for implementing a browser. In particular, the user of client device 130 can exchange data with server 110 by using the browser to visit a website accessible at a particular web-address. The experiment builder of the present disclosure can be provided as an element of a user interface of the website.

Application element 142 can provide instructions for running a specialized application on client device 130. In particular, the specialized application can be used to exchange data with server 110 over the network 160. Application element 142 can include client-device-readable code for providing and implementing aspects of the present disclosure. For example, application element 142 can provide instructions for implementing an experiment building application or a plate experiment user interface application.

The client device 130 can include various user input devices 150, or input components, for receiving information from a user, such as a touch screen, touch pad, data entry keys, speakers, mouse, motion sensor, and/or a microphone suitable for voice recognition. In some implementations, the server computing system 110 and the experiment computing system 170 can include their own input components or may share one or more input components with the client device 130, such that a user may be able to provide input for the experiment computing system 170 using the input devices 150 of the client computing device. Further, the client device 130 can have a display 146 for presenting information, such as providing a client interface for experiment building. The display 146 can be a visual display including a plurality of visual components for providing the graphical elements of the plate experiment interface to a user. The visual display can include a liquid crystal display (LCD), a light-emitting diode display (LED), a plasma display, an organic light-emitting diode display (OLED), and/or a cathode ray tube display (CRT).

The client device 130 can further include a graphics processing unit 152. Graphics processing unit 152 can be used by processor 132 to provide a plate experiment interface. In some embodiments, client device 130 performs any and all experiment builder interface.

The client device 130 can include a network interface 154 for communicating with server 110 over network 160. Network interface 154 can include any components or configuration suitable for communication with server 110 over network 160, including, for example, one or more ports, transmitters, wireless cards, controllers, physical layer components, or other items for communication according to any currently known or future developed communications protocol or technology.

The network 160 can be any type of communications network, such as a local area network (e.g., intranet), wide area network (e.g., Internet), or some combination thereof. The network 160 can also include a direct connection between a client device 130 and the server 110. In general, communication between the server 110 and a client device 130 can be carried via network interface using any type of wired and/or wireless connection, using a variety of communication protocols (e.g., TCP/IP, HTTP), encodings or formats (e.g., HTML, XML), and/or protection schemes (e.g., VPN, secure HTTP, SSL).

In some implementations, the network 160 can be used to transfer communication between the client computing device 130 and/or the server computing system 110 to the experiment computing system 170. The communications can be instructions 138 generated in response to an experiment being built. For example, the client computing device 130 may receive a plurality of user inputs via the user input component 150 to generate an experiment using the client interface 110. Instructions 138 can then be generated that can be interpreted by the experiment computing system 170 to run an experiment. Moreover, in some implementations, the instructions 138 can be processed by the one or more processors 172 of the experiment computing system 170 in order to understand the instructions. The instructions can be saved to memory or interpreted into a more native format for the experimentation equipment. The experiment computing system can further include memory components 174 for locally storing data 176 and instructions 178. The stored data 176 can include data specific to one or more experiment instruments including device limitations, capabilities, and logs. In some implementations, the stored data 176 can include past instructions, information necessary for interpretation, and/or localized models. The stored instructions 178 can include predetermined functions, user-generated functions, and/or trained functions for various tasks the experiment computing system can complete. For example, the stored instructions 178 can include a plurality of instructions for processing experiments built with the client interface 120 and completing experiment set-up actions based on the experiment built with the client interface 120.

In some implementations, one or more non-transitory computer readable media that collectively store instructions that, when executed by the one or more processors, cause the experiment computing system to perform operations can be included in the computing system. In some implementations, the memory components of the client computing device 130, the server computing system 110, and the experiment computing system 170 can include the one or more non-transitory computer readable media. The stored instructions can include instructions that cause one or more of the computing systems to perform operations that can include the methods and processes disclosed herein.

Example Interface Arrangements

FIGS. 2A-2H depict illustrations of an example plate experiment interface 200 according to example embodiments of the present disclosure. In some implementations, the plate experiment interface 200 provides an interface for building an experiment and can include a plate map 214 representative of a plurality of samples or wells. Thus, in some implementations, the plate experiment interface 200 can include the plate map 214, a parameter column 212, and a groups column 216.

Figures 2A, 2B:
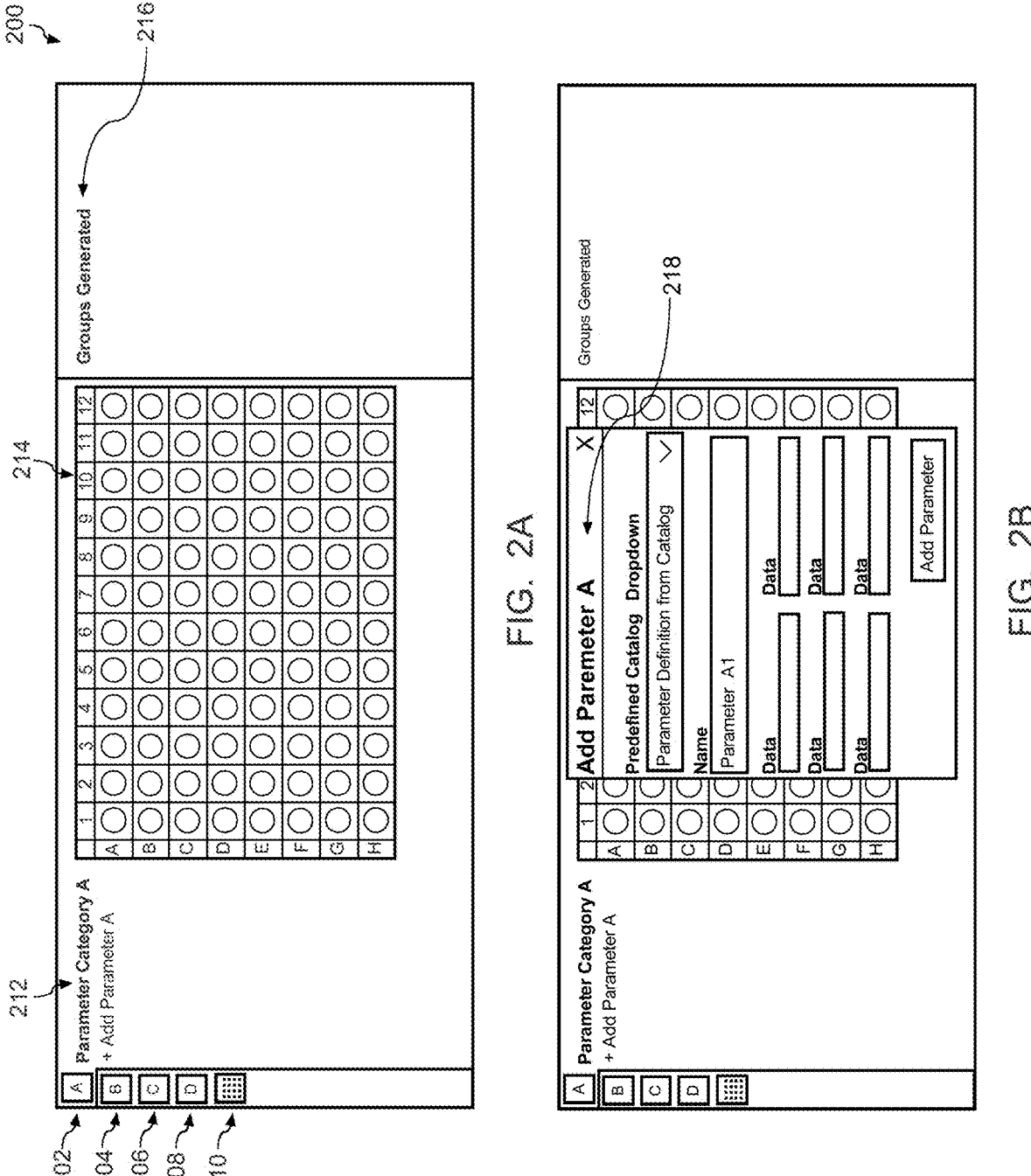
FIG. 2A depicts an illustration of an example experiment builder according to example embodiments of the present disclosure.
FIG. 2B depicts an illustration of an example parameter A configuration according to example embodiments of the present disclosure.

Specifically, FIG. 2A depicts a plate experiment interface 200 before any parameter settings have been assigned. In this implementation, the plate experiment interface includes a parameter column 212, a groups column 216, the plate map 214, four parameter tabs 202, 204, 206, & 208, and a finalization tab 210. The parameter tab selected in FIG. 2A is parameter tab A.

FIG. 2B depicts a parameter A pop-up menu 218. The parameter A pop-up menu 218 can be displayed in response to one or more inputs to add a new parameter A setting. In some implementations, the plate experiment interface 200 can include one or more predefined parameter settings for assignment. Additionally and/or alternatively, the plate experiment interface 200 can include one or more features that can allow a user to generate their own parameter settings for the experiment.

Figures 2C, 2D:
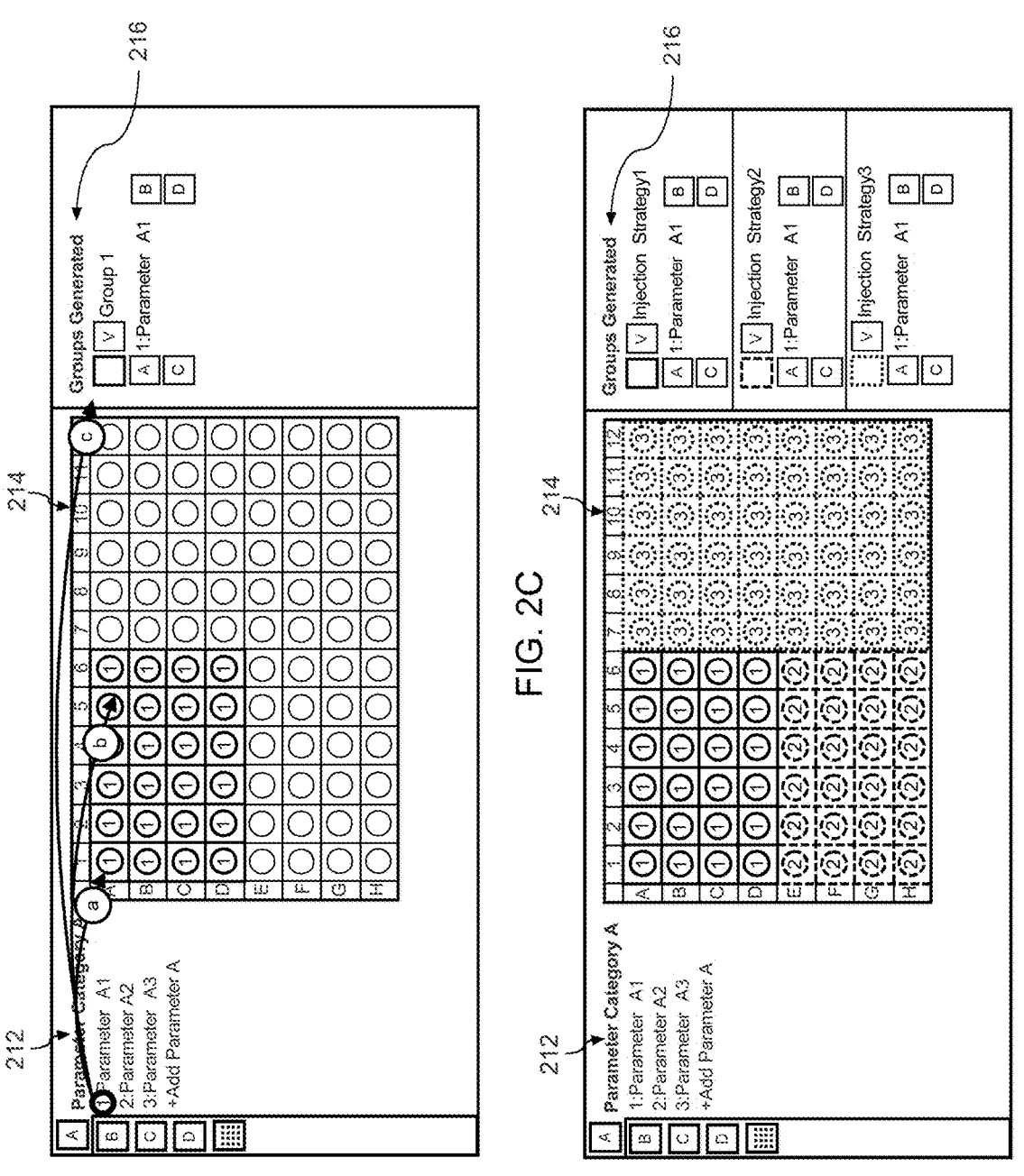
FIG. 2C depicts an illustration of an example parameter category A tab according to example embodiments of the present disclosure.
FIG. 2D depicts an illustration of an example parameter category A tab according to example embodiments of the present disclosure.

FIG. 2C depicts the assignment of a parameter A setting to a plurality of wells. In this implementation, the first parameter A setting is selected from the list in the parameter column 212, and then the plurality of cells on the plate map 214 representative of a plurality of wells are selected. The assignment can cause a first group to be generated and shown with an indicia indicative of the assigned parameter setting. In this implementation, group information for the new group is provided in the groups column 216.

FIG. 2D depicts the plate map 214 after two other parameter settings in the parameter column 212 are assigned to wells. Two more groups can be generated in the groups column 216 in response to the new assignments. In some implementations, the groups can be automatically generated in response to the new assignments.

Figures 2E, 2F:
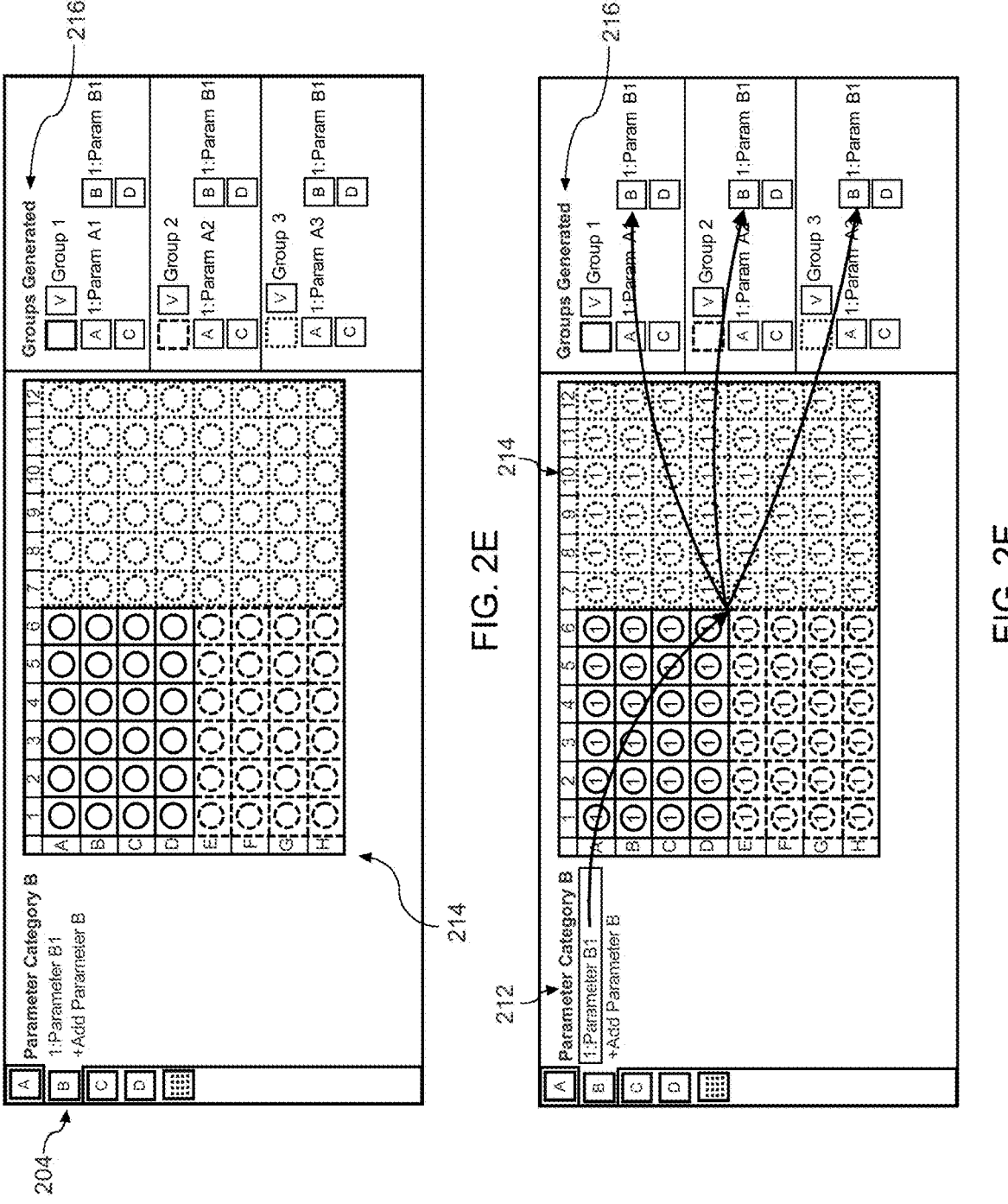
FIG. 2E depicts an illustration of an example parameter category B tab according to example embodiments of the present disclosure.
FIG. 2F depicts an illustration of an example parameter category B tab according to example embodiments of the present disclosure.

FIG. 2E depicts the example plate experiment interface 200 after the parameter B tab 204 is selected. The numerical indicia can be removed from the plate map 214 to indicate that no parameters of the B type have been assigned. The color indicia indicative of the groups can remain and may continue to be described by the information in the groups column 216. In some implementations, the plate experiment interface 200 indicia updates can occur automatically in response to the parameter tab selection.

In FIG. 2F, a parameter B type parameter setting is assigned to a plurality of wells. The selected cells representative of the wells are then filled with a number indicative of the parameter setting. The group information in the groups column 216 can be updated in response to the assignments.

Figure 2G:
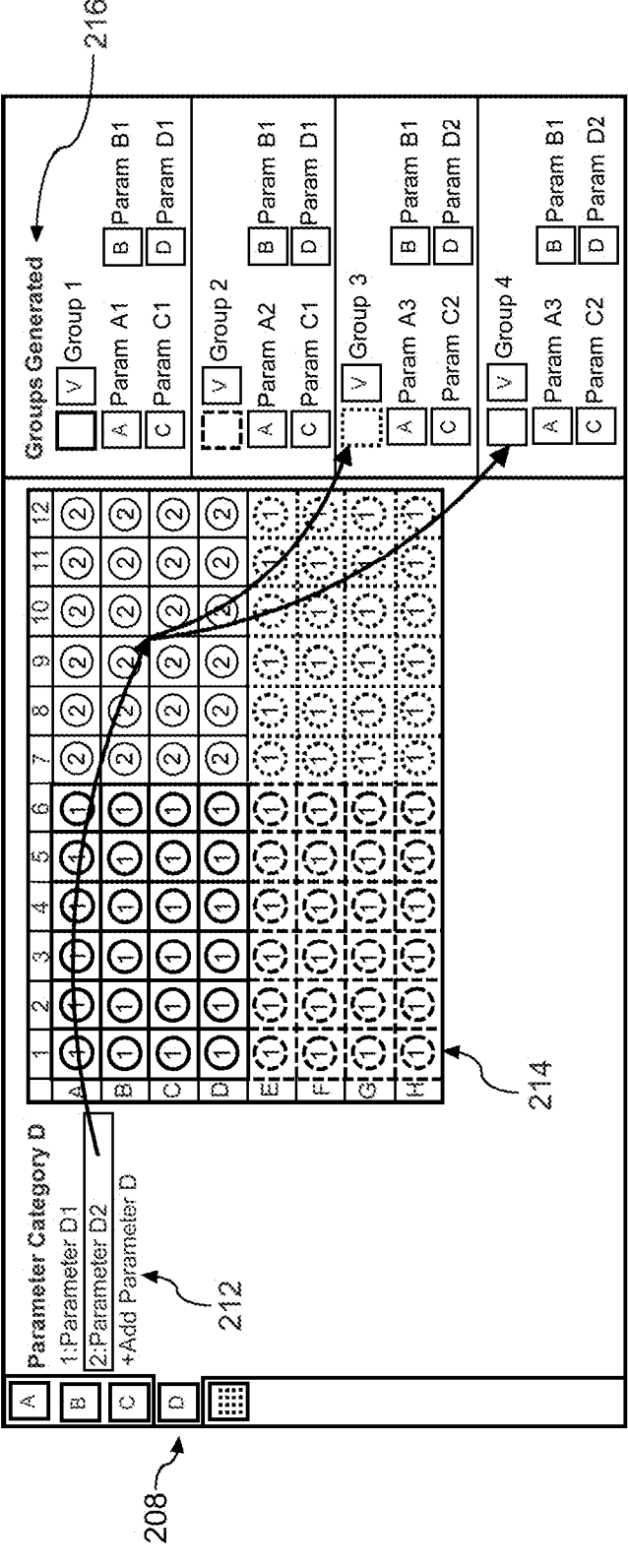
FIG. 2G depicts an illustration of an example parameter category D tab according to example embodiments of the present disclosure.

Moreover, FIG. 2G depicts the assignment of parameter D type parameter settings to a plurality of wells, which caused new groups to form through the subdivision of the current groups with the updated groups and group information being provided in the groups column 216. In some implementations, the new groups may be automatically generated in response to the assignment.

Figure 2H:
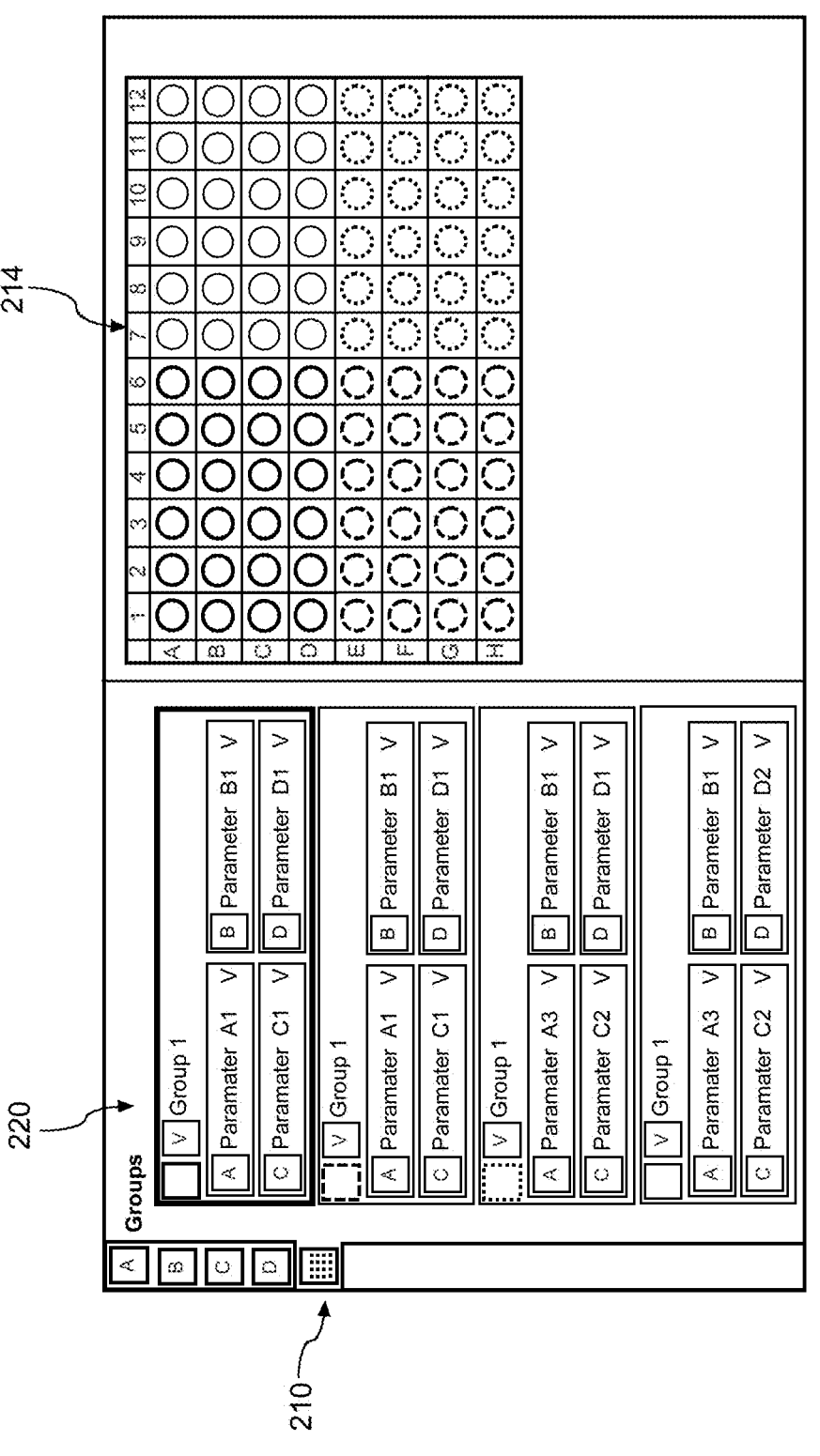
FIG. 2H depicts an illustration of an example finalization tab according to example embodiments of the present disclosure.

Lastly, FIG. 2H depicts the example plate experiment interface 200, when the finalization tab 210 is selected. In the finalization page, the plate map 214 can be provided with different indicia that may be descriptive of the different groups. The finalization page can also include a new groups column 220 that can provide for group editing, indicia editing, or the creation of new groups.

Figures 3A, 3B:
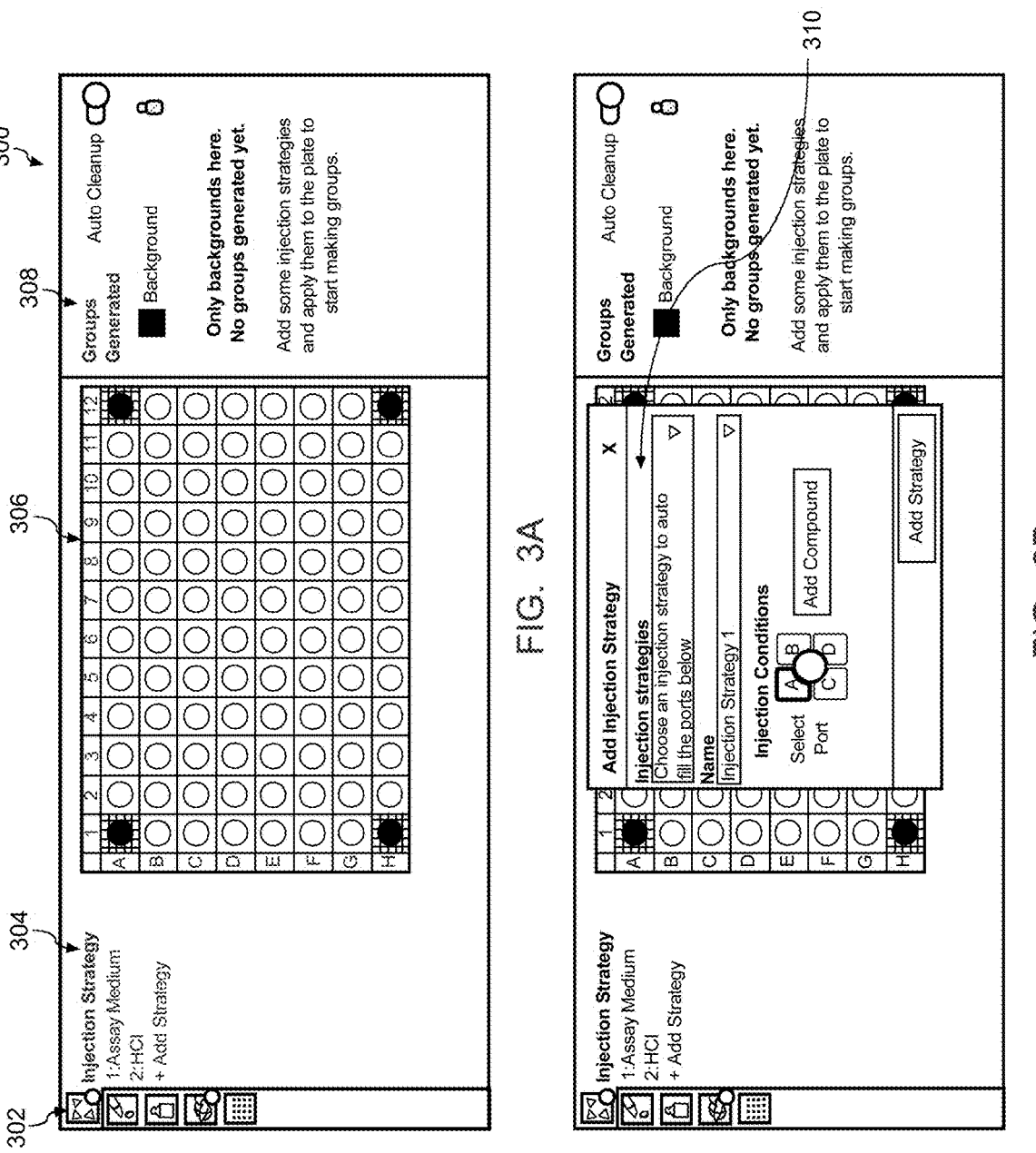
FIG. 3A depicts an illustration of an example plate assay builder according to example embodiments of the present disclosure.
FIG. 3B depicts an illustration of an example injection strategy parameter configuration according to example embodiments of the present disclosure.
Figure 3C:
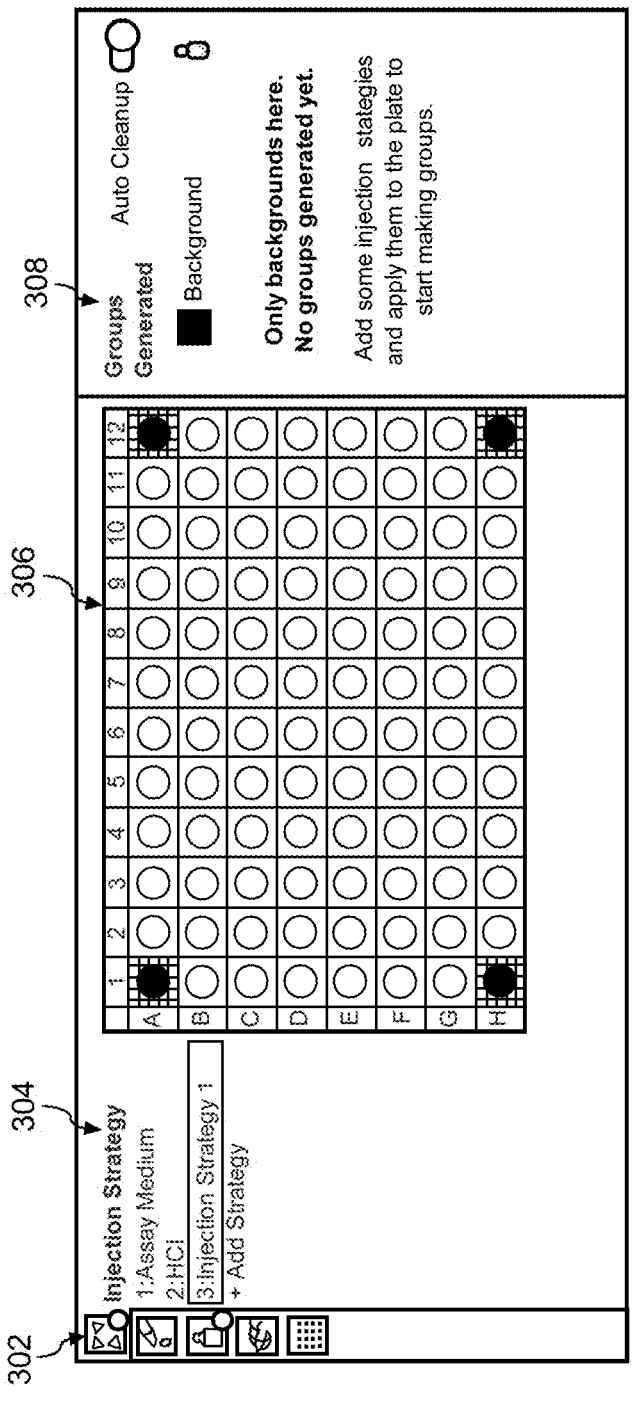
FIG. 3C depicts an illustration of an example injection strategy tab according to example embodiments of the present disclosure.
Figure 3D:
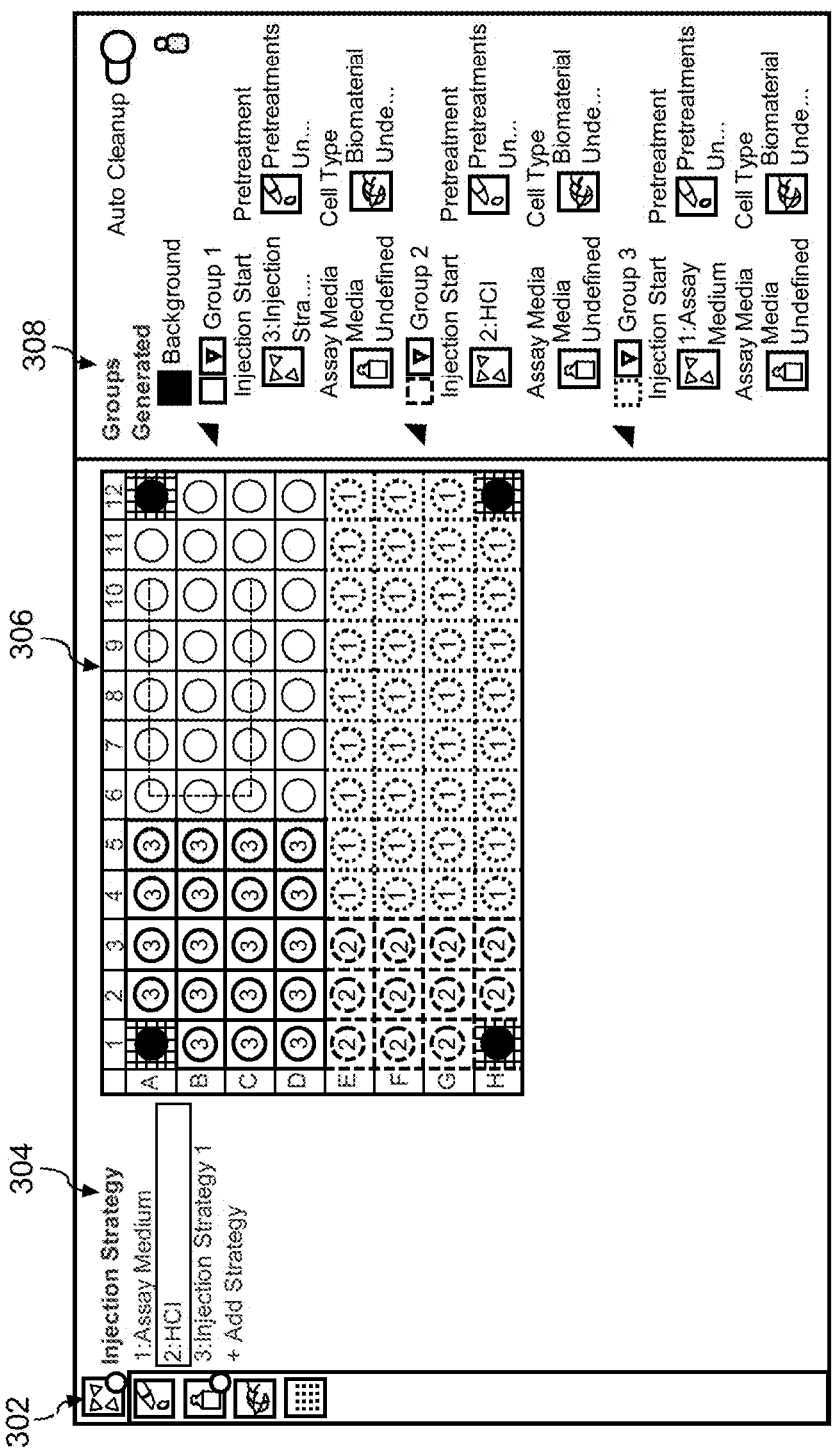
FIG. 3D depicts an illustration of an example injection strategy tab according to example embodiments of the present disclosure.
Figure 3E:
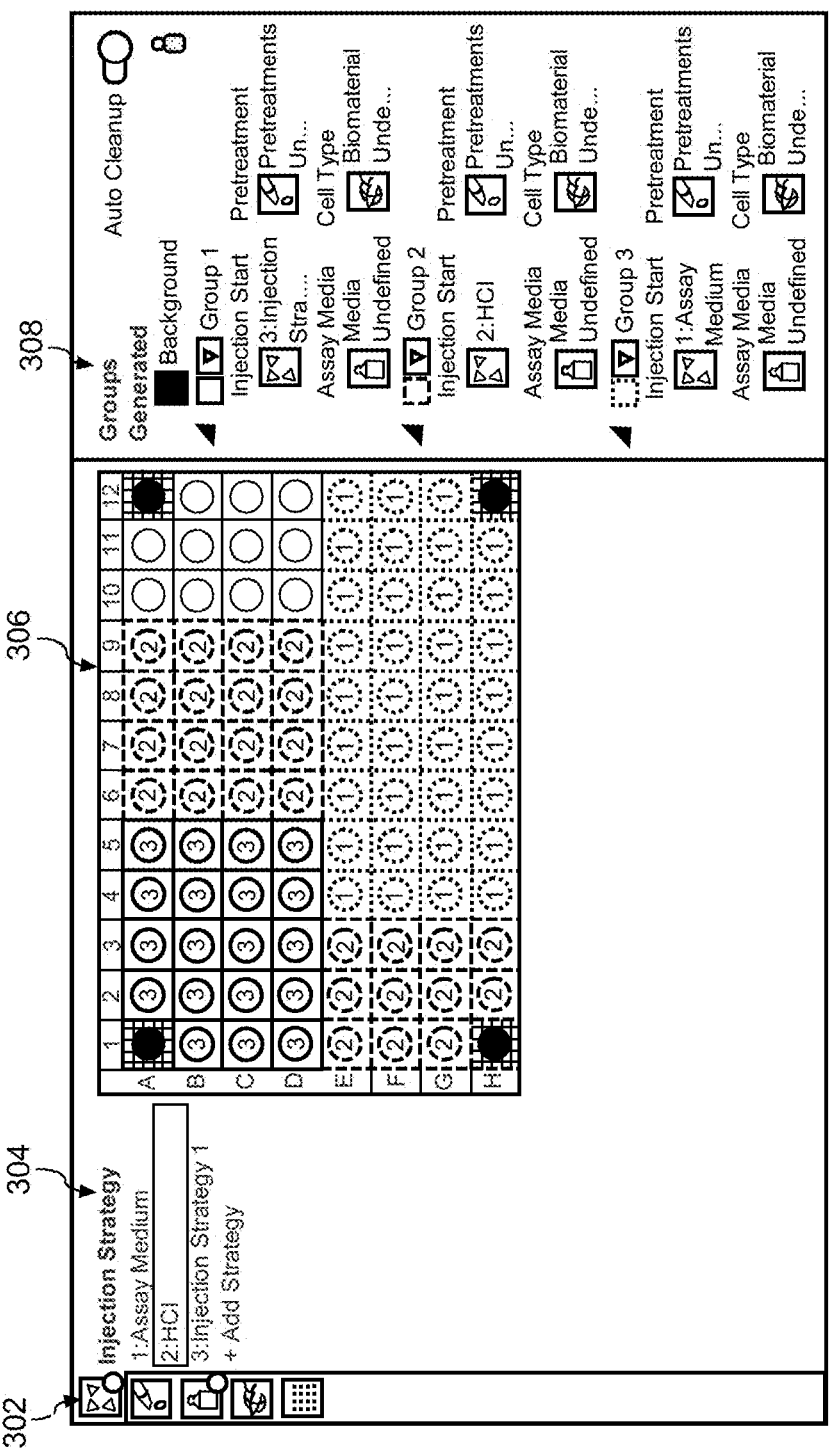
FIG. 3E depicts an illustration of an example injection strategy tab according to example embodiments of the present disclosure.
Figure 3F:
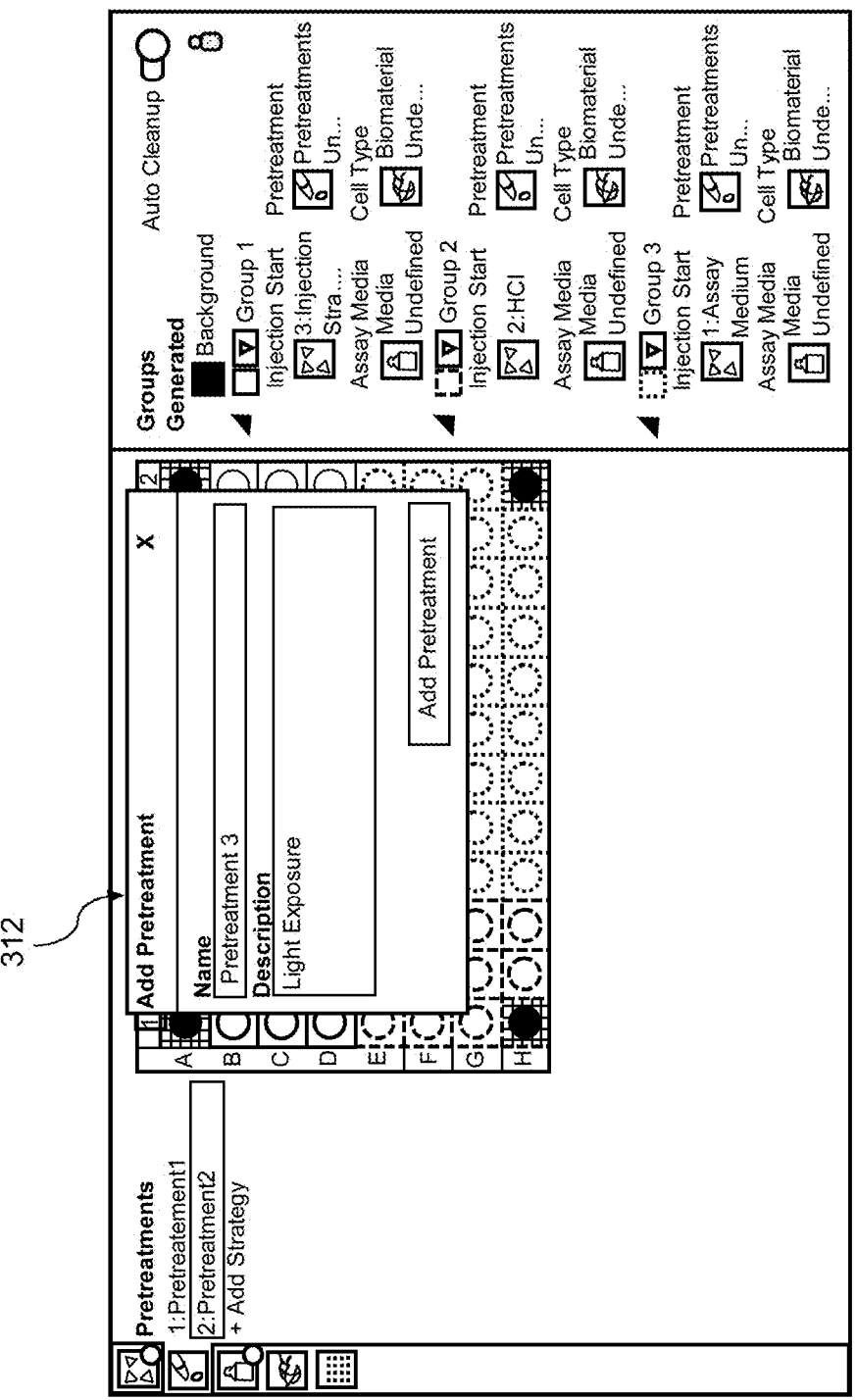
FIG. 3F depicts an illustration of an example pretreatment parameter configuration according to example embodiments of the present disclosure.
Figure 3G:
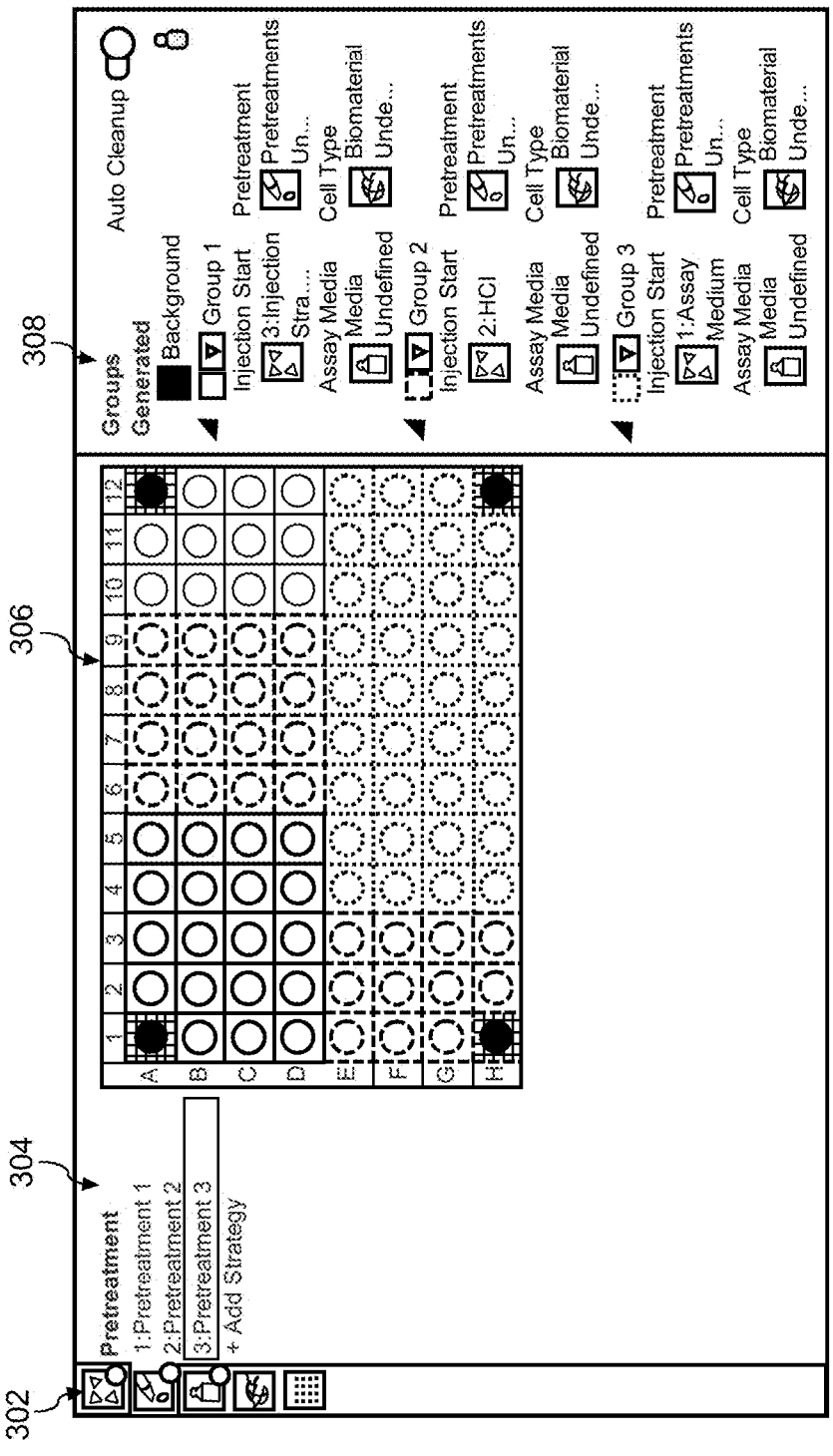
FIG. 3G depicts an illustration of an example pretreatments tab according to example embodiments of the present disclosure.
Figure 3H:
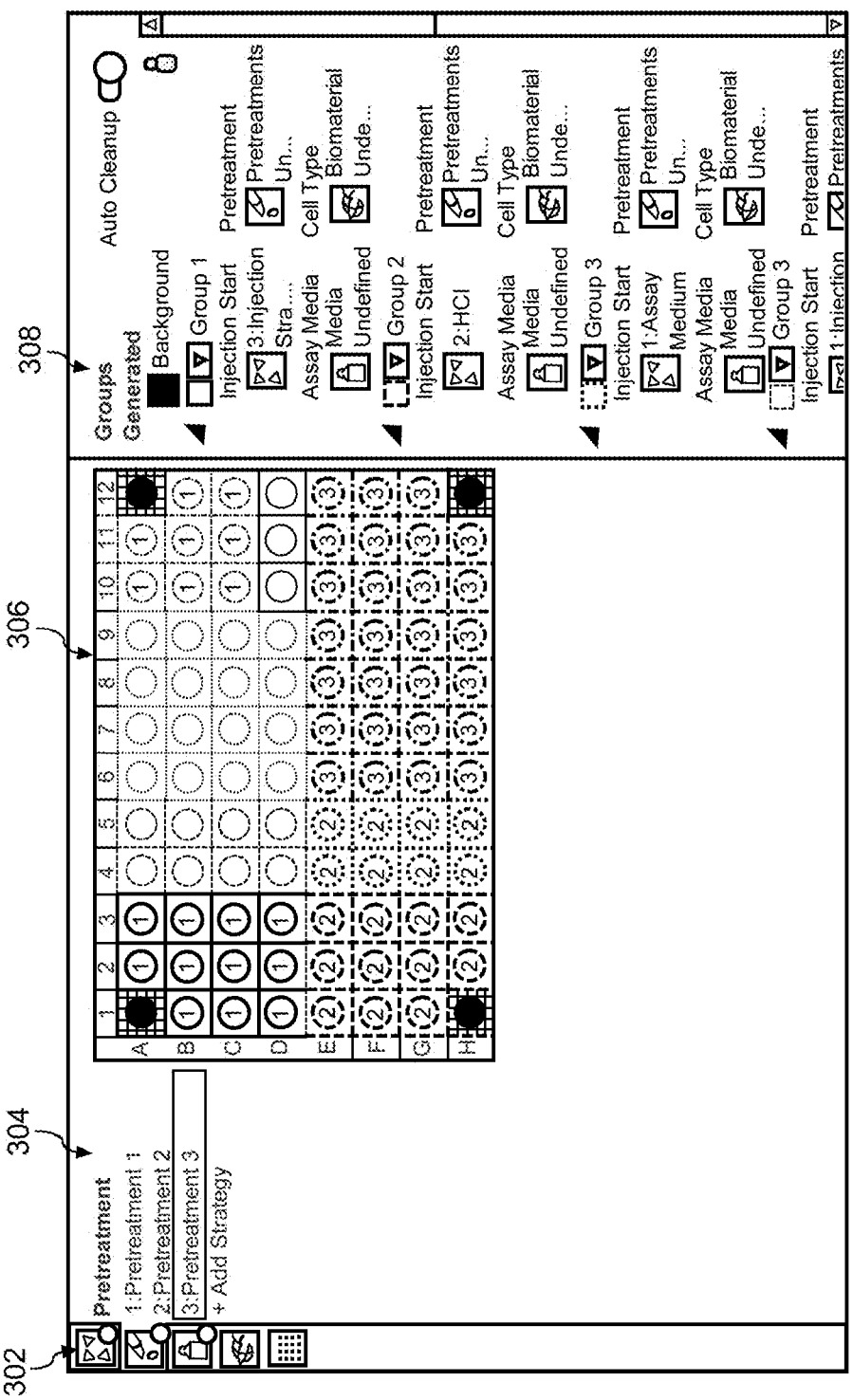
FIG. 3H depicts an illustration of an example pretreatments tab according to example embodiments of the present disclosure.
Figure 31:
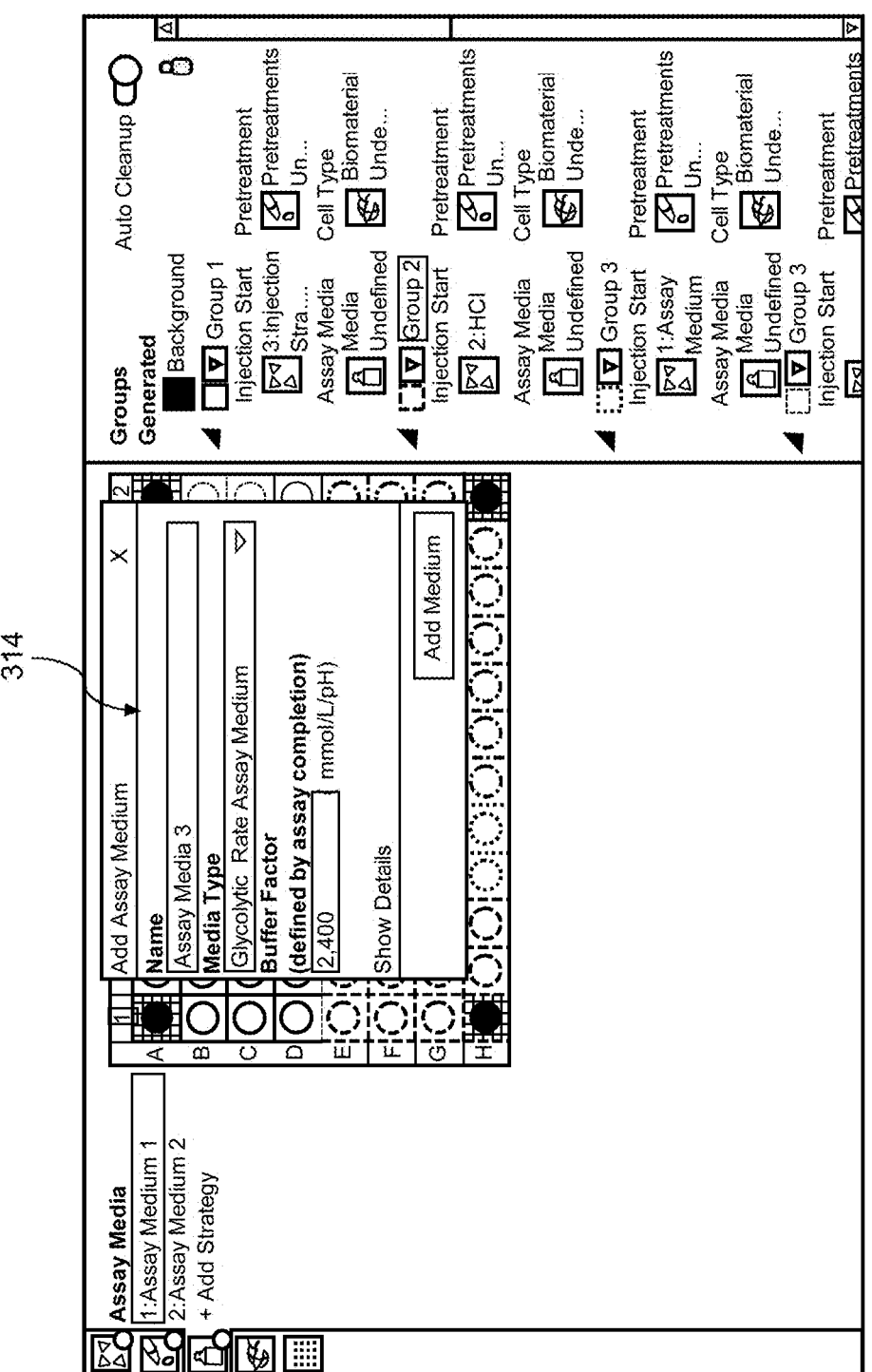
Figure 3J:
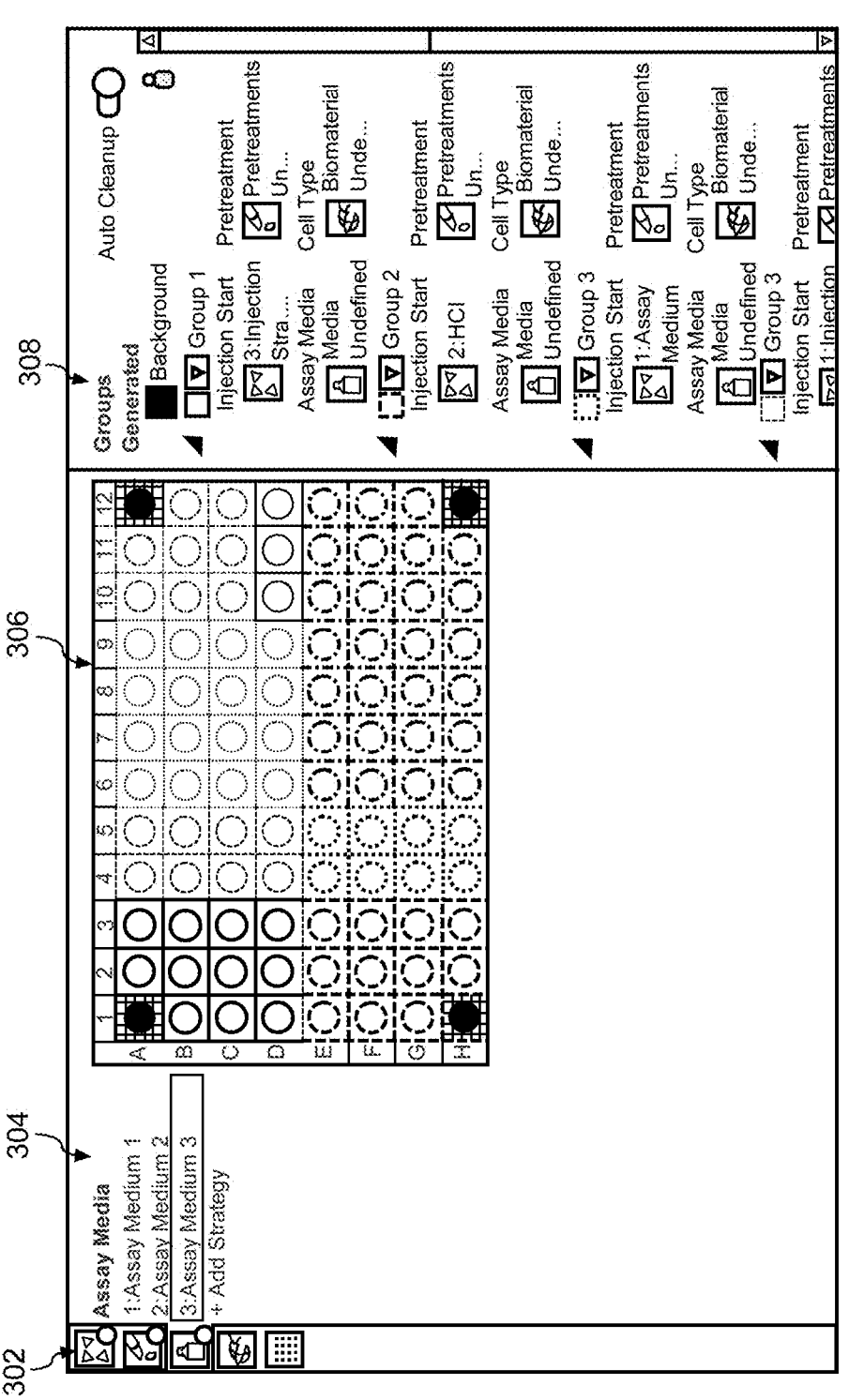
FIG. 3J depicts an illustration of an example assay media tab according to example embodiments of the present disclosure.
Figure 3K:
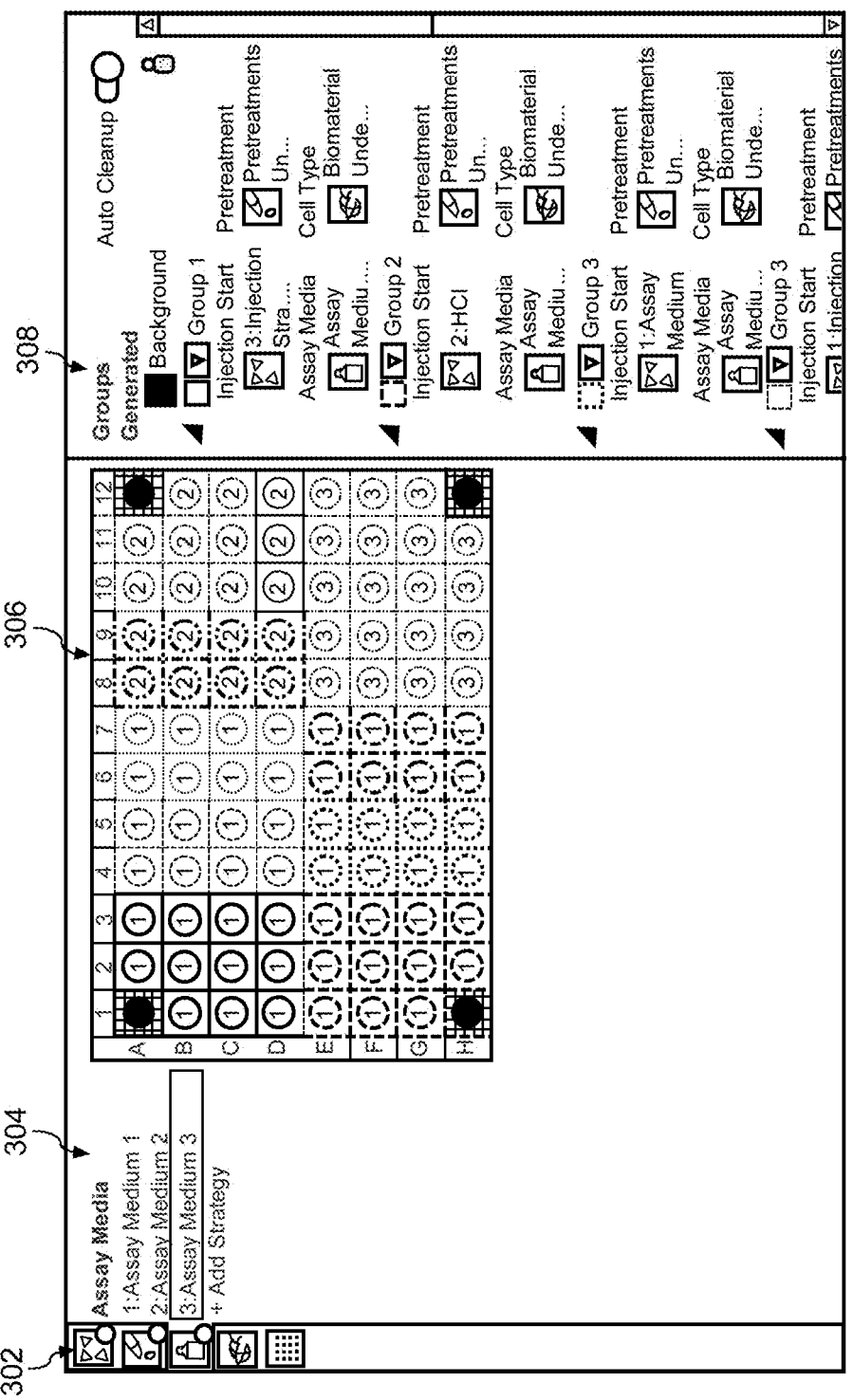
FIG. 3K depicts an illustration of an example assay media tab according to example embodiments of the present disclosure.
Figure 3L:
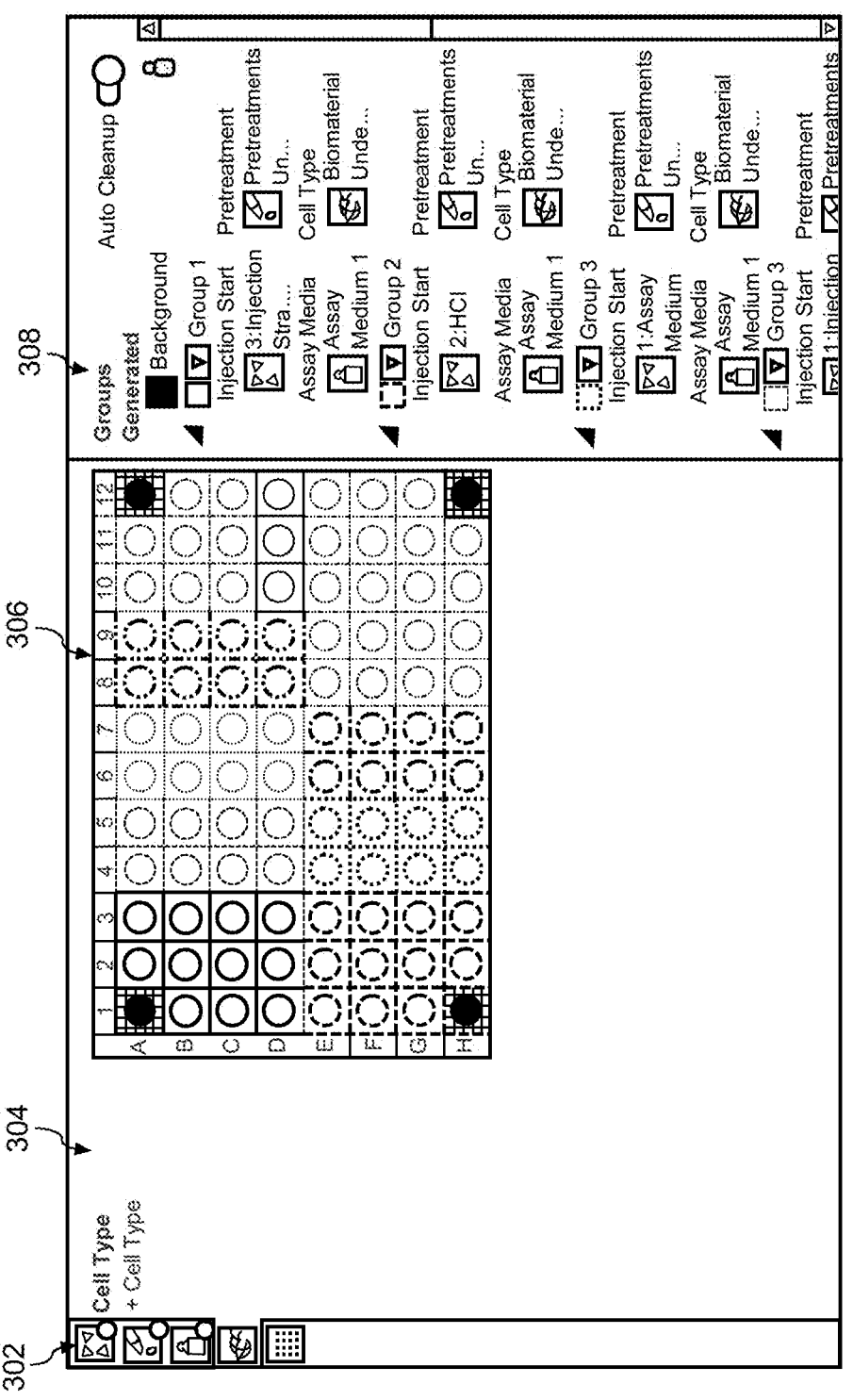
FIG. 3L depicts an illustration of an example cell type tab according to example embodiments of the present disclosure.
Figure 3M:
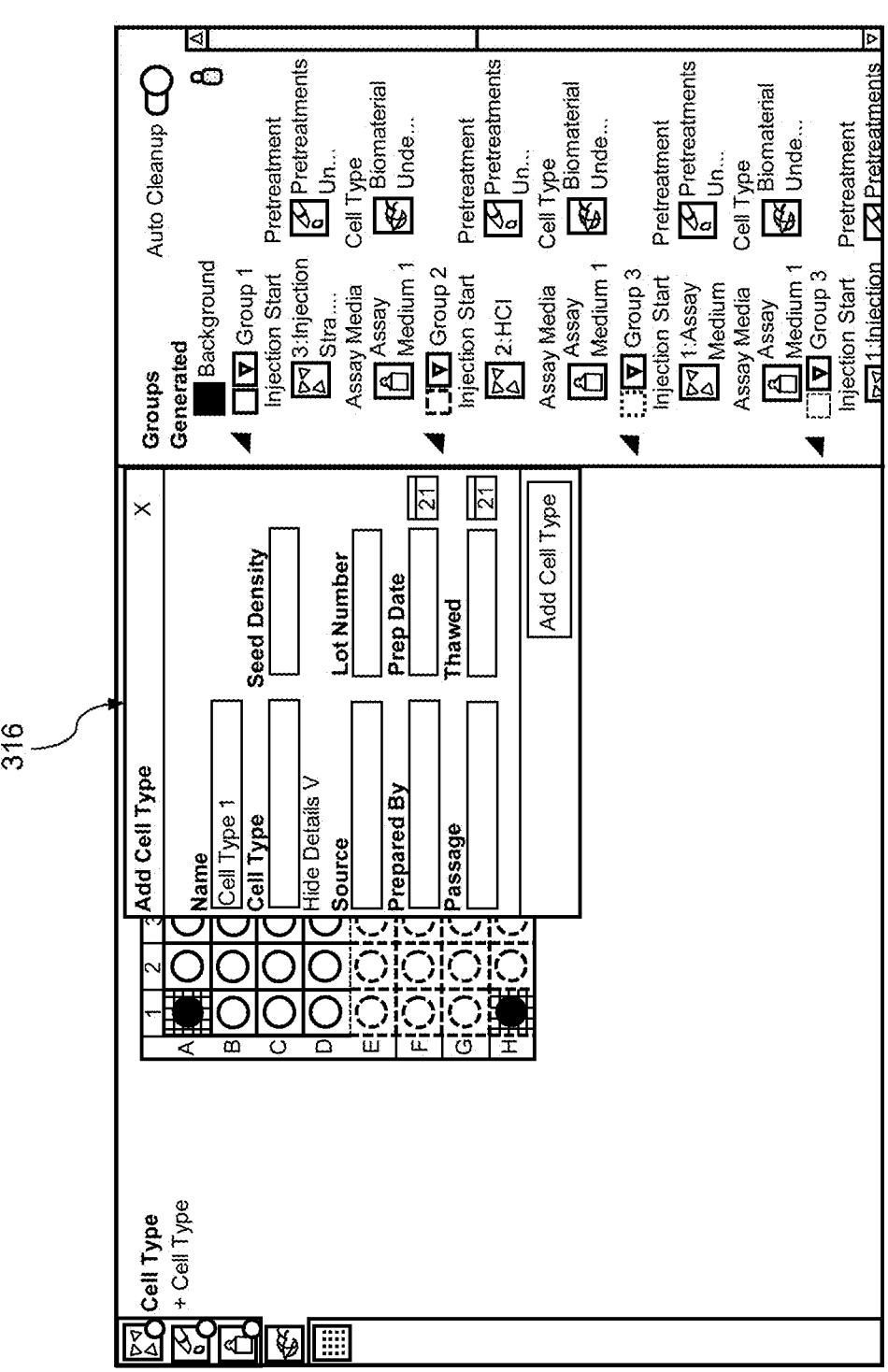
FIG. 3M depicts an illustration of an example cell type parameter configuration according to example embodiments of the present disclosure.
Figure 3N:
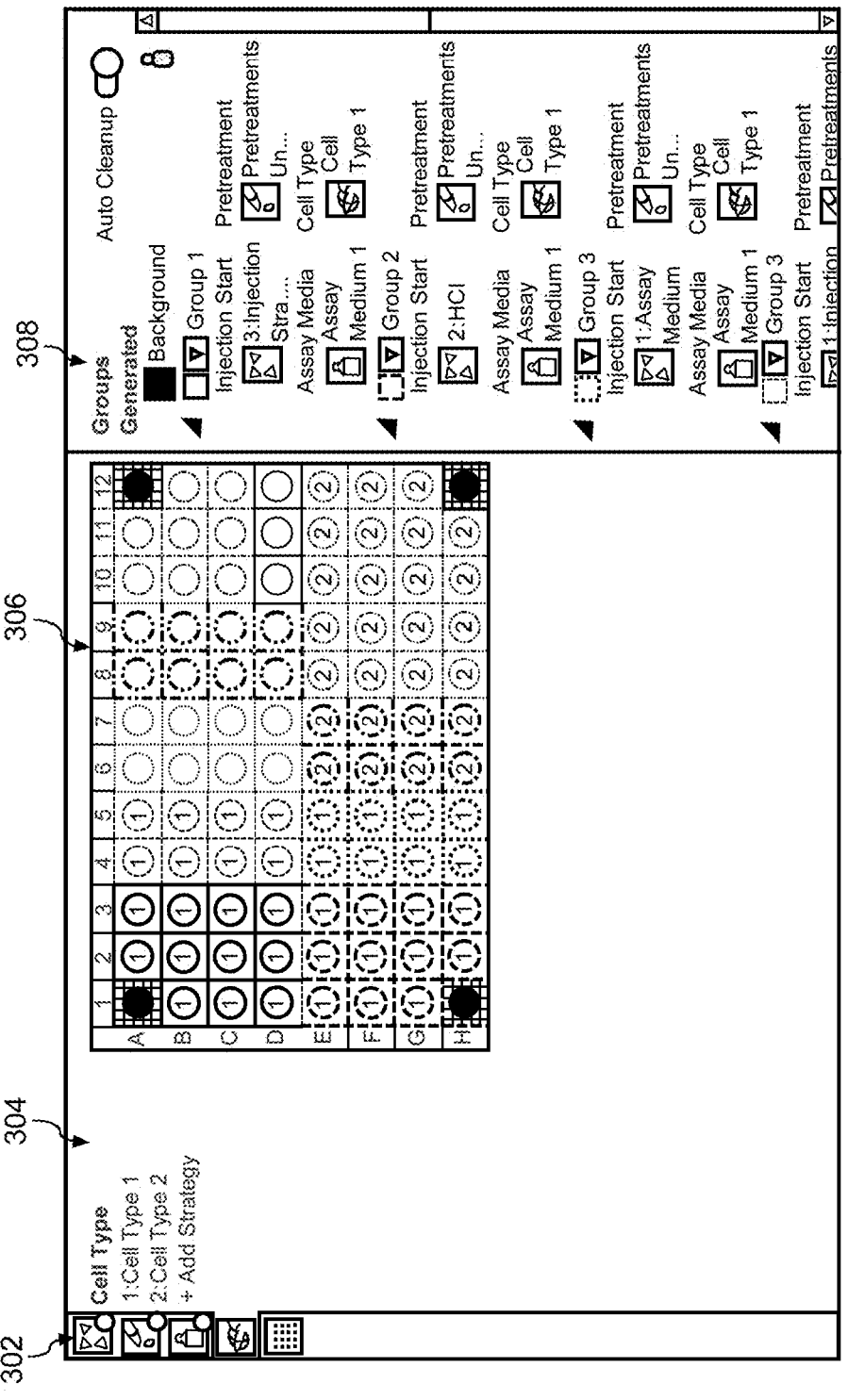
FIG. 3N depicts an illustration of an example cell type tab according to example embodiments of the present disclosure.
Figure 30:
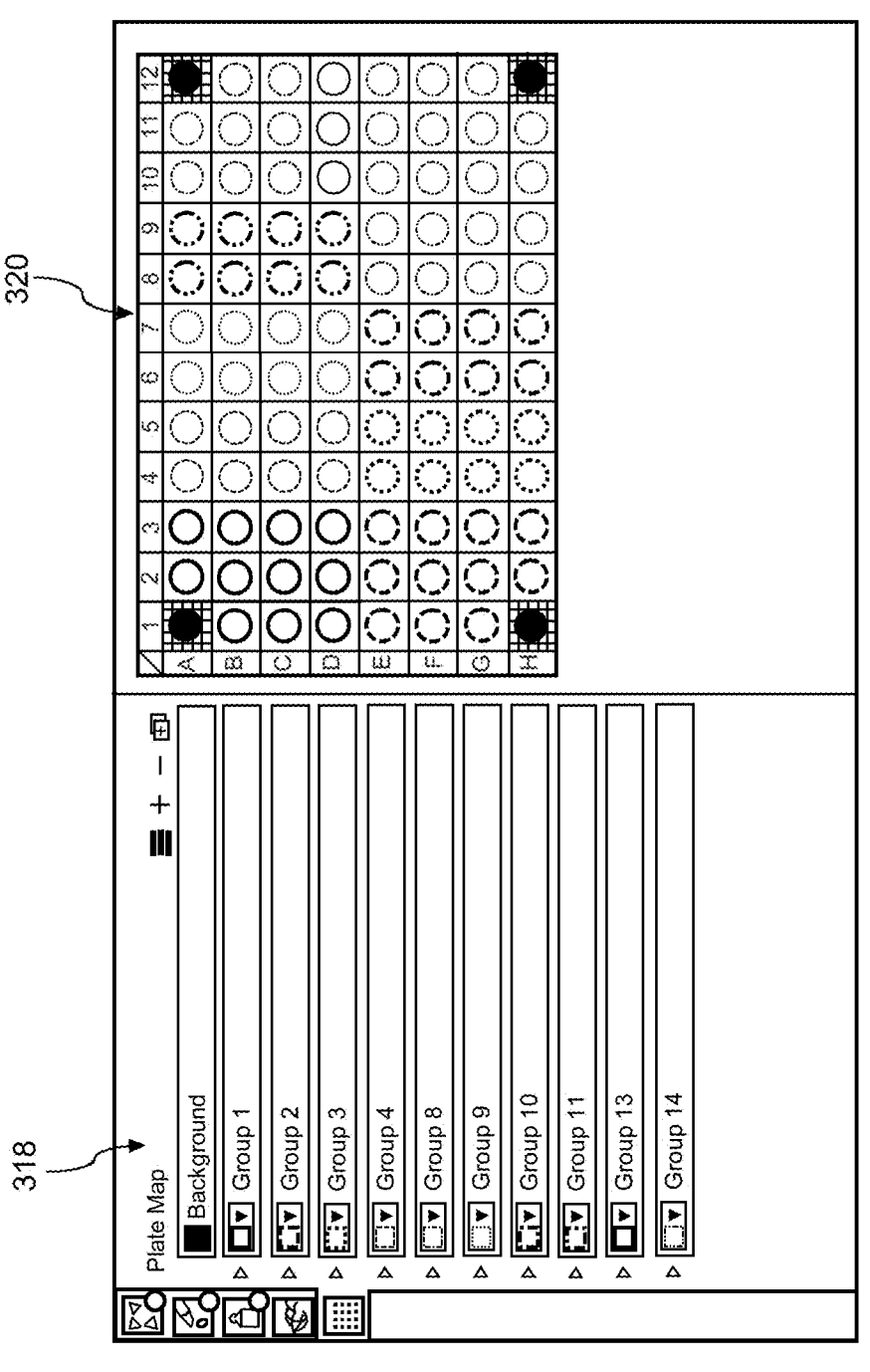
Figure 3P:
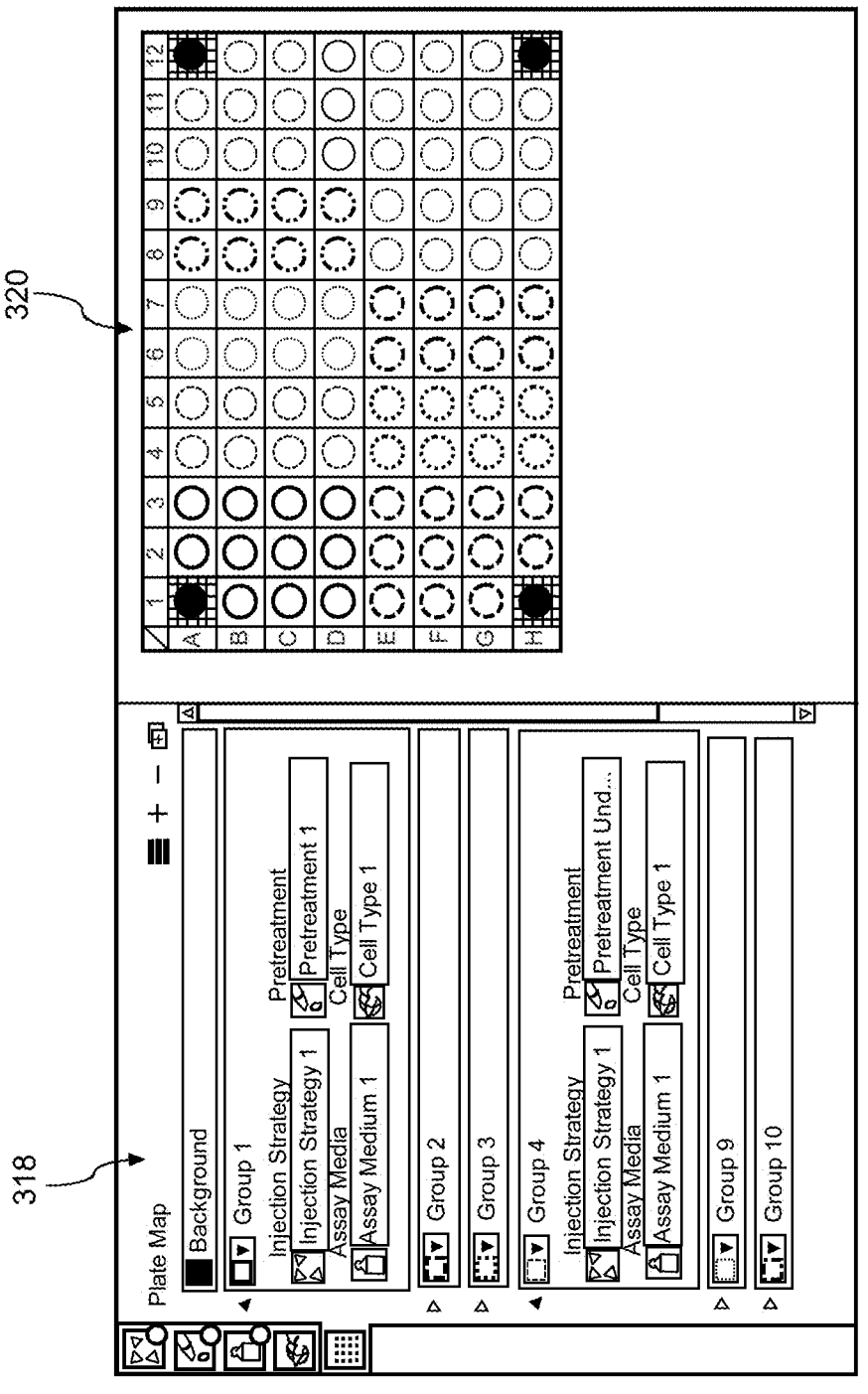
FIG. 3P depicts an illustration of an example finalization tab according to example embodiments of the present disclosure.
Figure 3Q:
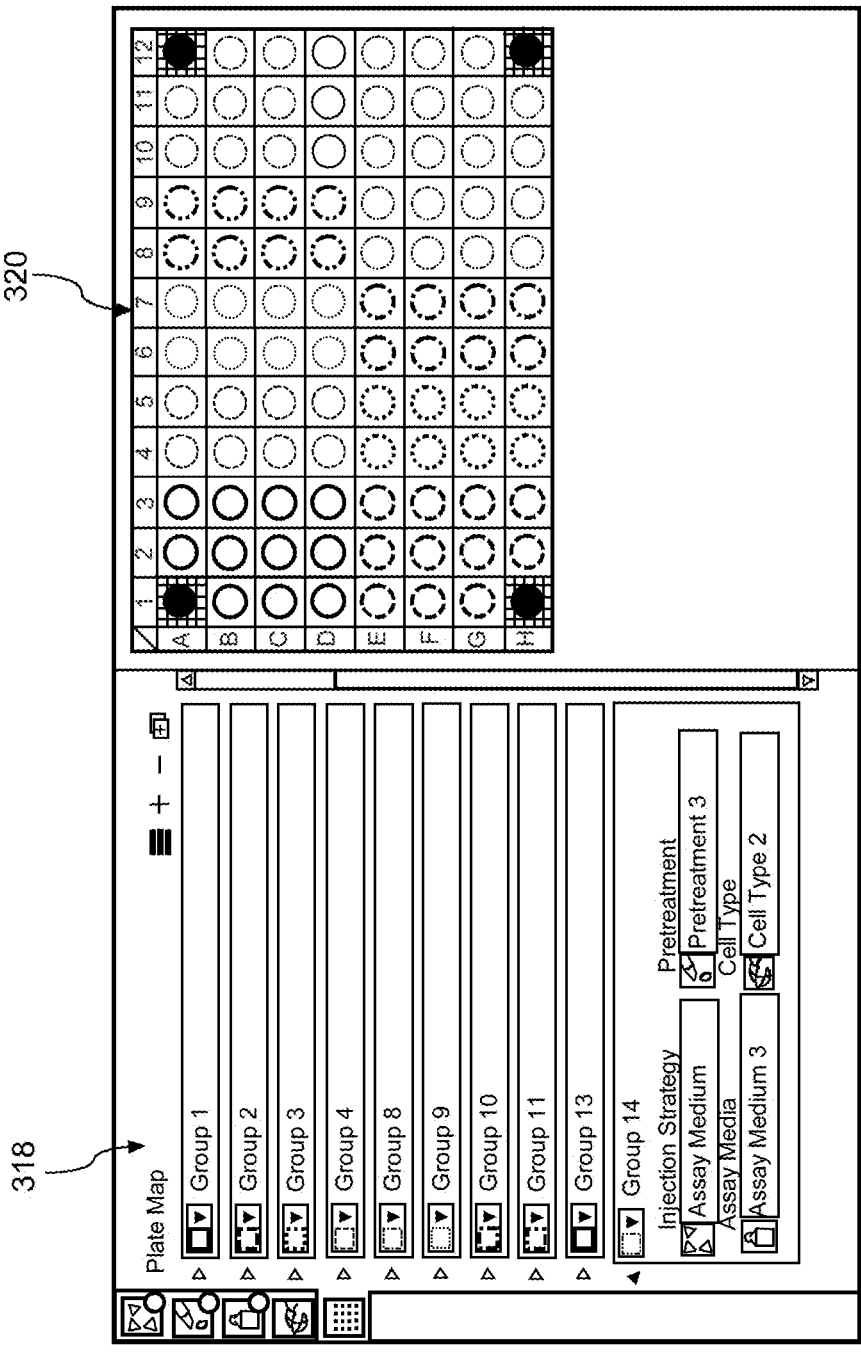
FIG. 3Q depicts an illustration of an example finalization tab according to example embodiments of the present disclosure.
Figure 3R:
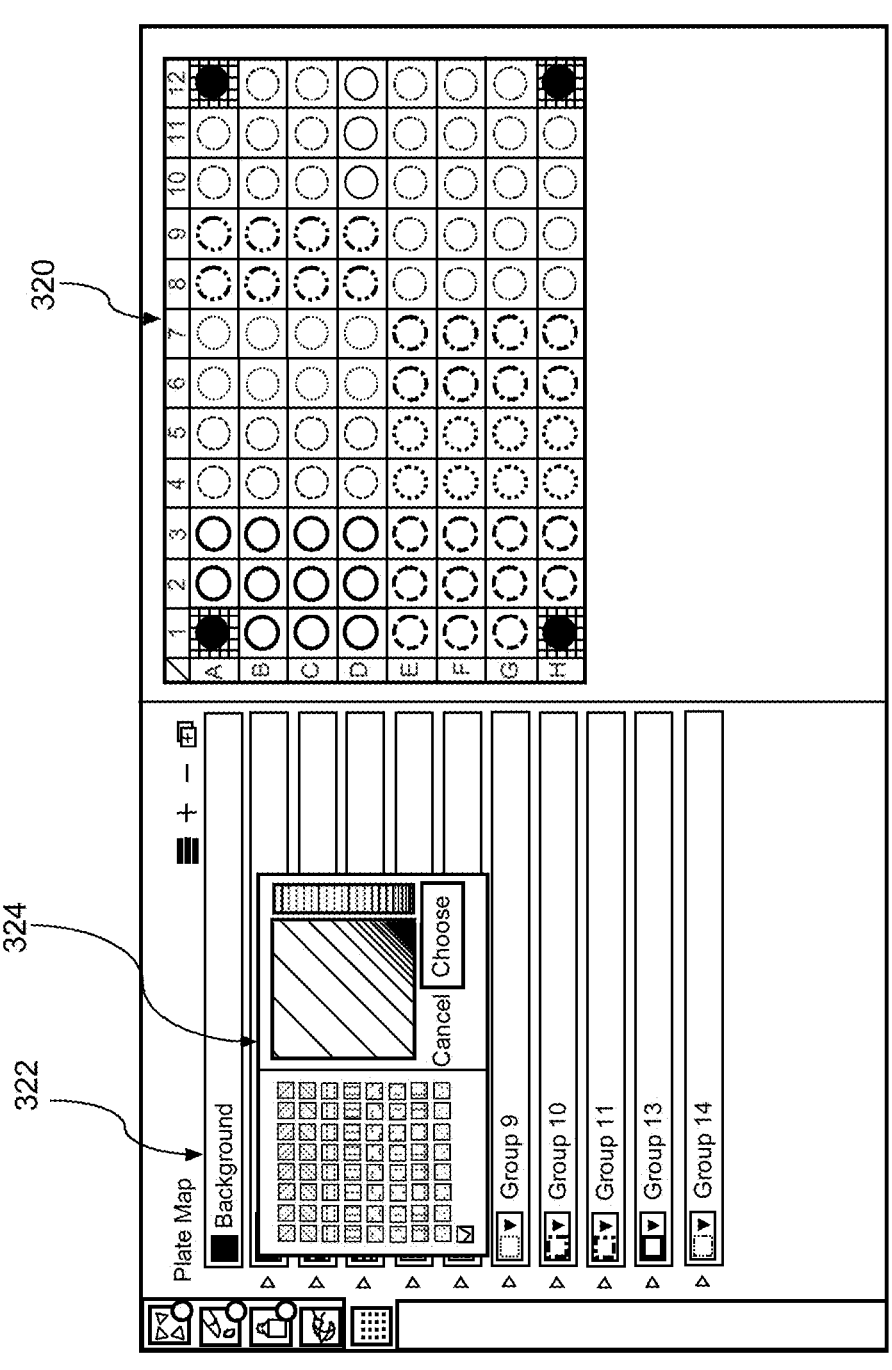
FIG. 3R depicts an illustration of an example indicia change according to example embodiments of the present disclosure.
Figure 3S:
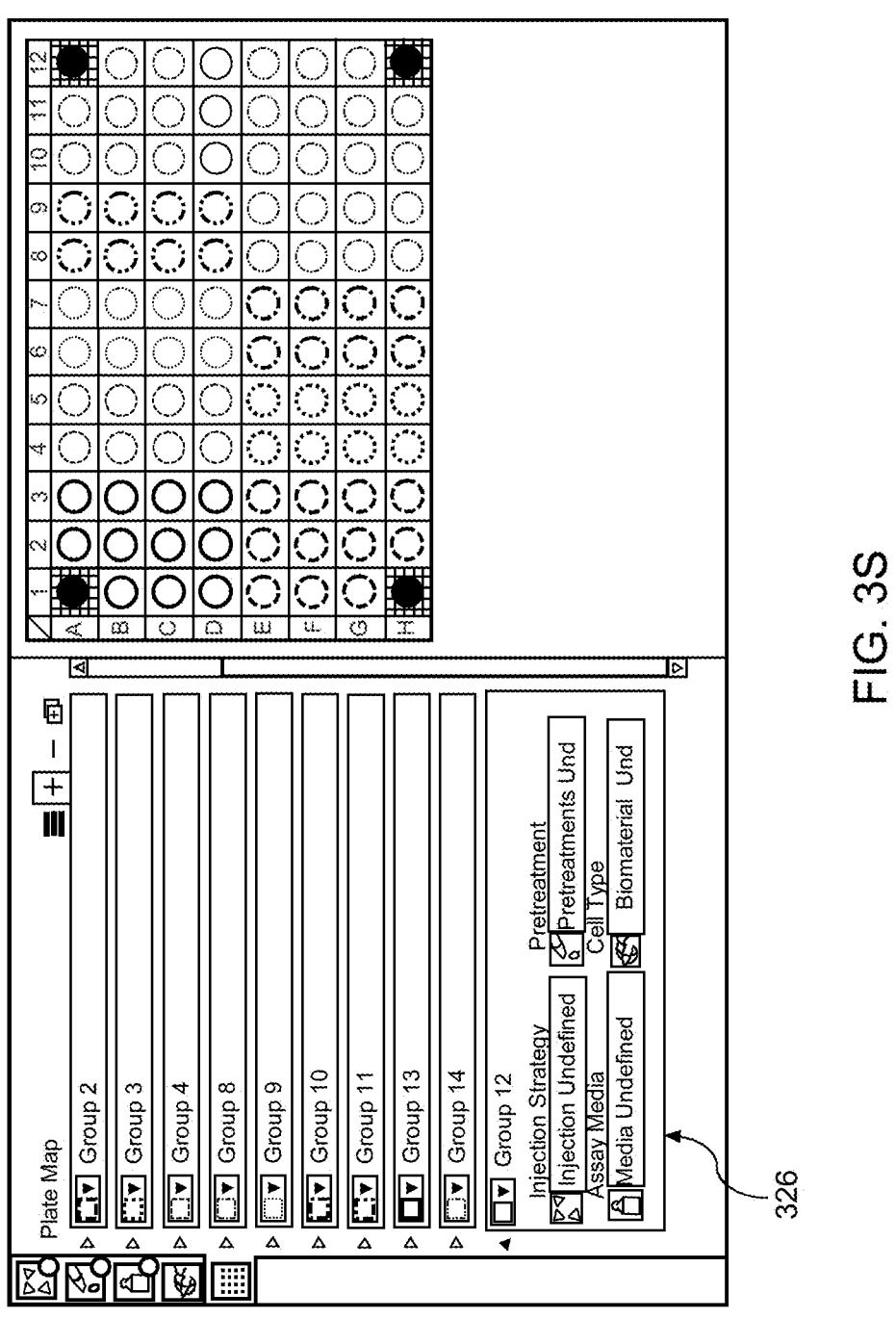
FIG. 3S depicts an illustration of an example finalization tab according to example embodiments of the present disclosure.
Figure 3T:
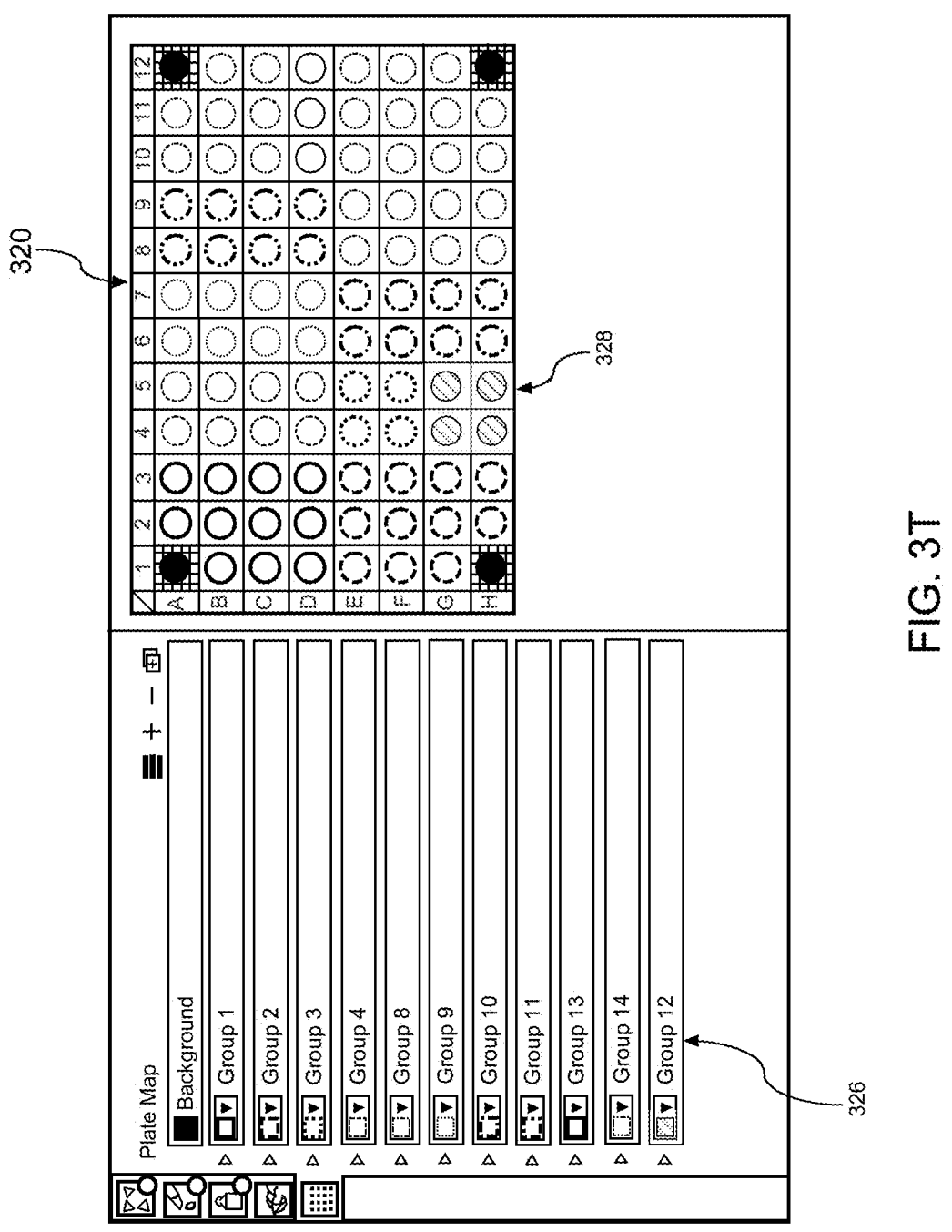
FIG. 3T depicts an illustration of an example finalization tab according to example embodiments of the present disclosure.

FIGS. 3A-3T depict block diagrams of an example plate experiment interface 300 according to example embodiments of the present disclosure. The plate experiment interface 300 is similar to plate experiment interface 200 of FIGS. 2A-2H except that plate experiment interface 300 is specifically configured for plate assay experiment building.

More specifically, the plate experiment interface 300 of FIGS. 3A-3T can include a plurality of tabs 302, a parameter column 304, a plate map 306, and a groups column 308. The plurality of tabs 302 can include an injection strategy tab, a pretreatment tab, an assay media tab, and a cell type tab to represent the four parameter types for the example plate assay experiment being built. Additionally and/or alternatively, the plurality of tabs 302 can include a finalization tab for reviewing and editing the generated groups.

The parameter column 304 can provide information on the different parameter settings for the parameter type currently being edited and assigned. The parameter settings can be pre-defined parameter settings, user-generated parameter settings, and/or auto-generated parameter settings. In some implementations, the parameter column 304 can include a selectable feature for adding a new parameter setting, which can cause a pop-up menu to be displayed.

The plate experiment interface 300 can also include a plate map 306 that can depict cells, or boxes, representative of different wells for the plate assay experiment. In the depicted illustrations, the plate map 306 includes four background cells that cannot be assigned parameters; however, in some implementations, the plate map 306 can have zero background cells or any number of background cells.

Additionally and/or alternatively, the plate experiment interface 300 can include a groups column 308 that can include each group generated along with an indicia indicating the wells in the group. The groups column 308 may also include information on the parameter settings for each group generated.

FIG. 3A depicts a blank plate map 306 before parameter assignment. The parameter column 304 includes two pre-defined parameter settings and a user generated parameter setting. The groups column 308 is currently empty as no parameter settings have been defined.

FIG. 3B depicts an example pop-up menu 310 for creating a new injection strategy parameter setting. The pop-up menu 310 can be configured to be specifically tailored for injection strategy parameter strategy creation. For example, four ports can be provided to represent the four injection ports in an injection instrument; however other port amounts can be provided for different injection instruments. Moreover, various strategy selections can cause a change in port options.

FIG. 3C depicts the parameter setting "injection strategy 1" being selected.

FIG. 3D depicts the plate map during injection strategy parameter setting assignment. More specifically, the depicted illustration includes each of the three parameter settings being assigned to a portion of the plate map 306 to generate three groups, which are indicated with different colors and described in the groups column 308. The assigned parameter setting can be indicated with numbers in the cells. Moreover, FIG. 3D shows a new portion of the plate map 306 being selected for parameter setting assignment via a click-and-drag gesture input. FIG. 3E depicts the selected cells being filled with indicia indicative of the parameter setting assignment and their new grouping.

Similar to FIG. 3B, FIG. 3F depicts an example pop-up menu 312 for creating a new parameter setting; however, the new parameter setting being added is a new pretreatment parameter setting. The pop-up menu 312 can be configured to be specifically tailored for pretreatment parameter creation. For example, the pop-up menu 312 can include drop-down menus specific for treatment or may include text boxes for text entry.

FIG. 3G and FIG. 3H depict the change in the plate map 306 and the groups column 308 as pretreatment parameter settings are assigned. For example, FIG. 3G includes no numerical indicia and the groups column 308 includes only three groups. In contrast, FIG. 3H includes "1," "2," and "3" throughout the plate map 306 to indicate the parameter setting assigned to those wells. In response to the parameter setting assignments, new groups can be generated, which can be described in the groups column 308 and indicated with differing colors.

Similar to FIG. 3B and FIG. 3F, FIG. 3I depicts an example pop-up menu 314 for creating a new parameter setting; however, the new parameter setting being added is a new assay media parameter setting. The pop-up menu 314 can be configured to be specifically tailored for assay media parameter creation. For example, the pop-up menu 314 can include drop-down menus specific for treatment or may include text boxes for text entry. Moreover, the pop-up menu 314 can include a media type drop-down selection and a buffer factor input section.

In FIG. 3J, the plate map 306 is depicted without numbers after the assay media parameter tab was selected. FIG. 3K depicts example assay media parameter setting assignments, which cause more groups to be generated in the groups column 308 and changes the indicia depicted in the plate map 306.

In FIG. 3L, the plate map 306 is depicted with the group indicia remaining from FIG. 3K, but the numerical indicia has once again been cleared as a new parameter tab has been selected.

Similar to FIGS. 3B, 3F, and 3I, FIG. 3M depicts an example pop-up menu 316 for creating a new parameter setting; however, the new parameter setting being added is a new cell type parameter setting. The pop-up menu 316 can be configured to be specifically tailored for cell type parameter creation. For example, the pop-up menu 316 can include drop-down menus specific for organic matter or may include text boxes for text entry. Moreover, the pop-up menu 316 can include a cell type drop-down selection.

In FIG. 3N, the plate map 306 includes new numerical indicia in response to one or more user inputs to assign cell type parameter settings to cells representing specific wells. One or more groups can be edited or created in response to the user inputs.

FIGS. 3O-3T depict the finalization interface of the example plate experiment interface 300. The finalization interface can include a plate map 320 with one or more group indicia and a groups column 318 that includes group information for the one or more groups. For example, the groups column 318 can include a legend that indicates which indicia is associated with which group. While interacting with the finalization interface, groups can be reviewed, edited, and/or created. For example, as depicted in FIGS. 3P and 3Q, the parameter settings of each group can be reviewed and edited in the groups column 318.

FIG. 3R depicts the adjustment of the indicia 322 of a first group using a pop-up color palette 324. In response to the user-initiated indicia adjustment, the plate map 320 can be updated to reflect the new indicia.

FIGS. 3S and 3T depict an example user interaction to create and assign a new group using the finalization interface. Figure S depicts a "Group 12" 326 being generated after the "+" icon is selected. The user can then use the dropdown menus to select parameter settings for each parameter type. "Group 12" 326 can then be assigned to one or more cells 328 representative of one or more wells. In response to the assignment, the one or more cells 328 can change color, as shown in FIG. 3T.

Figure 4A:
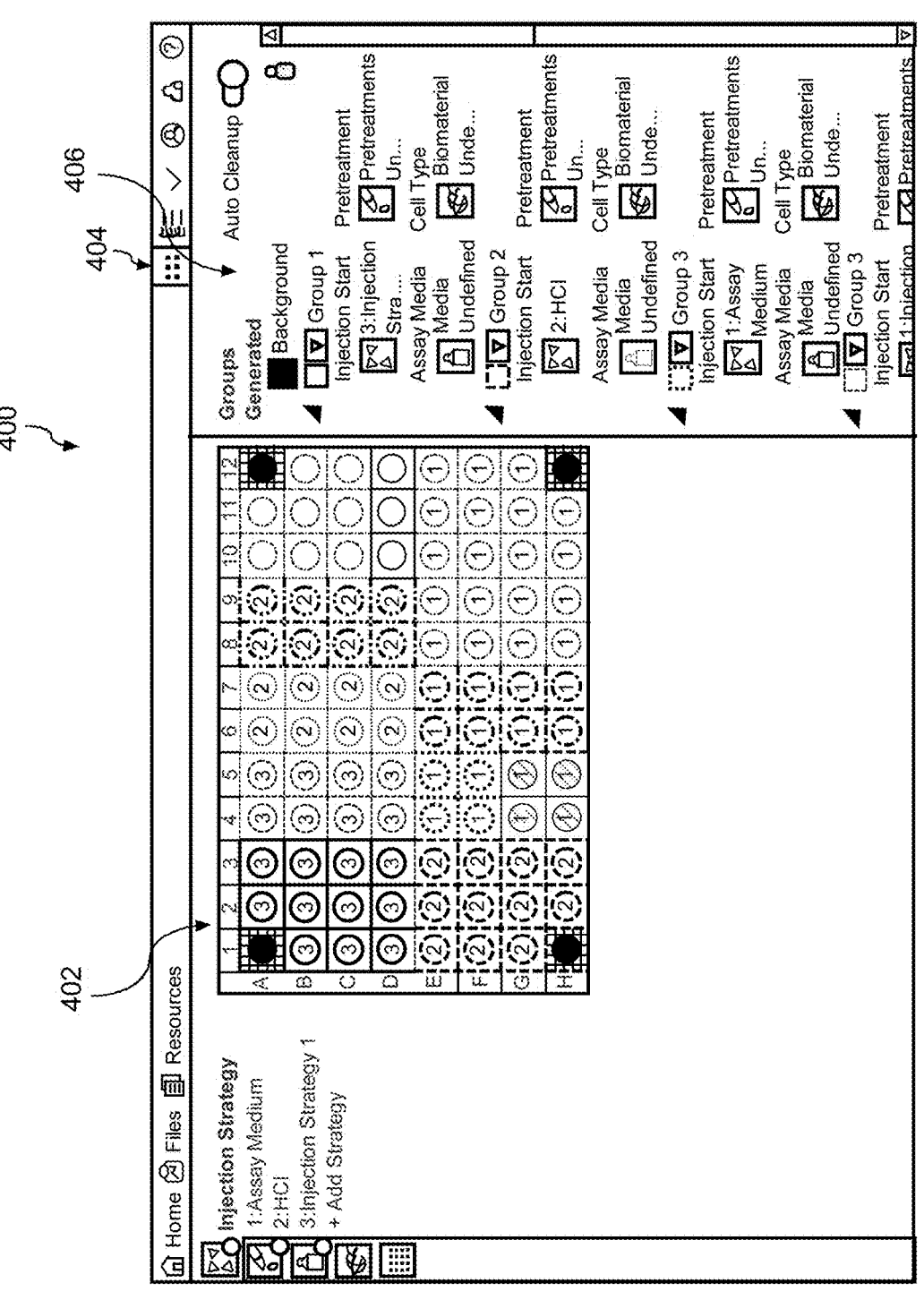
FIG. 4A depicts an illustration of an example experiment builder page according to example embodiments of the present disclosure.
Figure 4B:
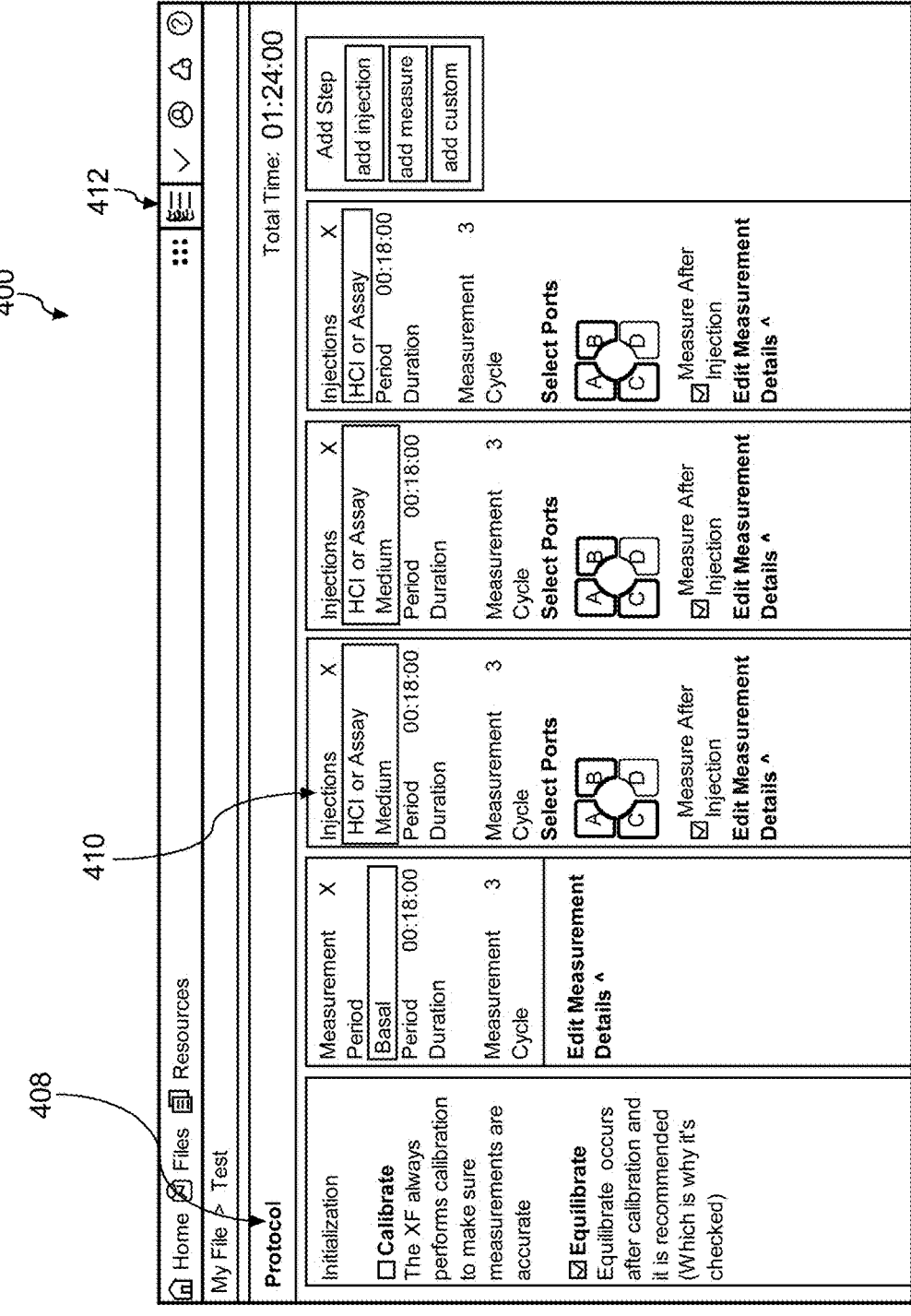
FIG. 4B depicts an illustration of an example protocol page according to example embodiments of the present disclosure.
Figure 4C:
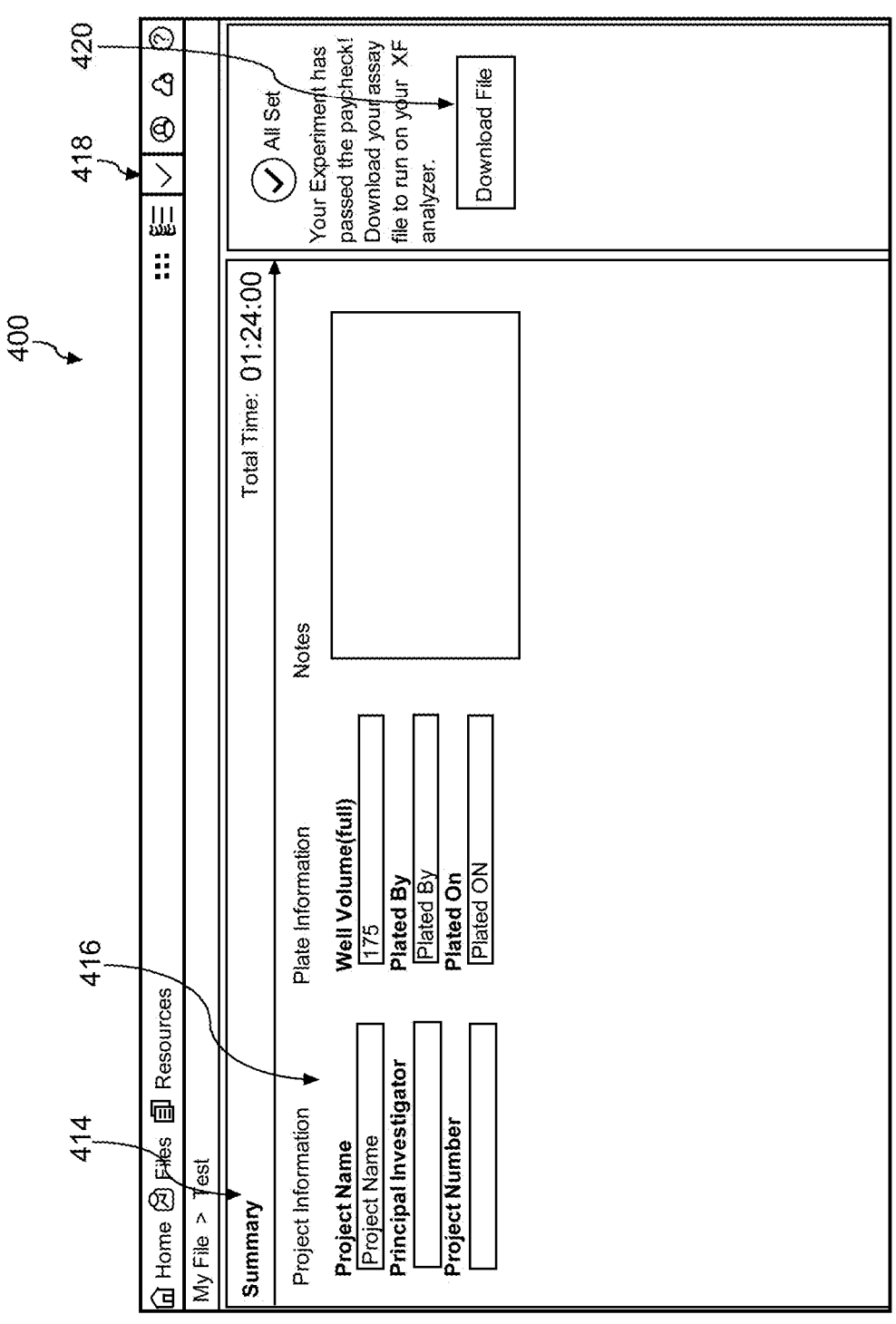
FIG. 4C depicts an illustration of an example download page according to example embodiments of the present disclosure.

FIGS. 4A-4C depict different features of an example plate experiment interface 400 including a plate experiment builder page in FIG. 4A, a protocol page in FIG. 4B, and a download page in FIG. 4C. In some implementations, each page can be provided in the depicted order in order to build an experiment with the plate experiment builder interface, to edit the protocols while on the protocol page, and to download the experiment information on the download page.

FIG. 4A depicts an example experiment builder page including a plate map 402 and one or more generated groups described in the groups column 406. In some implementations, the experiment builder page can be selected by selecting an experiment builder icon 404. In the depicted illustration, a plate experiment has already been built using the plate experiment interface. Moreover, in the depicted example, the injection strategy tab is opened to display possible injection strategy parameters along with the assigned parameter for each well which is depicted in the plate map 402 using numbers. The plate map 402 can also be descriptive of groups generated in response to parameter assignments. For example, the plate map 402 depicts multiple wells with numbers descriptive of the same parameter but different colors. The different colors can be due to other parameters assigned under different parameter types correlating with the different parameter tabs. Once the experiment is built, a user can move on to the protocol page depicted in FIG. 4B.

FIG. 4B depicts an example protocol page including a protocol overview 408. The protocol overview can include information descriptive of different protocols relevant for the experiment based on the experiment type or parameters assigned. In some implementations, certain parameters or protocols may be editable on the protocol page. For example, one or more of the injection strategies 410 may be depicted and editable on the protocol page. In some implementations, the protocol page can be accessed by selecting a protocol icon 412. Once the protocols are reviewed and finalized, a user may move to the download page depicted in FIG. 4C.

FIG. 4C depicts an example download page reached by selecting a download page icon 418. The download page can include a summary pane 414 for inputting in or reviewing summary information such as project information 416, which can include a project name. Once the summary information, the experiment build, and the protocol information are finalized, the user can select the download file graphical button 420 to download a file that can include the parameter information selected and assigned while interacting with the plate experiment interface. Additionally and/or alternatively, the file may include the protocol information and the experiment summary. The downloaded file can then be viewed for reference, uploaded to an experiment computing system to run the experiment, and/or printed for reference.

Figure 5:
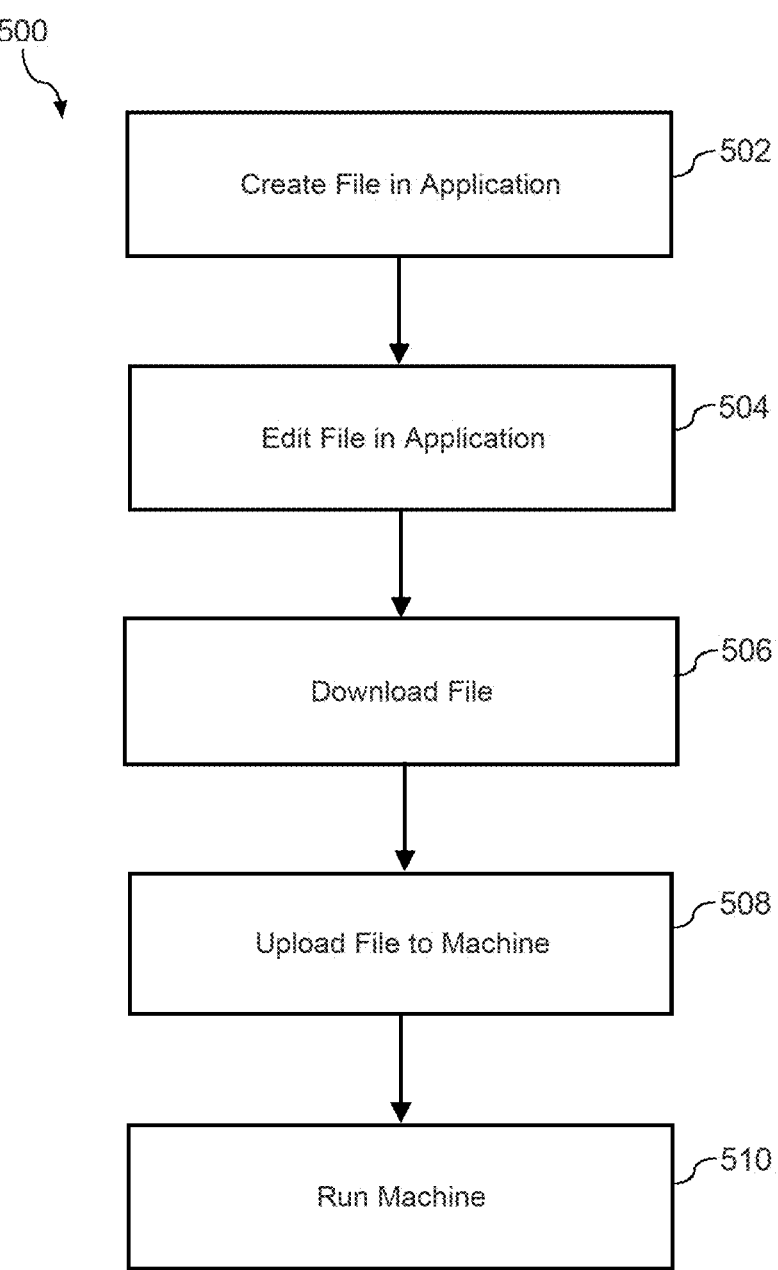
FIG. 5 depicts a block diagram of an example process to leverage the experiment builder to perform an experiment according to example embodiments of the present disclosure.

FIG. 5 depicts an example block diagram of an example process to leverage the experiment builder to perform an experiment. The systems and methods disclosed herein can utilize a plate experiment builder in order to intuitively build an experiment. The experiment can then be used to perform an experiment. For example, a user can create an experiment file with the plate experiment builder application 502. The file can be edited 504 inside the application to fine tune the experiment to the desired user parameters. The file can then be downloaded 506 upon finalization of the built experiment. The downloaded file can then be uploaded 508 to a machine used for one or more of the experimentation steps. For example, the downloaded file can be uploaded to an injection instrument in order to follow the injection strategy parameters selected by the user. Additionally and/or alternatively, the downloaded file may be uploaded to a pretreatment instrument or any other machine to complete another selected experiment parameter. Once uploaded, the experiment computing system can process the uploaded file to provide instructions to the one or more machines to run 510 the experiment. The machines can then be used to run the experiment built in the plate experiment builder application.

Figure 14A:
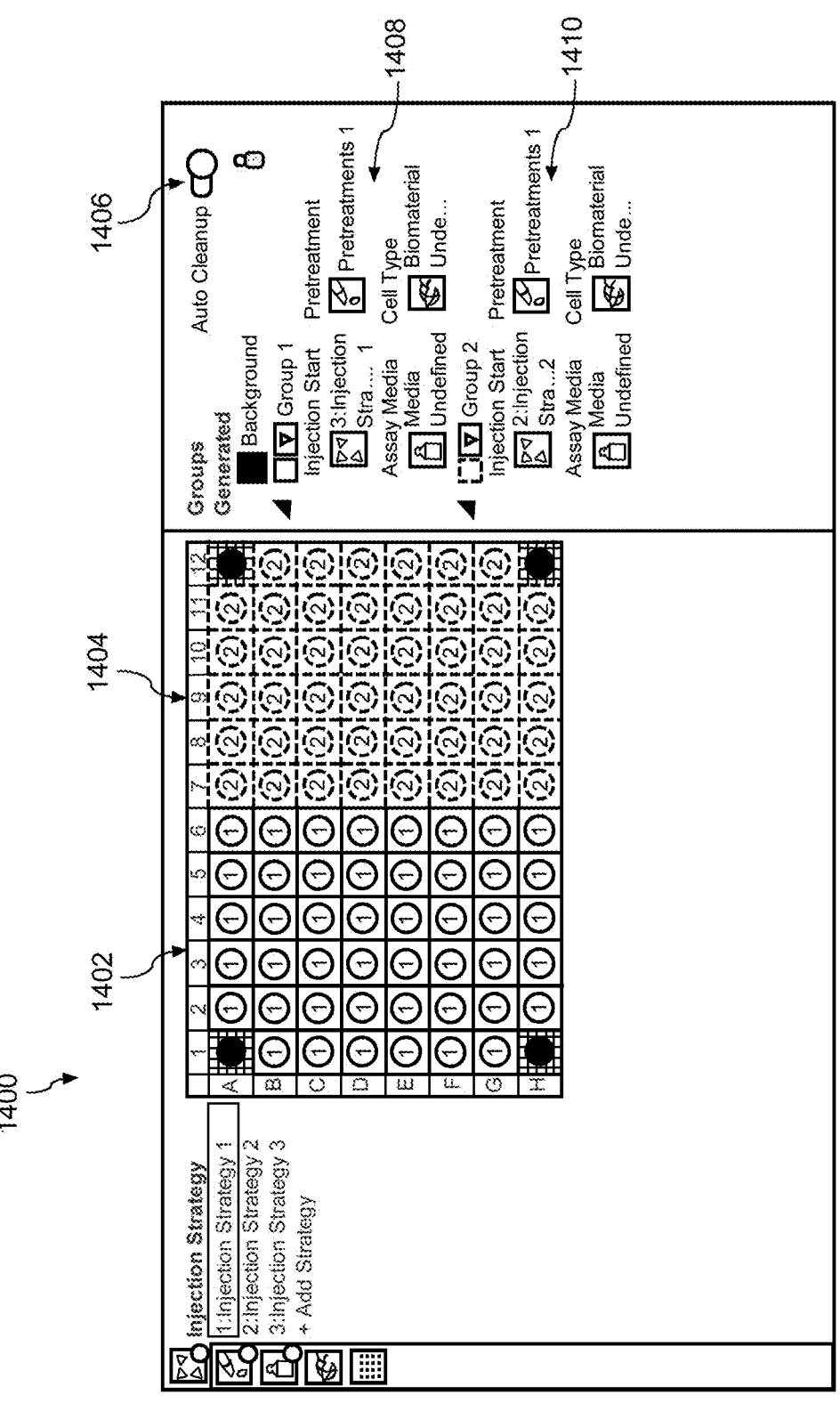
FIG. 14A depicts an illustration of an example automatic group cleanup according to example embodiments of the present disclosure.
Figure 14B:
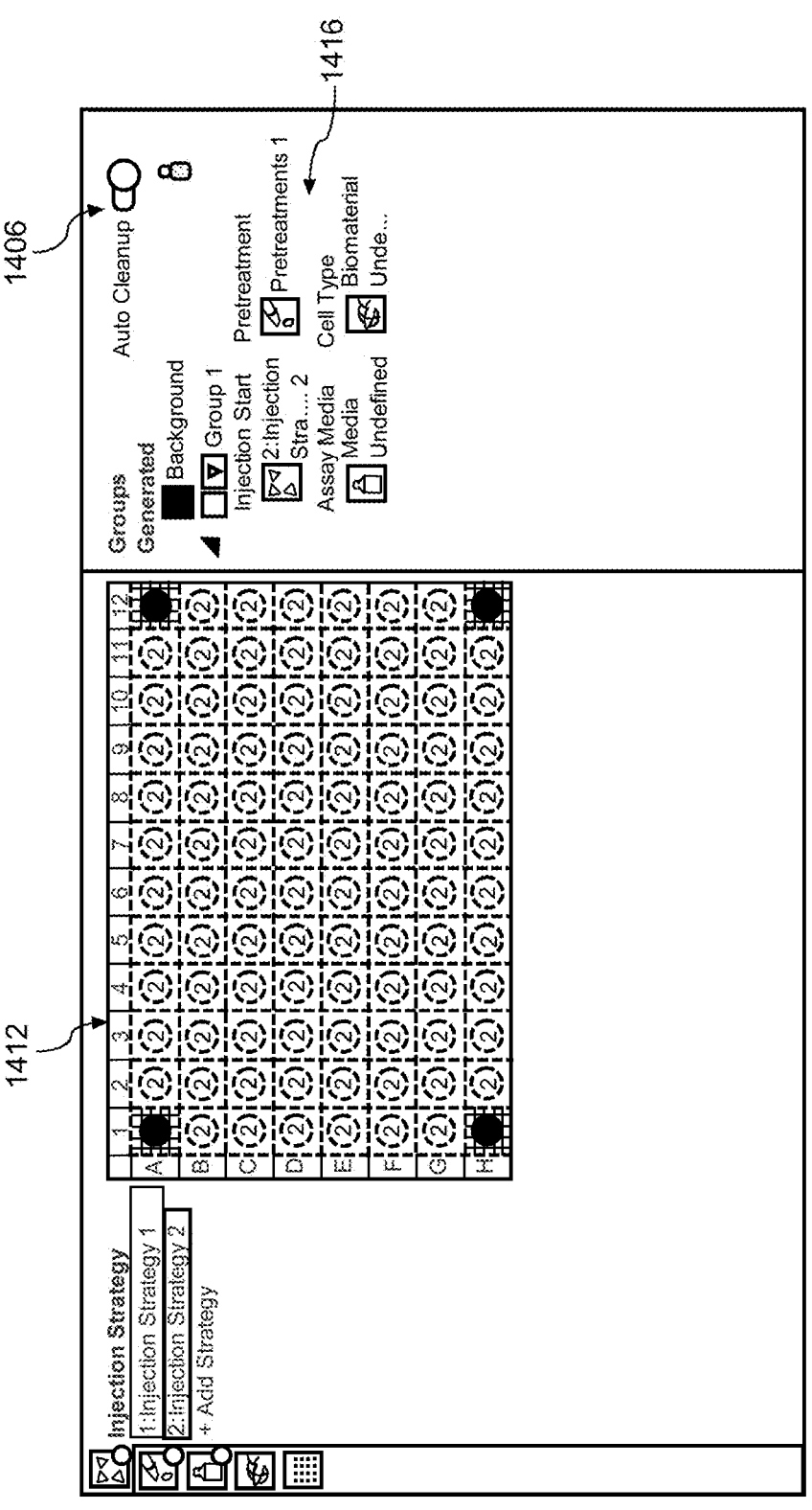
FIG. 14B depicts an illustration of an example automatic group cleanup according to example embodiments of the present disclosure.

FIGS. 14A and 14B depict an illustration of an example automatic group cleanup 1400 according to example embodiments of the present disclosure. In particular, FIG. 14A depicts group information for two generated groups in the generated groups column. The first generated group 1408 can include a first set of experiment parameters, and the second generated group 1410 can include a second set of experiment parameters. In FIG. 14A, the first set of experiment parameters are assigned to the left side 1402 of a plate map, and the second set of experiment parameters are assigned to the right side 1404 of the plate map.

A user can select (or may have already selected) the automatic group cleanup feature by interacting with a slider 1406. The slider 1406 can be located in the top right corner of the client interface. In some implementations, the slider may change color based on whether the feature is turned on or off. Additionally and/or alternatively, the slider 1406 can have a spinning interface element (e.g., a buffer display that depicts a portion of the circumference of a circle changing color in a clockwise or counterclockwise direction) that is displayed as the automatic group cleanup feature processes the generated groups and the plate map to determine if any generated groups are not utilized and/or are a duplicate.

In response to the automatic group cleanup slider 1406 being in an on position, the systems and methods can process data associated with the plate map and the generated groups to determine if there are any duplicate or unused generated groups to determine if any groups should be merged and/or removed.

In FIG. 14B, the user assigned the second set of parameters to the left side 1402 of the plate map to generate a plate map with a single selected group 1412. The systems and methods can process (e.g., at a given interval or based on a user selection) data associated with the generated groups and the plate map to determine the first generated group 1408 is no longer in use. The group information for the first generated group 1408 can then be removed from the group column, and the second generated group 1410 can be renamed 1416.

Example Instruments and Experiments

The example instruments, or equipment, discussed below can be implemented as part of an experiment computing system in order to run or complete tasks as part of an experimentation process built by the systems and methods disclosed herein. For example, the instruments, or equipment may be controlled in response to an experiment built using the plate experiment interface. Controlling of the instruments, or equipment, may include manual control by a user, semi-automated control via a download and upload feature, and/or full connectivity with the client-server computing system via a wired network or a wireless network.

Figure 11:
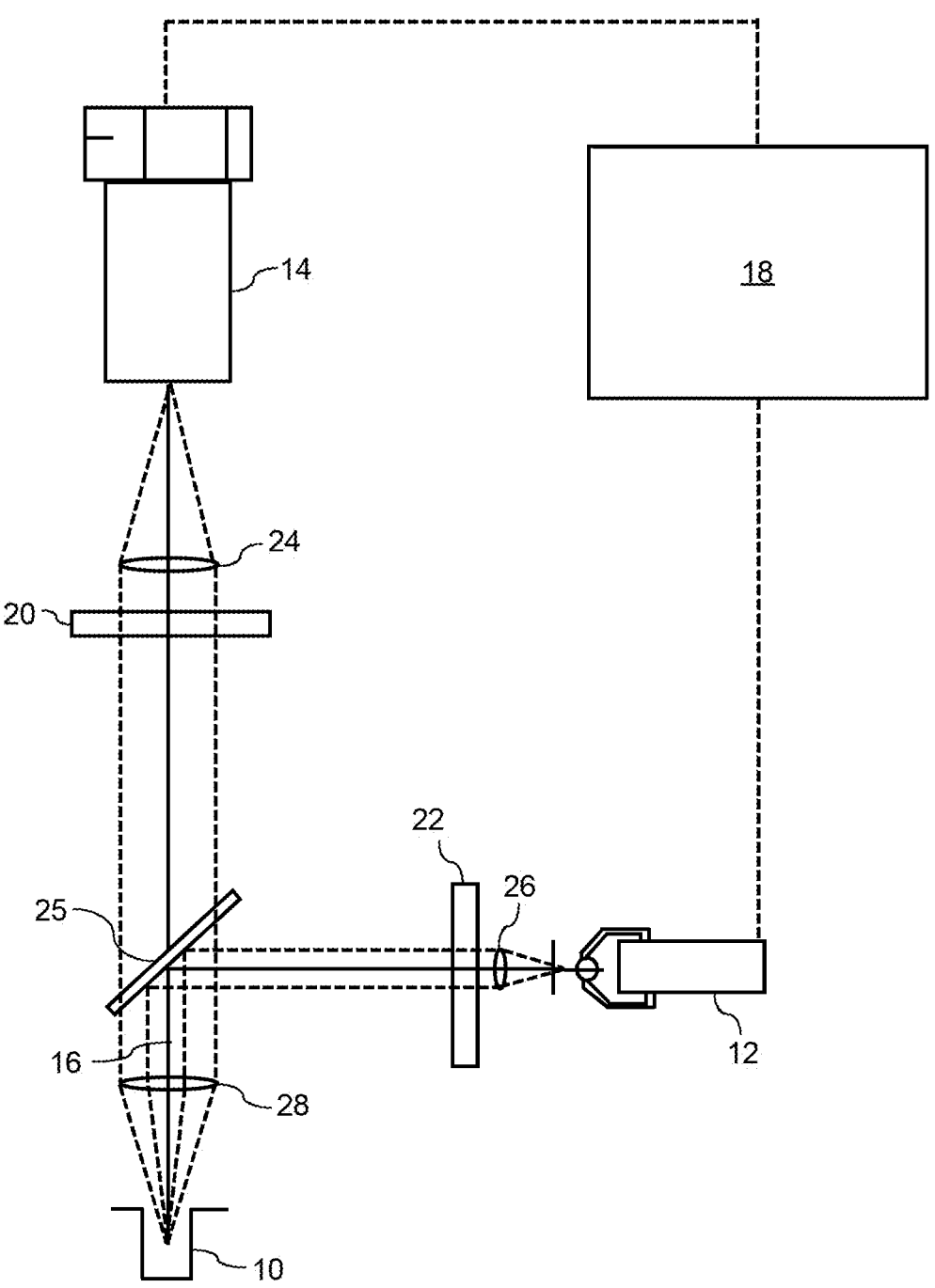
FIG. 11 depicts an illustration of an example diagrammatical view of one embodiment of a system made in accordance with exemplary embodiments of the present disclosure.

Referring to FIG. 11, for example purposes, a simplified diagram of one embodiment of a system configured to complete one or more of the experiments disclosed herein. As illustrated in FIG. 11, the system includes a sample staging site 10 that is positioned to receive excitation light from a light source 12. The light source 12 emits excitation light (e.g., modulated excitation light, such as a sinusoid or a series of pulses) that causes a fluorophore associated with a sample on the sample staging site 10 to undergo a fluorescent emission. The fluorescent emission is then sensed by a time of flight sensor 14, such as a CMOS time of flight sensor. The fluorophore can be a constituent contained in the biological sample naturally or can be added to the biological sample and be influenced by a constituent present in the biological sample.

The system further includes an optical communication path 16. The optical communication path is for directing the excitation light emitted by the light source 12 onto the sample staging site 10 and for directing a corresponding fluorescent emission to the time of flight sensor 14. The optical communication path 16 can include fiber optics. However, as discussed below, the optical communication path 16 can include any suitable optical path and/or optical elements for communicating optical signals.

The time of flight sensor 14, in one aspect, can include a pixel array comprising a plurality of pixels configured to receive signals from the optical communication path 16. For example, the signal received from the optical communication path 16 can be an optical signal that is indicative of a fluorescent emission that occurred by a fluorophore contained in the sample staging site 10. Each pixel or group of pixels in the pixel array, for instance, can be configured to provide a signal associated with a photo-response of the pixel or group of pixels based at least in part on the optical signal received. In some embodiments, the time of flight sensor 14 can be, for instance, an IMX556 time of flight sensor manufactured by Sony.

The system can further include one or more processors 18 that can be placed in communication with the time of flight sensor 14 and the light source 12. The one or more processors 18 can include, for instance, any suitable processing device, such as one or more microprocessors, integrated circuits (e.g., application specific integrated circuits), CPUs, GPUS, field programmable gate arrays, etc. that perform operations. In some embodiments, the one or more processors 18 can be configured to execute computer-readable instructions stored in one or more memory devices to perform operations, such as any of the operations for determining a response phase, a fluorescent intensity and/or fluorescent lifetime, and/or a magnitude of a characteristic described herein. The one or more memory devices can be any suitable media for storing computer-readable instructions and data. For instance, the one or more memory devices can include random access memory such as dynamic random access memory (DRAM), static memory (SRAM) or other volatile memory. In addition, and/or in the alternative, the one or more memory devices can include non-volatile memory, such as ROM, PROM, EEPROM, flash memory, optical storage, magnetic storage, etc.

The one or more memory devices can store computer-readable instructions that, when executed by the one or more processors 18, cause the one or more processors to perform operations, such as any of the operations implemented by one or more processors described herein. The instructions can be software written in any suitable programming language or can be implemented in hardware.

The one or more processors 18 can be configured to receive signals from the one or more pixels contained in the time of flight sensor 14. Based on information received from the time of flight sensor 14, the one or more processors 18 can be configured to determine a fluorescent lifetime or a fluorescent intensity of a fluorophore present in the sample staging site 10. In accordance with example aspects of the present disclosure, the one or more processors can be not only used to determine the existence of a biological constituent but can also be configured to determine a magnitude characteristic of the constituent or of a parameter related to the constituent from the fluorescent emission. The magnitude characteristic, for instance, can be an amount, a concentration, a rate of change, or the like. The magnitude characteristic can be mapped in two dimensions or in three dimensions.

As shown in FIG. 11, the one or more processors 18 can also be in communication with the light source 12. In this manner, the one or more processors 18 can control and coordinate light emissions from the light source 12 in conjunction with sensing fluorescent emissions using the time of flight sensor 14.

As shown in FIG. 11, the system can optionally include various different optical elements for directing light onto a sample and/or for directing fluorescent emissions towards the time of flight sensor 14. For instance, the system can include electro-optic modulators, beam-shaping lenses, scanning devices, multi-element lenses, light filters such as interference filters, beam splitters, aperture devices, and the like. For example, as shown in FIG. 11, the system can include light filters 20 and 22 in combination with lenses 24, 26 and 28. The system can also include a reflecting device 25 for directing light from the light source 12 onto the sample being tested. All of these optical devices, however, are optional and can be eliminated based upon the different equipment used. Optical elements, however, can be helpful for focusing light on a particular area. For instance, if the optical communication path 16 is larger than the sensing or imaging area of the time of flight sensor, one or more lenses can be used in order to alter or direct the light. In some embodiments, the optical path can include one or more fiber optics or light pipes.

Light source 12 can generally comprise any suitable light source. For example, the light source 12 can be configured to emit coherent light (e.g., a coherent light beam) or incoherent light. When emitting incoherent light, if desired, one or more filters can be used in order to filter out unwanted wavelengths. The one or more filters may be positioned before the light contacts the biological material for filtering the light being emitted by the light source 12 and/or can be positioned between the biological material and the time of flight sensor for filtering the fluorescent emission produced by the fluorophore. Suitable light sources 12 that can be used in the system of the present disclosure include, for instance, light emitting diodes, laser diodes, lasers, and the like. The light source 12 can also comprise one or more of the above light devices. For instance, the light source 12 can comprise a plurality of lasers, light diodes, or light emitting diodes for providing sufficient intensity over a desired area.

The wavelength at which the light source 12 operates can vary depending on the fluorophore present and/or the biological constituent being examined. The wavelength, for instance, can vary from about 250 nm to about 10,000 nm, such as from about 300 nm to about 2000 nm. As used herein, the use of the term "about" in conjunction with a numerical value can refer to within 10% of the stated numerical value. The light source 12, for example, may emit ultraviolet light, visible light, near infrared light or mixtures thereof.

The illumination intensity of the light source 12 can depend upon various factors and parameters including the operating wavelength, the sensitivity of the time of flight sensor 14, and the signal to noise ratio of the system. In one aspect, the light source 12 can be capable of delivering at least 102 photons per second, such as greater than about 104 photons per second, such as greater than about 108 photons per second, such as greater than about 109 photons per second, such as greater than about 1010 photons per second, such as greater than about 1011 photons per second, such as greater than about 1012 photons per second. The light intensity is generally less than about 1030, such as less than about 1020.

The optical communication path 16, in one embodiment, can comprise one or more light pipes or optical fibers. For example, in one embodiment, the optical communication path 16 can include a bundle array of optical fibers. The same optical fibers can be used to deliver light from the light source 12 onto the sample contained on the sample staging site 10 and to communicate a fluorescent emission to the time of flight sensor 14. Alternatively, different optical fibers can be used to carry out the different functions.

In one aspect, different optical fibers or different bundled arrays of optical fibers can be used to direct light onto different zones of sensor elements or pixels located on the time of flight sensor. In this manner, multiple measurements can be made simultaneously or near simultaneously from the same sample or different samples contained on the sample staging site 10.

For example, the system is capable of detecting and measuring multiple fluorescent emissions from different fluorophores contained in the same sample or different samples simultaneously or near simultaneously.

Multiplexing can also be used to measure the same fluorophore in a plurality of samples simultaneously or near simultaneously. For example, in one aspect, the system can include a plurality of sample staging sites. A single light source or multiple light sources can emit light onto each of the sample staging sites simultaneously or near simultaneously. The optical communication path 16 can be used in order to transmit fluorescent emissions from each sample staging site to different zones of sensor elements or pixels on the time of flight sensor 14 for simultaneously making multiple measurements. In fact, the system is capable of measuring fluorescent emissions from multiple fluorophores in each sample over a plurality of samples simultaneously or near simultaneously. For example, the system can include more than 10 sample staging sites, such as more than 25 sample staging sites, such as more than 50 sample staging sites, such as more than 75 sample staging sites, such as more than 100 sample staging sites, such as more than 125 sample staging sites, such as more than 150 sample staging sites, such as more than 175 sample staging sites, such as more than 200 sample staging sites, such as more than 225 sample staging sites, such as more than 250 sample staging sites, such as more than 300 sample staging sites, such as more than 400 sample staging sites, such as more than 500 sample staging sites and generally less than about 10,000 sample staging sites. In one aspect, the system can include a plurality of time of flight sensors in conjunction with one or more light sources for further increasing the number of sample staging sites contained within the system.

In one aspect, the time of flight sensor 14 can be part of a range imaging system or LiDAR system. Although the time of flight sensor 14 may be configured to resolve distances between the sensor and an object for each point of the image by measuring a round trip time of a light signal, the time of flight sensor 14, instead of measuring the round trip of a signal, measures the intensity or prompt decay of a fluorescent emission. For instance, when measuring fluorescent lifetimes, the time of flight sensor 14 begins a measurement at a fluorescent emission peak and then measures how rapidly the signal fades.

The time of flight sensor 14, in one embodiment, can be a modulated light source with one or more phase detectors. For instance, the time of flight sensor 14 can operate by modulating a light beam with a carrier and then measuring the phase shift of the carrier. Alternatively, the time of flight sensor can be a range-gated imager that has a built-in shutter that opens and closes such that light pulses are emitted by the light source 12.

In the system illustrated in FIG. 11, the light source 12, the time of flight sensor 14, and the one or more processors 18 are shown as separate elements. It should be understood, however, that each of these elements can be incorporated into a single device.

In the system illustrated in FIG. 11, the light source 12 and the time of flight sensor 14 are both positioned on the same side of the biological sample being tested; however, the light source and the flight sensor, in some implementations, can be on opposite sides of the sample.

The systems and processes according to example aspects of the present disclosure are well suited to measuring any biological constituent that can produce a fluorescent emission either alone or in combination with a fluorophore. In one aspect, for instance, the constituent can be contained in a biological sample, such as in cellular material. The constituent being tested can be a gas, a solid, a gel, or a liquid. The one or more constituents being measured can be measured from a living or viable sample or from a non-viable sample.

Constituents that can be measured from biological samples include all different types of metabolites. The method can include not only verifying the presence of the constituent but also determining a magnitude characteristic of the constituent or a parameter related to the constituent from the fluorescent lifetime or the fluorescent intensity. The constituent can be a lipid, an ion, a dissolved gas, a salt, a mineral, a nucleic acid, a protein, a polypeptide, or an enzyme. A parameter related to the constituent can be temperature, pH, an oxidation state, or a viscosity and the change the constituent causes to these parameters as a result of cellular metabolism. Dissolved gases that can be measured include oxygen, carbon dioxide, nitric oxide, or ammonia. The invention contemplates measuring the constituent and/or the parameter related to the constituent. In one embodiment, the constituent being measured oxygen consumption by the mitochondria of a cell and the parameter being measured is the by-product of oxygen consumption such as carbon dioxide, lactate, and the like. In another embodiment, the constituent or parameter being measured may comprise an intrinsically fluorescent metabolic cofactor, such as nicotinamide adenine dinucleotide (NAD$^+$/NADH), NAD(P)H, or flavin adenine dinucleotide (FAD/FADH$_2$). In one embodiment, nitrite reductase (NAD(P)H) can be monitored and analyzed. Nitrite reductase is an enzyme that catalyzes reactions related to nitrogen metabolism.

The constituent can be contained within the cell or can comprise a material secreted by the cells into the surrounding media. For example, any of the specific constituents or parameters described above can be monitored, analyzed or mapped in and around a cell's microenvironment. In one embodiment, the system can be used to measure changes in the constituent or parameter and provides rates of change in the particular parameter or constituent. In one embodiment, the microenvironment of a cell or cells can be monitored and modulated via external manipulation as a means of modelling in vivo conditions, such as hypoxia applications, TME modelling, Ischemia reperfusion, and the like.

The system of the present disclosure can provide information regarding a parameter or constituent in two dimensions or in three dimensions. The three dimensional diagram, for instance, can represent a gas concentration or partial pressure, such as oxygen. The three dimensional diagram, on the other hand, can represent a pH or temperature. The diagrams can provide robust information regarding the parameter of interest, including information regarding the parameter at a particular location and/or at a particular point in time.

In one aspect, the systems and processes according to example embodiments of the present disclosure can be used to monitor the bioenergetics of live cells and in real time. For example, the systems and processes according to example aspects of the present disclosure can be used to monitor mitochondrial respiration and/or glycolysis of living cells. In some embodiments, the systems and processes may be used to monitor intracellular or microenvironmental pH, oxygen concentration, redox potential, or the like. These cellular functions typically revolve around the consumption of oxygen and the efflux of protons. In some embodiments, the systems and processes of the invention may be used to monitor other embodiments of metabolism or bioenergetics, such as redox potential, or relative concentrations of metabolites or cofactors such as NAD(P)H or FAD/FADH. The systems and processes according to example aspects of the present disclosure can be used to detect extracellular changes in these parameters in order to measure rates of cellular respiration, glycolysis, and ATP production.

The cells being tested can comprise any suitable cell sample, including but not limited to cultured cells, primary cells, human cells, neurons, T cells, B cells, epithelial cells, muscle cells, stem cells, induced pluripotent stem cells, immortalized cells, pathogen-infected cells, bacterial cells, fungal cells, plant cells, archaeal cells, mammalian cells, bird cells, insect cells, reptile cells, amphibian cells, and the like. The cells being tested may also comprise three-dimensional cell samples, such as tissue samples, cell spheroids, biopsied samples, cell scaffolds, organs-on-a-chip, and the like. Examples of parameters that may be measured and are related to the above cell functions include carbon dioxide concentration, oxygen concentration or oxygen partial pressure, calcium ions, hydrogen ions, and the like. Through these tests, one can gain an understanding of what drives cell phenotype and function and/or an accurate picture of the cellular environment or microenvironment.

The systems and processes can be particularly well suited to monitoring fluorophores with very short fluorescent lifetimes, including fluorophores indicative of pH including pH rate changes over time. Fluorophores related to pH, for instance, are known to have extremely short fluorescent lifetimes. Systems and processes according to example aspects of the present disclosure, however, can operate at modulation rates that can measure fluorescent lifetimes of less than about 100 nanoseconds, such as less than about 75 nanoseconds, such as less than about 50 nanoseconds, such as less than about 40 nanoseconds, such as less than about 30 nanoseconds, such as less than about 20 nanoseconds, such as less than about 15 nanoseconds, such as less than about 10 nanoseconds, such as less than about 8 nanoseconds, such as less than about 6 nanoseconds, such as less than about 4 nanoseconds, such as less than about 3 nanoseconds, such as less than about 2 nanoseconds, such as even less than about 1 nanosecond. In fact, it is believed that the systems and processes can detect fluorescent lifetimes as short as 0.1 nanoseconds or greater.

The systems and processes can be used to measure live cell metabolic data, or (micro)environmental conditions of any viable cell. The cellular material being tested, for instance, can comprise bacteria cells, fungus cells, yeast cells, prokaryotic cells, eukaryotic cells, and the like. Cells that can be tested include mammalian cells including animal cells and human cells. Particular cells that can be tested include cancer cells, immune cells, immortal cells, primary cells, induced pluripotent stem cells, cells infected with viral or bacterial pathogens, and the like.

For example, in one aspect, the systems and processes can be used to assist in immunotherapy. Immunotherapy is a type of treatment that bolsters a patient's immune system for fighting cancer, infections, and other diseases. Immunotherapy processes, for instance, can include the production of T cells and/or natural Natural Killer (NK) cells. During T cell therapy, for instance, T cells are removed from a patient's blood. The T cells are then sent to a bioreactor and expanded or cultivated. In addition, the T cells can be changed so that they have specific proteins called receptors. The receptors on the T cells are designed to recognize and target unwanted cells in the body, such as cancer cells. The modified T cells are cultivated in a bioreactor to achieve a certain cell density and then supplied to a patient's body for fighting cancer or other diseases. T cell therapy is typically referred to as chimeric antigen receptor (CAR) T cell therapy. The use of T cells for CAR therapy has recently proliferated due to great success in combating blood diseases. In some embodiments, aspects of the present invention may be used to monitor the health of T cells used in (CAR) T cell therapy. In some embodiments, aspects of the present invention may be used to monitor T cell activation, T cell exhaustion, T cell metabolism, and the like.

NK cells are a type of cytotoxic lymphocyte that can seek out and destroy infected cells within the body. NK cells can display very fast immune reaction responses. Consequently, the use of NK cells in anticancer therapy has grown tremendously in interest and popularity. There is only a limited number of NK cells in the blood of a mammal, however, requiring that NK cells be grown to relatively high cell densities within bioreactors.

The culturing of cells, such as T cells, NK cells, or other mammalian cells, typically requires a somewhat complex process from inoculation to use in patients. The system and process of the present disclosure can be used to monitor cell metabolism during any point in the culturing process to ensure that the cells are healthy, and/or have the desired metabolic phenotype, and that the media in which the cells are growing contains an optimized level of nutrients. The system and process, for instance, can be used to make adjustments for assuring the metabolic fitness of the cells as they are growing.

In addition to immune cells, the metabolism of cancer cells can also be monitored for providing an understanding of which nutrients fuel the cancer cells. For example, the systems and processes according to example aspects of the present disclosure can reveal mechanisms or components that impact the metabolism of the cancer cells for inhibiting growth. The systems and processes according to example aspects of the present disclosure can also be used to determine the speed at which the cancer cells may proliferate. The system and process of the present disclosure is also well suited for use in toxicology. For instance, the process and system of the present disclosure can be used to detect mitochondrial liabilities among potential therapeutics. The risk of mitochondrial toxicity, for instance, can be assessed with high specificity and sensitivity. In this manner, the mechanism of action of some mitochondrial toxicants can be determined.

The systems and processes according to example aspects of the present disclosure can also be used to assist in treating obesity, diabetes, and metabolic disorders. For instance, the process and system can be used to measure functional effects of genetic changes to metabolic pathway components. Nutrients used in healthy and diseased cell models can be examined. Further, fatty acid oxidation and glycolysis can be assessed in different cell types.

When measuring cellular parameters related to cellular material, the constituent of interest can be contained within the cell or can be measured from a medium surrounding the cell. For instance, the cell parameter or constituent can be secreted by the cell into the surrounding medium and measured. The sample staging site can be configured to have compatibility with both adherent and suspension cells as well as isolated mitochondria.

When testing for and measuring a fluorophore, single measurements can be taken under some circumstances. The systems and processes, however, can be well suited to taking multiple measurements very rapidly to permit multiple determinations of fluorescent lifetime or fluorescent intensity of a fluorophore related to a biological parameter. For example, the fast cycle times in conjunction with significant multiplexing capabilities allows for conducting multiple measurements of the fluorophore very quickly. For instance, the fluorescent lifetime or fluorescent intensity of a fluorophore related to a cellular parameter, can be determined multiple times in less than about 60 seconds, such as less than about 30 seconds, such as less than about 10 seconds, such as less than about 5 seconds, such as less than about 1 second, such as even less than about 0.5 seconds. In the above periods of time, the fluorophore can be measured greater than 10 times, such as greater than 100 times, such as greater than 200 times. The multiple measurements can be used to determine rates of change and/or can be averaged for improving accuracy.

The system as shown in FIG. 11 can be incorporated into numerous and diverse instruments for measuring for the presence of constituents and/or for the presence of constituent or parameter concentrations. Referring to FIGS. 9-10 and 12A-13, one embodiment of a system incorporating the components illustrated in FIG. 11 is shown. The system illustrated in FIGS. 9-10 and 12A-12B is particularly well suited for conducting multiple assays simultaneously of biological samples, such as cellular material. The system illustrated in FIGS. 9 and 10, for instance, can be used to test multiple biological samples simultaneously and test for one or more constituents or cell parameters in each sample simultaneously.

Figure 9:
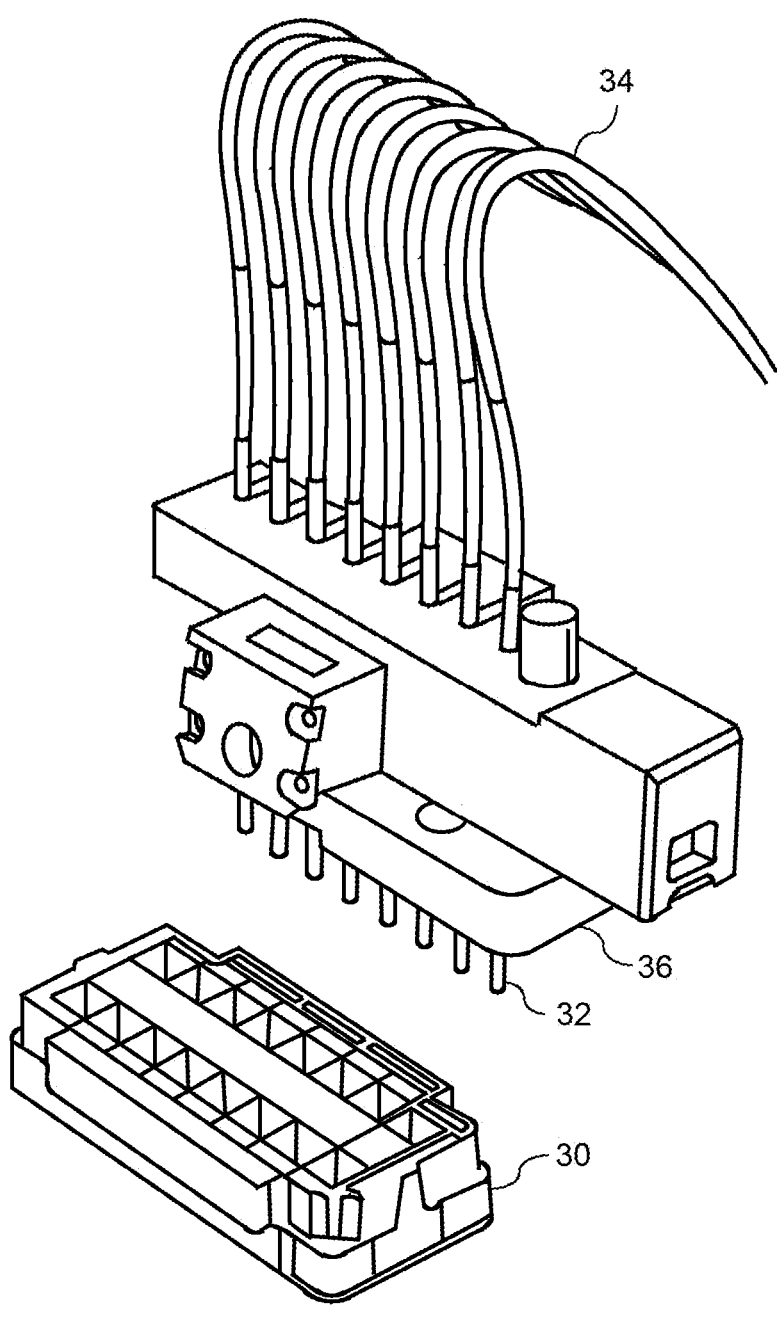
FIG. 9 depicts an illustration of an example embodiment of a system for analyzing biological material.
Figure 10:
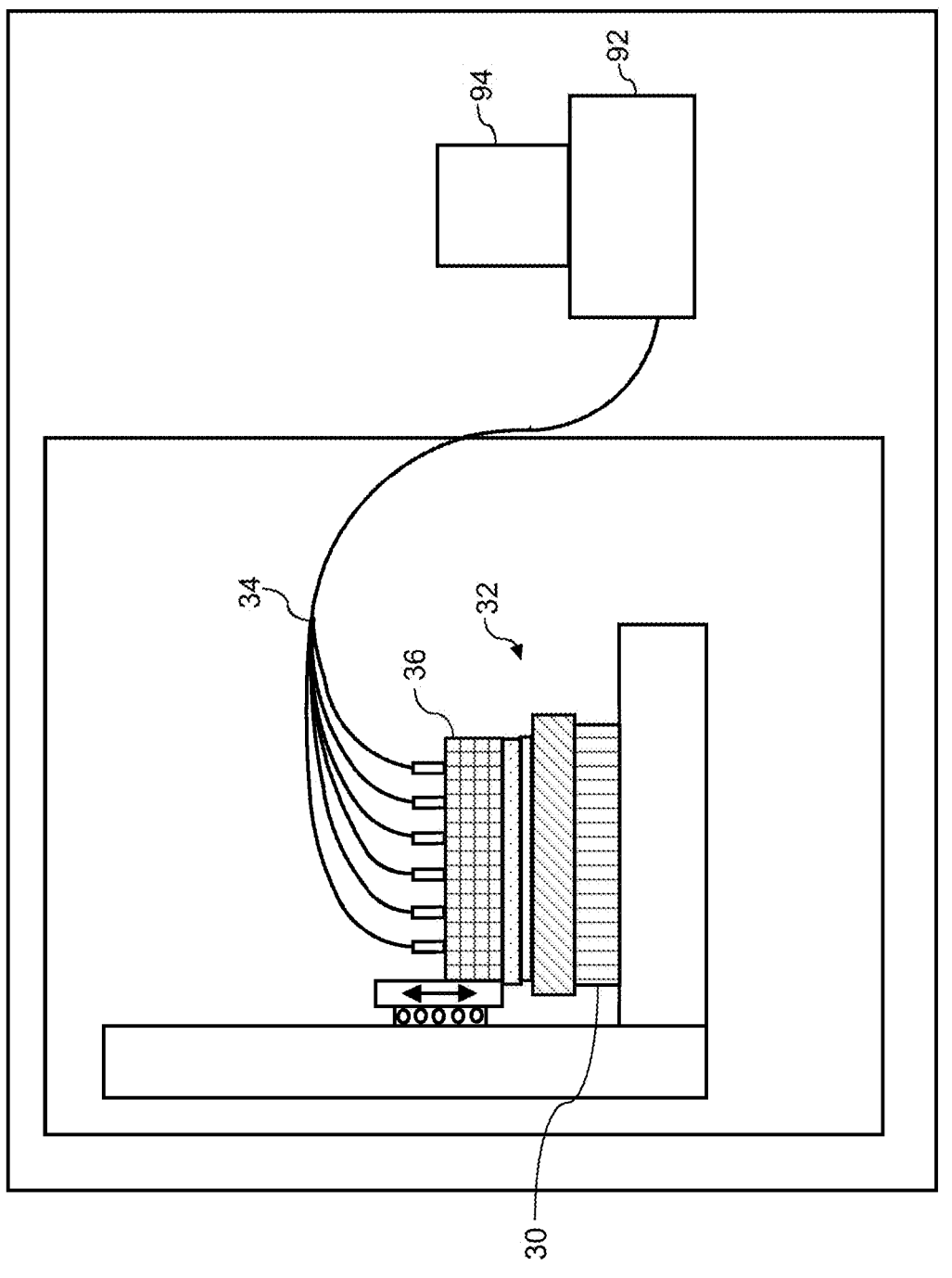
FIG. 10 depicts an illustration of an example cross-sectional view of the system illustrated in FIG. 9.

For illustrative purposes only, the invention in FIGS. 9 and 10 is demonstrated in an instrument configuration well suited to monitoring metabolic processes of live cells. The embodiment of FIGS. 9 and 10 is intended in no way to limit the scope of the present disclosure. The optical detection system of the present disclosure can be incorporated into any suitable biological sensor or imaging system. As shown in FIGS. 9 and 10, the system includes a microplate 30 that defines a plurality of sample staging sites for receiving biological samples. The microplate 30 is designed to be placed in association with a plurality of plungers or probes 32 that are configured to move towards and away from a microplate 30 loaded into the apparatus. Each plunger 32 is in communication with a light pipe 34. The light pipe 34 can be a single fiber optic or a bundle of fiber optics as shown. The light pipe 34 is for delivering light to biological samples contained in the microplate 30 and for communicating fluorescent emissions to a time of flight sensor.

As shown in FIGS. 9 and 10, the system can include a mounting block 36 which can hold the plungers 32. The mounting block can be in operative association with a motor for causing the mounting block 36 to reciprocate back and forth. Alternatively, the microplate 30 can be placed on a platform that lifts the microplate into contact with the plungers 32.

The light pipes 34 can be placed in communication with a light source and a time of flight sensor. The time of flight sensor and/or light source can also be placed in communication with one or more processors 92 (FIG. 10). The one or more processors 92 can obtain and process measurements from the time of flight sensor according to any of the systems and processes described herein. The one or more processors 92 can provide the information to a user via a display device 94 or other suitable user interface(s) (e.g., audio, visual, and/or interactive interface).

Figure 12A:
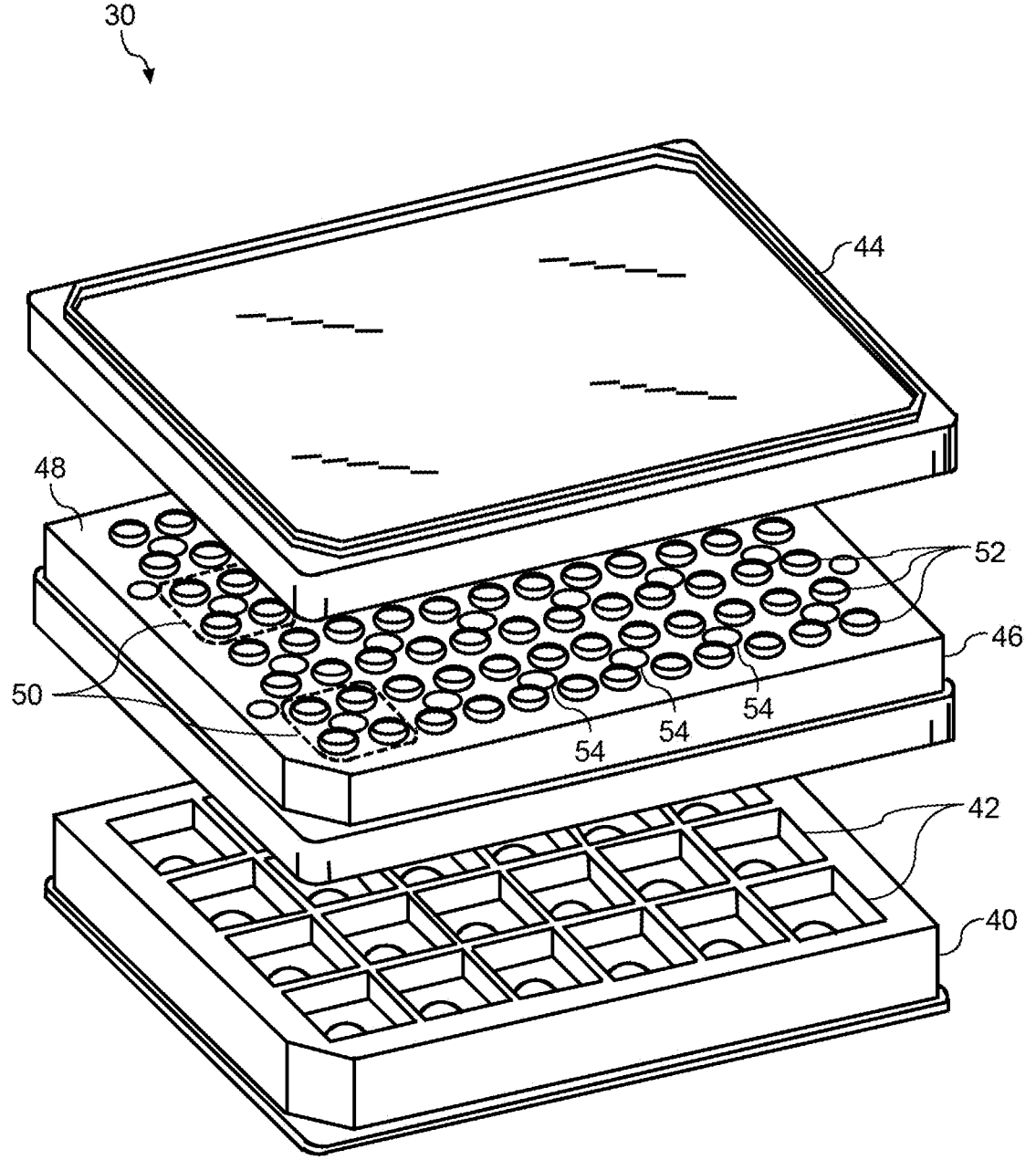
FIG. 12A depicts an illustration of an example exploded, perspective view of example embodiments of a microplate that may be used in accordance with the present disclosure for testing biological samples.
Figure 12B:
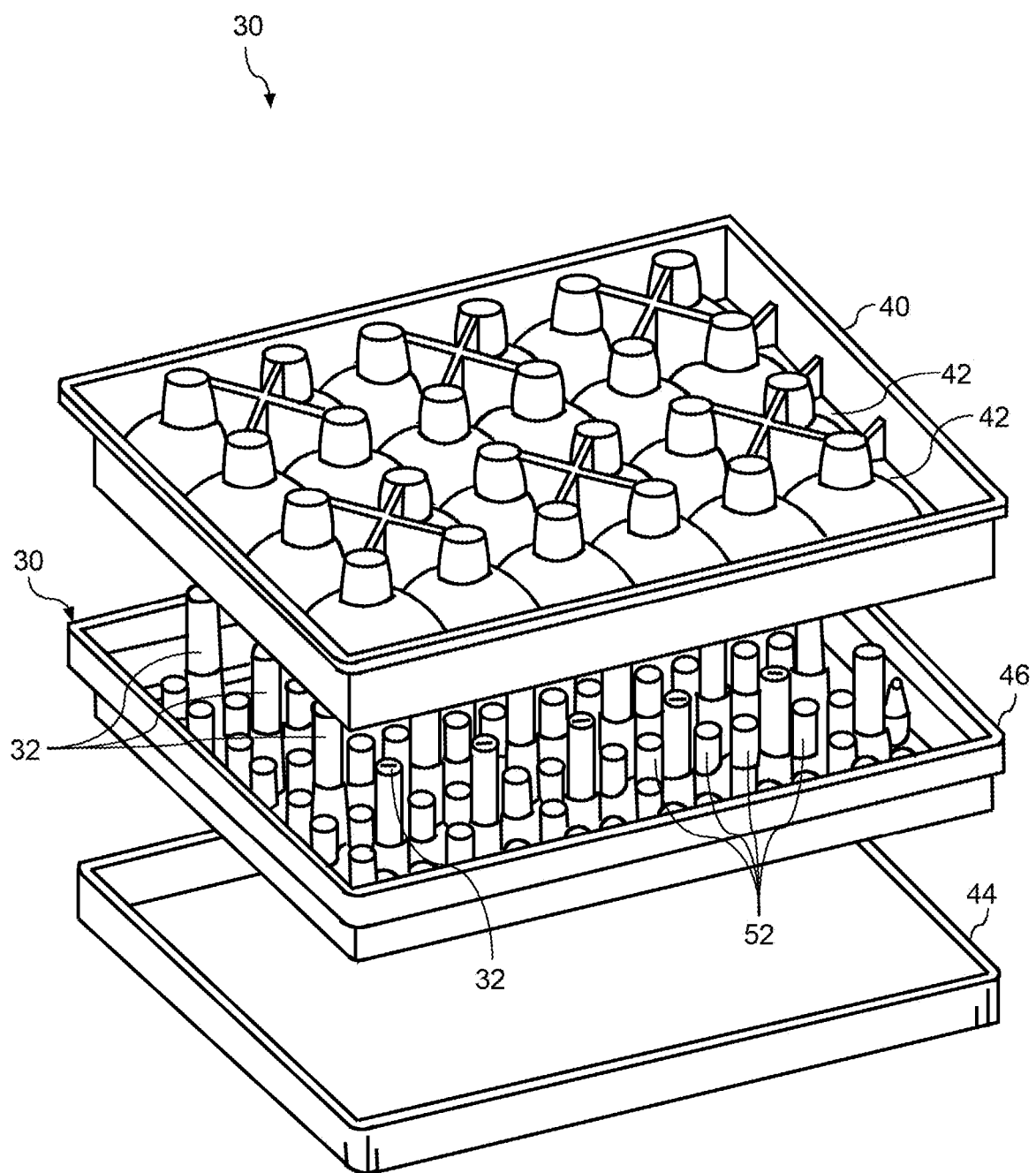
FIG. 12B depicts an illustration of an example inverted and exploded, perspective view of the microplate illustrated in FIG. 12A.

Referring to FIGS. 12A and 12B, one embodiment of a microplate 30 that can be used to hold biological samples, deliver one or more fluids to the samples, and assist in placing the samples in communication with the plungers 32 is shown. The microplate 30 can include a well plate 40 that defines a plurality of sample staging sites 42. The well plate 40 can be combined with a removable cover 44. Although the well plate 40 illustrated in FIG. 12A is shown containing 24 sample staging sites 42, it should be understood, as described above, that the well plate 40 can contain many more or less sample staging sites 42. In fact, the number of sample staging sites 42 can vary from one to several thousand or more. In some embodiments, a single sample staging site of nearly any size can be fabricated or multiple sample staging sites may be fabricated in a one-dimensional or two-dimensional arrangement.

Referring back to FIGS. 12A and 12B, the microplate 30 is generally a planar element comprising a frame 46. The different elements of the microplate 30 can be made from any suitable material, such as molded plastics or from a modular glass fixture. The frame 46 can include a surface 48 that defines a plurality of regions 50. The plurality of regions 50 can correspond with the number and location of the plungers illustrated in FIGS. 9 and 10. Likewise, the number and location of the plurality of regions 50 also correspond with the number and locations of the sample staging sites 42. In the embodiment illustrated in FIG. 12A, each region 50 includes first, second, third, and fourth ports 52. The injection ports 52, as will be described in greater detail below, facilitate delivery of gases and/or reagents to the sample staging sites 42. Each region 50 also includes a central aperture 54 for receiving a corresponding plunger 32. The injection ports 52 are sized and positioned so that groups of four ports may be positioned over a single sample staging site 42. A gas or liquid from the four ports may be delivered to a respective sample staging site 42. In other embodiments, the number of ports in each region can be less than four or greater than four. The central aperture 54 and each corresponding plunger 32 may be compliantly mounted relative to the well plate 40 so as to permit it to nest within the well plate by accommodating lateral movement.

Each of the ports 52 may have a cylindrical, conical, or cubic shape that defines an opening through the surface 48 of the frame 46. Each injection port 52 can also be closed at the bottom facing the sample staging site 42 except for a small hole, such as a capillary aperture. The aperture or hole can be centered along the bottom surface. The capillary aperture is adapted to retain test fluid in the port 52 such as by surface tension, absent an external force, such as a positive pressure differential force, a negative pressure differential force, or possibly a centrifugal force. Each port 52 may be fabricated from a polymer material that is impervious to gases, test fluids, or from any other solid material. The liquid volume of each port 52 can vary. In one aspect, for instance, the liquid volume of each port 52 can range 200 microliters to about 500 microliters, although volumes outside this range are contemplated.

Referring to FIG. 12B, the microplate 30 is shown in an inverted configuration. In addition, plungers 32 are shown extending through the central apertures of the frame 46. The plungers 32 are adapted to be inserted into each of the sample staging sites 42 for coming into proximity with the biological sample being tested.

The removable cover 44 is also illustrated in FIG. 12B. The cover 44 can be used to help prevent evaporation or contamination of a sample or of a media disposed in the microplate.

Figure 13:
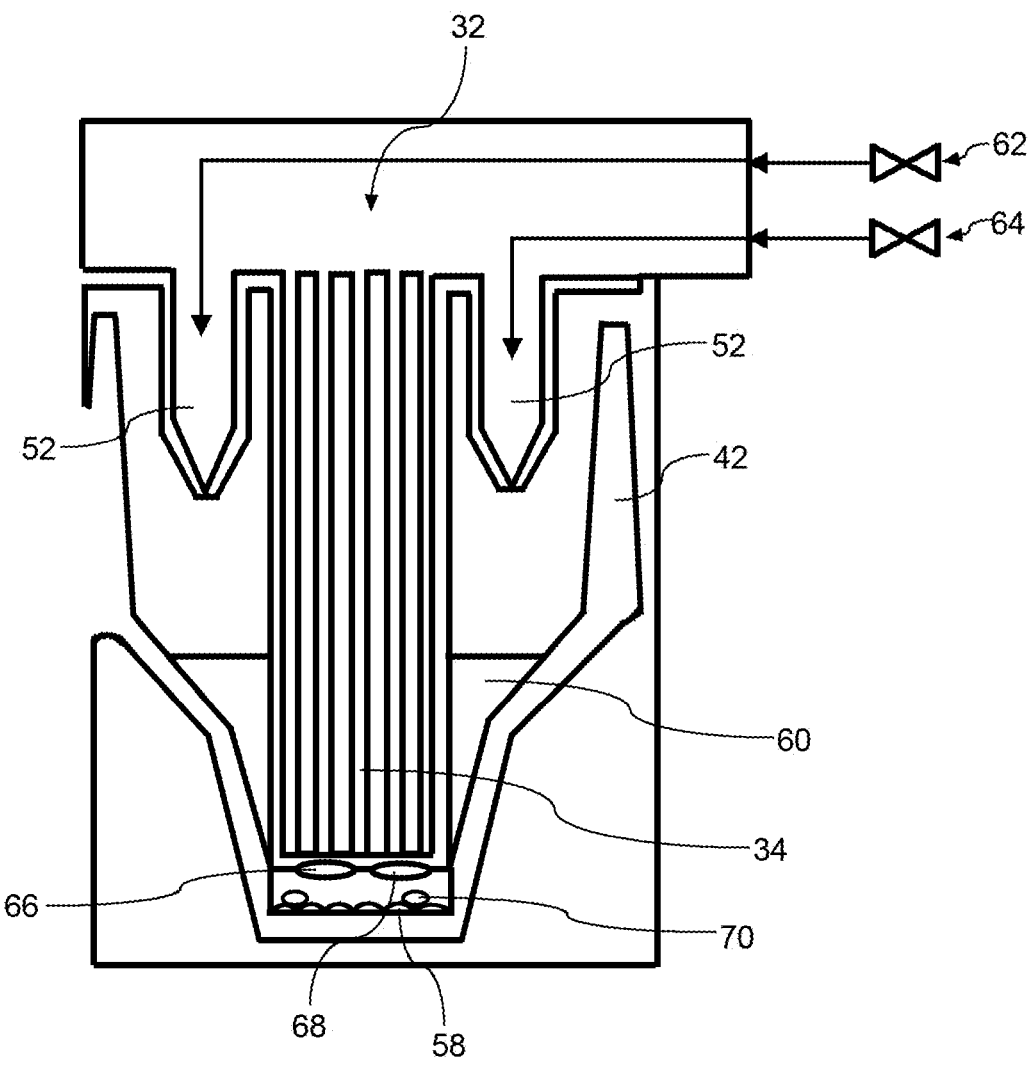
FIG. 13 depicts an illustration of an example cross-sectional view of one embodiment of a biological sample contained in a sample staging site in association with a probe or plunger and one or more component ports for taking measurements in accordance with example aspects of the present disclosure.

Referring to FIG. 13, a cross-sectional view of a single sample staging site 42 is shown. The sample staging site 42 contains a biological sample 58 contained in a media 60. The biological sample 58 contains one or more constituents or cellular parameters to be tested. In FIG. 13, a probe or plunger 32 is shown in association with the sample staging site 42 such that the plunger 32 is in contact with or close proximity to the biological sample 58. As described above, the plunger 32 is designed to reciprocate between a testing position as shown in FIG. 13 and a non-engagement position where the plunger is withdrawn from the sample staging site 42.

Two injection ports 52 are also illustrated that are designed to deliver fluids, such as liquids and gases, to the sample staging site 42. For example, in one embodiment, the ports 52 can be in communication with an external gas supply 62 and an internal air control 64. The external gas supply 62 and the internal air control 64 can control gases fed to or removed from the head space above the media 60. The internal air control 64 may be ambient air from inside the instrument that is compressed via a small internal compressor to pressurize the ports 52 to deliver fluids, such as drug compounds. The delivery of gas to the head space may allow manipulation of the environment around the test sample to create conditions simulating hypoxia, anoxia, or normoxia and/or low pH. In some embodiments, a biologically inert gas such as nitrogen may be injected into the media 60 in the sample staging site 42 above the surface of the media 60 for controlling the composition of gas in the head space or in the media. The gas can be used to flush the headspace if desired.

As described above, for instance, each sample staging site 42 may be in combination with four ports 52. The injection ports 52 can be used to deliver various compounds to the biological sample 58 within the sample staging site 42. For example, a common test performed on the instrument is a mitochondrial stress test. In this assay, a series of injections are delivered through the drug ports of the microplate in order to measure the response of the biological sample to various compounds (oligomycin, FCCP, rotenone and antimycin). These compounds are preloaded into a drug reservoir (port) on the microplate prior to execution of the assay. When the microplate is inserted into the instrument it is coupled to a manifold which when activated by a solenoid valve, provides pneumatic pressure to the head space of the reservoir forcing the compound through a small orifice and into the sample staging site 42 containing the biological sample. The pneumatic manifold and valve system may be modified to redirect one of these ports to an external gas supply (gas cylinder or bottle). The gas supply may be connected to the instrument through a port on the rear connector panel. The bottle may be located near the instrument and may contain a regulator and bubbler for humidification of the incoming gas. When activated, a solenoid valve may open, allowing the gas to flow through the manifold/microplate interface, through the drug port orifice, and into the head space above the biological sample. By oscillating the plunger (probe) vertically, the gas will be mixed with the medium allowing control of the available oxygen to the sample. For example, by perfusing nitrogen into the head space, the available $O_2$ in the medium is displaced and a more hypoxic condition is created around the sample. By turning off the gas and mixing, ambient levels of $O_2$ may be re-established.

In some implementations, a source of a solution of a biologically active substance may be in fluid communication with media in sample staging site 42 for exposing a sample to the substance.

The number of ports 52 associated with each sample staging site 42 determines the number of components that can be added to the sample staging site 42 during testing. In some implementations, no fluids are required for testing to occur. In other implementations, such as when conducting a mitochondrial stress test as described above, a plurality of different components may be fed to the sample staging site for affecting the conditions surrounding the biological sample 58. By having multiple injection ports 52, the system and process can also permit the testing of multiple conditions per each single staging site 42. In addition to a mitochondrial stress test, other tests that may be operated using the system illustrated in FIGS. 9-10 and 12A-13 are a ATP rate assay test that measures the rates of ATP production from glycolysis and mitochondrial respirations simultaneously, a glycolytic assay test that measures glycolysis in live cells revealing transient responses and rapid metabolic switches not discernible in other assays, a substrate oxidation test that measures cellular substrate oxidation by assessing changes in oxygen consumption in live cells, and a cell energy phenotype test that measures mitochondrial respiration and glycolysis.

As shown in FIG. 13, the plunger or probe 32 includes a plurality of fiber optics 34 that deliver excitation light to the biological sample 58 and transmit fluorescent emissions to the time of flight sensor for measuring fluorescent lifetimes and/or fluorescent intensity. In certain applications, the constituent being tested in the biological sample 58 can be auto-fluorescent or wherein a fluorophore is endogenous to the biological sample 58 for causing the constituent to undergo a fluorescent emission when contacted with excitation light. The system of the present disclosure is also well suited to producing images using FLIM. The image can be used to take measurements of various parameters including NAD(P)H.

Alternatively, the system can deliver one or more fluorescent emission agents, such as fluorophores, to the biological sample 58 that are influenced by the presence of a biological constituent when undergoing a fluorescent emission. For example, as shown in FIG. 13, the plunger 32 can include a pair of fluorophore sensors 66 and 68. The fluorophore sensors 66 and 68 can be the same or can be different for measuring different constituents or the same constituent under different conditions.

The fluorophore sensors 66 and 68 can contain any suitable fluorophore or fluorescent agent that facilitates a fluorescent emission. In general, fluorophores absorb light energy of a specific wavelength and re-emit the light at a different wavelength, such as a longer wavelength. The absorbed wavelengths, energy transfer efficiency, and time before emission depend on both the fluorophore structure and its chemical environment.

When the constituent being measured is oxygen concentration or oxygen partial pressure, a fluorophore can be used with the signal inversely proportional to oxygen concentration such as a porphyrin, ruthenium, or rhodamine compound immobilized as a particle or homogeneously distributed in an oxygen permeable polymer, such as silicone rubber or polyurethane hydrogel. When measuring pH, a fluorescent indicator dye can be incorporated into the fluorophore sensor. One such dye is fluorescein, whose signal decreases upon protonation of the dye and which is either in, on, or entrapped in a particle that is suspended in a carrier polymer or covalently attached to a hydrophilic polymer. A list of possible fluorophores indicative of pH include, but are not limited to the following in Table 1:

TABLE 1

| | | | $\tau(O_2)$ (ns) | $\tau(O_2)$ (ns) | $\tau$ (ns) | $\tau$ (ns) |
|---|---|---|---|---|---|---|
| pH | $\lambda_{ex}$ (nm) | $\lambda_{em}$ (nm) | low | high | low | high |
| Fluorescein | 460 | 550 | 3.6 | 4.2 | 3.6 | 4.2 |
| Fluorescein Na salt | 460 | 550 | 3.6 | 4.2 | 3.6 | 4.3 |
| Fluorescein diacetate | 460 | 550 | 3.5 | 4.0 | 3.5 | 4.0 |
| Fluoresceinamine Isomer 1 | 460 | 550 | 3.3 | 3.9 | 3.3 | 3.9 |
| Fluoresceinamine Isomer 2 | 460 | 550 | 3.0 | 3.9 | 3.0 | 4.0 |
| FITC | 460 | 550 | 3.4 | 4.1 | 3.4 | 4.1 |
| 6-Carboxyfluorescein | 460 | 550 | 3.5 | 4.0 | 3.5 | 4.0 |
| BCECF | 460 | 550 | 3.0 | 3.8 | 3.0 | 3.8 |
| SNAFL calcein | 460 | 550 | 3.4 | 2.7 | 3.4 | 2.7 |
| HPTS | 410 | 500 | 5.4 | 5.4 | 5.4 | 5.4 |
| 10-(3-Sulfonyl) acridinium betaine | 380 | 500 | 31.2 | 30.6 | 31.2 | 30.7 |
| Acridine Orange | 460 | 550 | 1.9 | 2.0 | 1.9 | 2.0 |
| Rhodamine B | 410 | 600 | 1.8 | 1.7 | 1.8 | 1.8 |
| Acridine | 380 | 450 | 26.3 | 13.7 | 26.3 | 14.0 |
| Acridine | 380 | 500 | 31.1 | 22.1 | 31.2 | 22.4 |

The above provides fluorescent lifetimes of dyes at a pH of between 5.2 and 7.9 in phosphate buffered solutions. The data is for oxygenated solutions and deoxygenated solutions.

When measuring carbon dioxide, a sensor that is based on a pH sensitive transducer can be used. The fluorescence can be indirectly modulated by the production of carbonic acid due to the reaction of carbon dioxide with water.

A fluorophore that detects glucose also can be used, such as one based on a non-enzymatic transduction using a boronic probe that complexes with glucose, resulting in a charge transfer that modulates the fluorescence of the probe, or an enzymatic glucose transducer that couples a glucose oxidase to a fluorescent oxygen sensor, with the binding and oxidation of glucose resulting in a quantitative modulation of the oxygen sensor. It also is within the scope of embodiments of the disclosure to employ a fluorophore or other type of sensor sensitive to biological molecules such as, for example, lactate, ammonia, or urea. A lactate sensor can be based on an enzymatic sensor configuration, with lactate oxidase coupled to a fluorescent oxygen sensor, and with the binding and oxidation of lactate resulting in a quantitative modulation of the oxygen sensor. An ammonia or ammonium ion sensor can be configured with immobilization of a protonated pH indicator in a hydrophobic, gas permeable polymer, with the fluorescence output quantitatively modulated by reaction with transient ammonia. A urea sensor can be based on an enzymatic sensor configuration, with urease coupled to a fluorescent ammonia transducer, and with the binding and reduction of urea to ammonia, resulting in modulation of the ammonia sensor fluorescence. The nature of the sensor generally does not form an aspect of embodiments of this invention.

As shown in FIG. 13, the fluorophore source can be located on the plunger or probe that is placed in communication with the biological material. Alternatively, the fluorophore source can be located in the biological material sample. The biological material may comprise cells and the fluorophore may be located within the cells, on the cell, or may be located in a microenvironment surrounding the cells. In one embodiment, the fluorophore may be encapsulated in nanoparticles or microparticles that are coupled to the plunger or probe, are in a suspension surrounding the cells, or are in a solution surrounding the cells.

In one aspect, the fluorophore sensor can also include a quenching agent. The quenching agent can facilitate measurements by impacting the fluorescent signal. In one aspect, for instance, an oxygen-quenched fluorophore sensor is used.

As shown in FIG. 13, the plunger 32 is designed to lower into the sample staging site 42 for being placed in association with the biological sample 58. In one aspect, the plunger 32 can be lowered so as to form a microchamber 70. Creation of a microchamber allows rapid, real-time measurement of a constituent or parameter that is changing. Formation of the microchamber, for instance, allows for measurements of changing oxygen and proton concentrations in an extracellular medium. More particularly, the microchamber 70 enables the temporary creation of a highly concentrated volume of biological sample 58 or cells within a larger volume of cell media. This permits the sensitive measurements of change in constituents of the media that results from the biological activity of the cells.

In one embodiment, if desired, the plunger 32 can also provide perfusion by creating hydrostatic pressure in the column of medium above the biological sample 58. For instance, the plunger 32 can reciprocate vertically through the sample staging site 42 causing media to flow across and sometimes through the biological sample 58. By moving the plunger 32 up and down, media is moved across the biological sample 58, replenishing nutrients, providing oxygen, and sweeping away waste. Accordingly, the microenvironment around the biological sample 58 may be continuously perfused between measurements. As the plunger 32 moves into the bottom portion of the sample staging site 42, motion is stopped, a small transient volume is created, and measurements are made. Efficiency of perfusion through the sample staging site 42 may be increased by altering the stroke height, speed and clearances between the plunger 32 and the bottom of the sample staging site 42.

It is appreciated that the instruments detailed in FIG. 9 through FIG. 13 are presented as exemplary embodiments for illustrative purposes only, and that the systems and methods embodied in the visual interface and associated experiment builder and plate assay builder of the present description may be implemented or otherwise integrated to operate in association with the experiment computing system of any number of differing instruments and associated imaging and/or sensing modalities (e.g., bioimpedance, extracellular recording, fluorescence, absorbance, luminescence, time-resolved etc.), particularly where those instruments incorporate grids or arrays of assays such as microplates.

Exemplary instruments may include, without limitation: real-time cell analysis instruments (e.g., xCELLigence RTCA analyzers and microplates produced by Agilent Technologies, Santa Clara, CA); real-time cell metabolic analyzers (e.g., Agilent Seahorse XF analyzers); benchtop flow cytometers (e.g. Agilent NovoCyte cytometers); cell imaging multimode microplate readers (e.g., BioTek Synergy and Cytation microplate readers); microplate spectrophotometers (e.g., BioTek Epoch), microplate absorbance readers (e.g., BioTek 800 TS); microbiology readers (e.g., BioTek LogPhase 600), automated liquid dispensing & handling instruments (e.g., BioTek washers, dispensers, Agilent Bravo automated liquid handling platform, etc.), automated incubators (e.g., BioTek Biospa 8 incubator); microplate stackers (e.g., BioTek BioStack), and automated cell imagers (e.g., BioTek Lionheart imagers).

In addition to instruments configured for cell analysis/preparation using microplates, the systems and methods embodied in the visual interface and associated experiment builder and plate assay builder of the present description may also be implemented to operate in association with the experiment computing system of instruments using arrays of other sample-holding receptacles (e.g., vials, chambers, etc.), as well as instruments analyzing samples such as tissue samples, or non-living constituents, compounds, etc. (e.g., liquid chromatography instruments, etc.).

In addition to scientific instruments, the systems and methods embodied in the visual interface and associated experiment builder and plate assay builder of the present description may also be implemented to operate in association with any operation that requires the assignment, tracking and analysis of multiple replicate data points (meta data) in cells organized in a table or grid. An example would be an Excel spreadsheet which organizes data in grid of cells with columns and rows, but in the case of Excel there is only one data point per cell.

Example Methods

Figure 6:
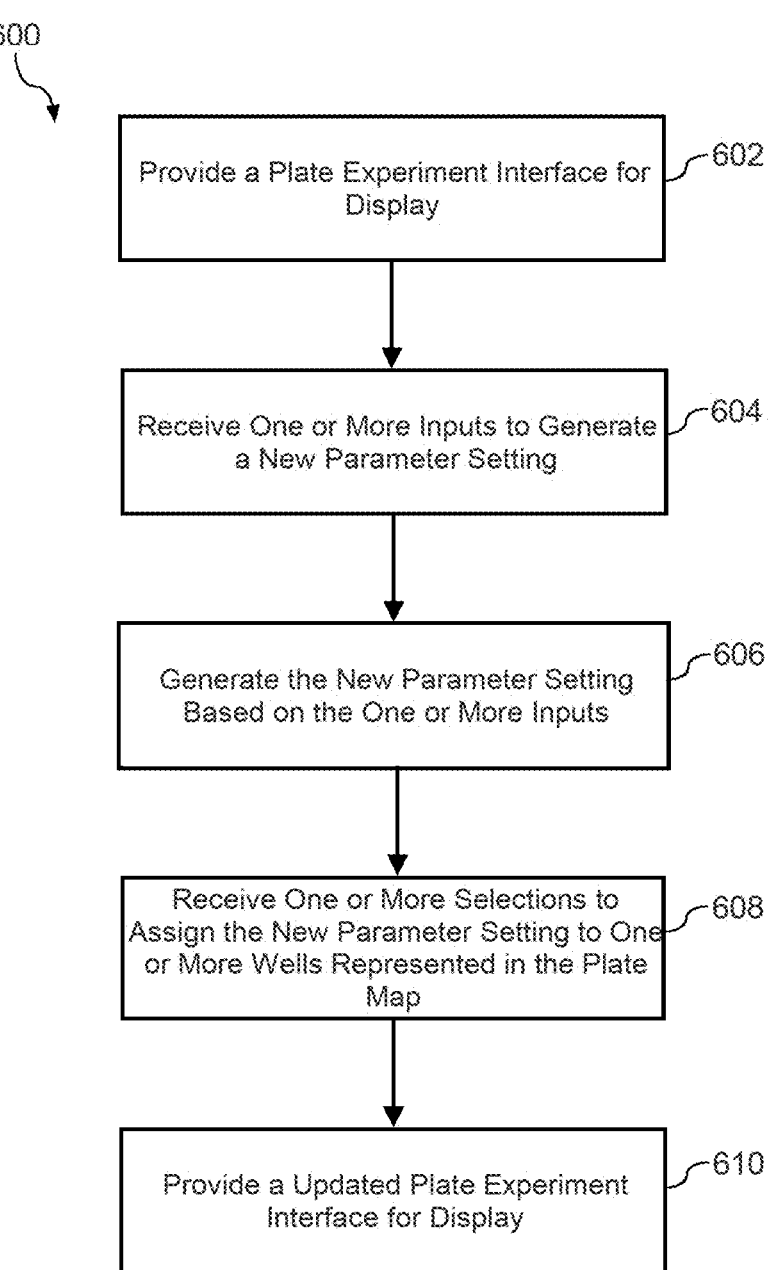
FIG. 6 depicts a flow chart diagram of an example method to perform experiment building according to example embodiments of the present disclosure.

FIG. 6 depicts a flow chart diagram of an example method to perform according to example embodiments of the present disclosure. Although FIG. 6 depicts steps performed in a particular order for purposes of illustration and discussion, the methods of the present disclosure are not limited to the particularly illustrated order or arrangement. The various steps of the method 600 can be omitted, rearranged, combined, and/or adapted in various ways without deviating from the scope of the present disclosure.

At 602, a computing system can provide a plate experiment interface for display. The plate experiment interface can be displayed via the display of a user computing device and may include one or more graphic elements. In some implementations, the plate experiment interface can include a plate map representative of a plurality of samples (e.g., a plurality of wells). Additionally, in some implementations, the plate experiment interface can include one or more tabs representative of one or more parameter types, in which each tab when selected displays different parameter information for assignment. The plate experiment interface may further include a grouping column descriptive of various groups with differing parameters.

At 604, the computing system can receive one or more inputs to generate a new parameter setting. The new parameter setting can be an injection parameter setting, a pretreatment parameter setting, an assay media parameter setting, a cell type parameter setting, and/or any other type of parameter setting. The inputs can select a pre-existing parameter setting or can be inputs that create a user-defined parameter setting. Parameter settings can vary based on the type of experiment and/or previous selections.

At 606, the computing system can generate the new parameter setting based on the one or more inputs. Generating the parameter setting can cause the parameter setting to be displayed in a parameter column that displays possible parameter settings for assignment.

At 608, the computing system can receive one or more selections to assign the new parameter setting to one or more wells represented in the plate map. The one or more selections can be drag-and-drop selections, gesture inputs, etc.

At 610, the computing system can provide an updated plate experiment interface for display. The updated plate experiment interface can include a plate map with one or more indicia indicating the assignment of one or more parameter settings to the one or more wells. In some implementations, a first indicia can indicate the assignment of the new parameter setting, and a second indicia can indicate a new grouping being created in response to the assignment. In some implementations, the first indicia can be a character (e.g., a number), and the second indicia can be a color (e.g., red).

In some implementations, the computing system can complete the method iteratively. For example, the computing system can receive one or more second inputs to generate a second parameter setting. The computing system can then generate the second parameter setting based on the one or more second inputs. The computing system can receive one or more selections to assign the second parameter setting to a subset of the one or more wells represented in the plate map. The computing system can then provide an adjusted plate experiment interface for display. The subset of the one or more wells can be displayed with a second color to indicate a second grouping, and the subset of the one or more wells can be displayed with a second character to indicate the subset of the one or more wells are assigned the second parameter setting.

Figure 7:
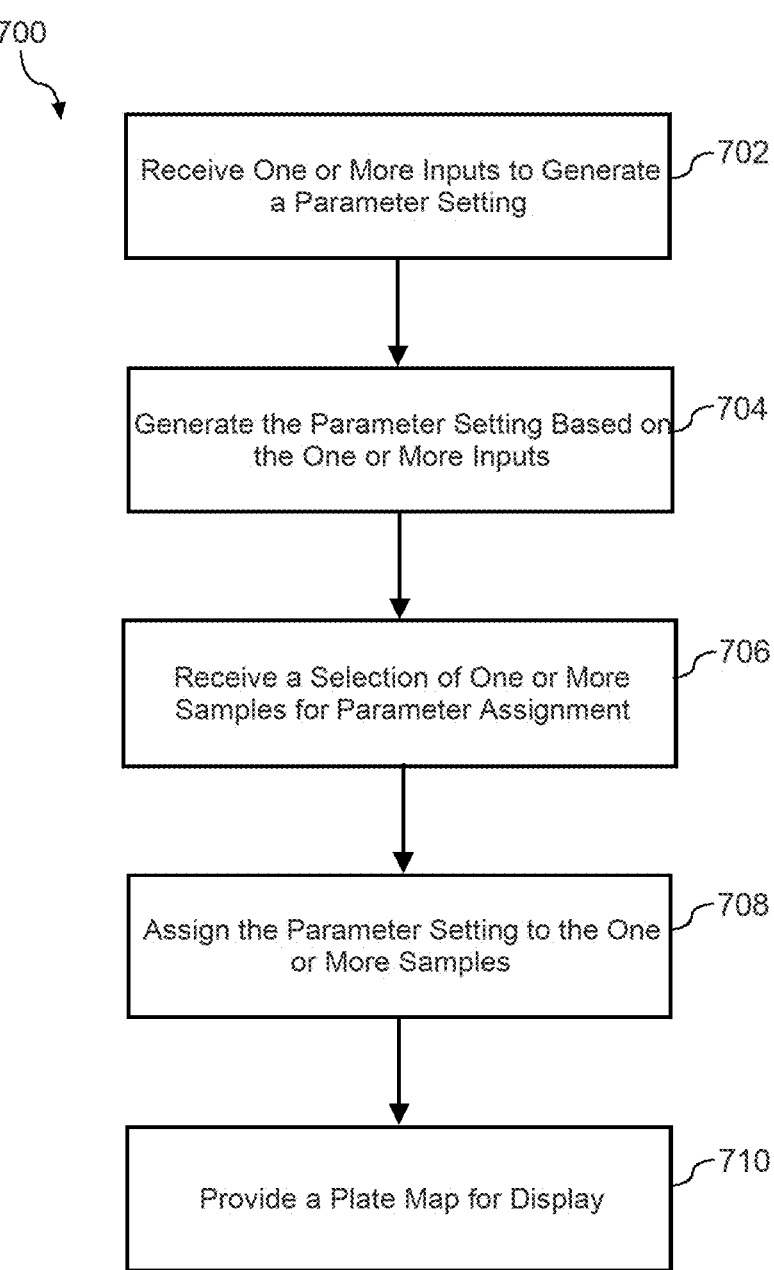
FIG. 7 depicts a flow chart diagram of an example method to perform experiment building according to example embodiments of the present disclosure.

FIG. 7 depicts a flow chart diagram of an example method to perform according to example embodiments of the present disclosure. Although FIG. 7 depicts steps performed in a particular order for purposes of illustration and discussion, the methods of the present disclosure are not limited to the particularly illustrated order or arrangement. The various steps of the method 700 can be omitted, rearranged, combined, and/or adapted in various ways without deviating from the scope of the present disclosure.

At 702, a computing system can receive one or more inputs to generate a parameter setting. The one or more inputs can be inputs received by a touch screen, a mouse, and/or keys of a keyboard. The parameter setting can be a setting indicative of a desired experiment parameter, such as a chemical compound for injection, a pretreatment for a well, etc.

At 704, the computing system can generate the parameter setting based on the one or more inputs. Generating the parameter setting can include processing the one or more inputs and determining a desired response.

At 706, the computing system can receive a selection of one or more samples for parameter assignment. The one or more samples can be wells in a plate experiment, a plurality of substrates, and/or specimens for testing.

At 708, the computing system can assign the parameter setting to the one or more samples. Assignment of the parameter setting can involve a variety of selection types and may be tailored to the type of experiment being built.

At 710, the computing system can provide a plate map for display. The plate map can be updated to include one or more indicia descriptive of one or more parameter settings assigned to the plurality of samples. For example, the number 1 in one or more of the boxes descriptive of the one or more samples can indicate a first parameter setting being assigned to the samples. In some implementations, a parameter column can be provided for display simultaneously with the plate map. The parameter column can include a title descriptive of a parameter type and one or more assignment-ready parameters, wherein the one or more assignment-ready parameters can include the parameter setting. Assignment-ready parameters can be parameter settings that can be selected and assigned to the one or more cells that represent one or more samples.

FIG. 8 depicts a flow chart diagram of an example method to perform according to example embodiments of the present disclosure. Although FIG. 8 depicts steps performed in a particular order for purposes of illustration and discussion, the methods of the present disclosure are not limited to the particularly illustrated order or arrangement. The various steps of the method 800 can be omitted, rearranged, combined, and/or adapted in various ways without deviating from the scope of the present disclosure.

At 802, a computing system can receive one or more inputs to generate a parameter setting. The one or more inputs can include one or more inputs to select a parameter tab and can include one or more inputs to select a predefined parameter or create a new parameter.

At 804, the computing system can generate the parameter setting based on the one or more inputs. Generating the parameter setting can involve receiving inputs with one or more sections of a pop-up menu.

At 806, the computing system can receive a selection of one or more wells for parameter assignment and assign the parameter setting to the one or more wells. Selection of the one or more wells can involve clicking and dragging inside the plate map to select a plurality of wells. For example, a user can click in a first box representative of a first well and drag laterally to select wells lateral to the first well, up and/or down for wells above or below the first well, and/or diagonally to select wells within a rectangular shape displayed with a plate experiment interface.

At 808, the computing system can provide a plate map for display. The plate map can include a plurality of colors representative of a plurality of groups and a plurality of characters representative of a plurality of parameter assignments.

At 810, the computing system can receive a selection input to begin an experiment. The selection input can include a finalization selection. In some implementations, the selection input can include a selection of a download graphic which can create a file that can be uploaded to an experiment instrument to complete an experiment action.

At 812, the computing system can control one or more injection instruments based on the parameter setting and the selection input. The injection instrument may inject one or more chemical compounds in response to the selection inputs. For example, a fixed amount of a chemical compound can be injected into each well the parameter setting was assigned to by the user.

ADDITIONAL DISCLOSURE

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:

1. A computer-implemented method for setting parameters for an experiment, the method comprising:
    providing, by a computing system comprising one or more processors, a plate experiment interface for display, wherein the plate experiment interface comprises a plate map;
    receiving, by the computing system, one or more inputs to generate a new parameter setting;
    generating, by the computing system, the new parameter setting based on the one or more inputs;
    receiving, by the computing system, one or more selections to assign the new parameter setting to one or more wells represented in the plate map; and
    providing, by the computing system, an updated plate experiment interface for display, wherein the one or more wells are displayed with a first indicia to indicate a first grouping, wherein the updated plate experiment interface comprises character indicia associated with parameter assignments associated with a selected parameter tab of a plurality of parameter tabs, and wherein the updated plate experiment interface comprises color indicia descriptive of groupings associated with parameters setting differences between groups of wells;
    receiving a selection input to begin an experiment; and
    controlling one or more instruments based at least in part on the new parameter setting and the selection input.

2. The computer-implemented method of claim 1, wherein the one or more wells are displayed with a first character to indicate the one or more wells are assigned the new parameter setting.

3. The computer-implemented method of claim 1, further comprising:
    adjusting, by the computing system, a parameter setting for each of the one or more wells based at least in part on the new parameter setting.

4. The computer-implemented method of claim 1, further comprising:
    receiving, by the computing system, one or more finalization selections from a user to finalize the new parameter setting; and
    providing, by the computing system, a finalization interface for display, wherein the finalization interface comprises an updated plate map and group information descriptive of a set of parameter settings for each respective grouping.

5. The computer-implemented method of claim 1, further comprising:
    receiving, by the computing system, a new tab selection from a user; and
    removing, by the computing system, a first indicia from the updated plate experiment interface.

6. The computer-implemented method of claim 1, wherein the plate experiment interface comprises the plurality of parameter tabs, wherein each tab is associated with a different display of the plate map.

7. The computer-implemented method of claim 6, wherein the plurality of parameter tabs comprise an injection strategy setting tab, a pretreatment setting tab, an assay media setting tab, and a cell type setting tab.

8. The computer-implemented method of claim 6, wherein the plurality of parameter tabs comprise a finalization tab, wherein the finalization tab is associated with a fully-configured plate map.

9. The computer-implemented method of claim 1, wherein the new parameter setting is at least one of an injection strategy setting, a pretreatment setting, an assay media setting, or a cell type setting.

10. The computer-implemented method of claim 1, further comprising:
    receiving, by the computing system, one or more second inputs to generate a second parameter setting;
    generating, by the computing system, the second parameter setting based on the one or more second inputs;
    receiving, by the computing system, one or more selections to assign the second parameter setting to a subset of the one or more wells represented in the plate map; and
    providing, by the computing system, an adjusted plate experiment interface for display, wherein the subset of the one or more wells are displayed with a second color to indicate a second grouping, and wherein the subset of the one or more wells are displayed with a second character to indicate the subset of the one or more wells are assigned the second parameter setting.

11. The computer-implemented method of claim 10, further comprising:
    receiving, by the computing system, secondary input data associated with a second parameter setting;
    generating, by the computing system, a second grouping with the second parameter setting;
    providing, by the computing system, group information associated with the first grouping and the second grouping for display in the updated plate experiment interface;
    determining, by the computing system, the second grouping is without assignment on the plate map; and
    removing, by the computing system, a subset of the group information from the updated plate experiment interface, wherein the subset is associated with the second grouping.

12. A computing system, the computing system comprising:
    one or more processors;
    one or more non-transitory computer readable media that collectively store instructions that, when executed by the one or more processors, cause the computing system to perform operations, the operations comprising:
        receiving one or more inputs to generate a parameter setting;
        generating the parameter setting based on the one or more inputs;
        receiving a selection of one or more samples for parameter assignment;
        assigning the parameter setting to the one or more samples;
        providing a plate map for display, wherein a portion of the plate map representing the one or more samples is displayed with one or more indicia, wherein the plate map comprises character indicia associated with parameter assignments associated with a selected parameter tab of a plurality of parameter tabs, and wherein the plate map comprises color indicia descriptive of groupings associated with parameters setting differences between groups of wells;
        receiving a selection input to begin an experiment; and controlling one or more instruments based at least in part on the parameter setting and the selection input.

13. The computing system of claim 12, wherein the plate map comprises at least 96 samples.

14. The computing system of claim 12, wherein the operations further comprise:

providing a groups column for display, wherein the groups column is displayed simultaneously with the plate map, and wherein the groups column comprises group information.

15. The computing system of claim 12, wherein the operations further comprise:

providing a parameter column for display, wherein the parameter column is displayed simultaneously with the plate map, and wherein the parameter column comprises a title descriptive of a parameter type and one or more assignment-ready parameters, wherein the one or more assignment-ready parameters comprise the parameter setting.

16. The computing system of claim 12, wherein the indicia comprises a first indicia descriptive of the parameter setting and a second indicia descriptive of a well grouping.

17. An experiment computing system, the experiment system comprising:

a plate comprising a plurality of wells;

one or more injection instruments;

one or more visual displays for displaying visual components of a user interface;

one or more input components configured to receive inputs from a user;

one or more processors;

one or more non-transitory computer readable media that collectively store instructions that, when executed by the one or more processors, cause the experiment computing system to perform operations, the operations comprising:

receiving one or more inputs to generate a parameter setting;

generating the parameter setting based on the one or more inputs;

receiving a selection of one or more wells for parameter assignment;

assigning the parameter setting to the one or more wells;

providing a plate map for display with the one or more visual displays, wherein a portion of the plate map representing the one or more wells is displayed with a plurality of indicia, wherein the plate map comprises character indicia associated with parameter assignments associated with a selected parameter tab of a plurality of parameter tabs, and wherein the plate map comprises color indicia descriptive of groupings associated with parameters setting differences between groups of wells;

receiving a selection input to begin an experiment; and controlling one or more injection instruments based at least in part on the parameter setting and the selection input.

18. The experiment computing system of claim 17, wherein the one or more injection instruments comprises a plurality of injection ports for injecting a plurality of compounds.

19. The experiment computing system of claim 17, further comprising: one or more pretreatment instruments.

20. The experiment computing system of claim 19, wherein the operations further comprise:

receiving one or more second inputs to generate a second parameter setting;

generating the second parameter setting based on the one or more second inputs;

receiving a second selection of a second set of one or more wells for a second parameter assignment;

assigning the second parameter setting to the second set of one or more wells; and controlling the one or more pretreatment instruments based at least in part on the second parameter setting and the selection input.

* * * * *